(12) United States Patent
Kinzel et al.

(10) Patent No.: US 10,220,027 B2
(45) Date of Patent: *Mar. 5, 2019

(54) FXR (NR1H4) BINDING AND ACTIVITY MODULATING COMPOUNDS

(71) Applicant: Gilead Sciences, Inc., Foster City, CA (US)

(72) Inventors: Olaf Kinzel, Heidelberg (DE);
Christoph Steeneck, Dossenheim (DE);
Claus Kremoser, Heidelberg (DE)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,530

(22) Filed: Oct. 13, 2017

(65) Prior Publication Data

US 2018/0200243 A1    Jul. 19, 2018

Related U.S. Application Data

(63) Continuation of application No. 15/369,521, filed on Dec. 5, 2016, now Pat. No. 9,820,979, which is a continuation of application No. 14/824,971, filed on Aug. 12, 2015, now Pat. No. 9,539,244, which is a continuation of application No. 14/232,118, filed as application No. PCT/EP2012/002941 on Jul. 12, 2012, now Pat. No. 9,139,539.

(60) Provisional application No. 61/507,153, filed on Jul. 13, 2011.

(30) Foreign Application Priority Data

Jul. 13, 2011    (EP) ..................................... 11005722

(51) Int. Cl.
| | |
|---|---|
| *A61K 31/4439* | (2006.01) |
| *A61K 31/42* | (2006.01) |
| *A61K 31/422* | (2006.01) |
| *C07D 261/08* | (2006.01) |
| *C07D 413/12* | (2006.01) |
| *C07D 413/14* | (2006.01) |

(52) U.S. Cl.
CPC .......... *A61K 31/4439* (2013.01); *A61K 31/42* (2013.01); *A61K 31/422* (2013.01); *C07D 261/08* (2013.01); *C07D 413/12* (2013.01); *C07D 413/14* (2013.01)

(58) Field of Classification Search
CPC .. A61K 31/4439; A61K 31/42; A61K 31/422; C07D 201/08; C07D 413/12; C07D 413/14

See application file for complete search history.

(56) References Cited

U.S. PATENT DOCUMENTS

| | | |
|---|---|---|
| 4,943,584 A | 7/1990 | Theobald et al. |
| 5,256,666 A | 10/1993 | Mueller et al. |
| 5,258,551 A | 11/1993 | Murabayashi et al. |
| 5,502,252 A | 3/1996 | Takase et al. |
| 5,633,272 A | 5/1997 | Talley et al. |
| 5,849,746 A | 12/1998 | Chambers et al. |
| 5,854,268 A | 12/1998 | Baker et al. |
| 5,912,243 A | 6/1999 | Dowling et al. |
| 6,407,140 B1 | 6/2002 | Gregory et al. |
| 6,974,830 B2 | 12/2005 | Bauer et al. |
| 7,034,046 B2 | 4/2006 | Bauer et al. |
| 7,098,336 B2 | 8/2006 | Bauer et al. |
| 7,560,551 B2 | 7/2009 | Cee et al. |
| 8,188,080 B2 | 5/2012 | Mustelin et al. |
| 8,193,192 B2 | 6/2012 | Kremoser et al. |
| 8,222,256 B2 | 7/2012 | Zhang |
| 8,952,042 B2 | 2/2015 | Kremoser et al. |
| 9,139,539 B2 * | 9/2015 | Kinzel ................. C07D 261/08 |
| 9,539,244 B2 * | 1/2017 | Kinzel ................. C07D 261/08 |
| 9,820,979 B2 * | 11/2017 | Kinzel ................. C07D 261/08 |
| 9,855,249 B2 | 1/2018 | Cole et al. |
| 2003/0130296 A1 | 7/2003 | Bauer et al. |
| 2003/0149087 A1 | 8/2003 | Bauer et al. |
| 2003/0187042 A1 | 10/2003 | Bauer et al. |
| 2004/0048908 A1 | 3/2004 | Momose et al. |
| 2004/0105883 A1 | 6/2004 | Gao et al. |
| 2004/0105884 A1 | 6/2004 | Gao et al. |
| 2004/0105885 A1 | 6/2004 | Gao |
| 2004/0106607 A1 | 6/2004 | Arora et al. |
| 2004/0131670 A1 | 7/2004 | Gao |

(Continued)

FOREIGN PATENT DOCUMENTS

| | | |
|---|---|---|
| CA | 1145344 A | 4/1983 |
| CN | 104045635 A | 9/2014 |

(Continued)

OTHER PUBLICATIONS

Abel, et al., (2010) "Synthesis and pharmacological validation of a novel series of non-steroidal FXR agonists" Bioorganic & Medicinal Chemistry Letters 20: 4911-4917.

Abu-Hayyeh et al., (2010) "Sulphated progesterone metabolites attenuate FXR function", 61st Annual Meeting of the American Association for the Study of Liver Diseases (Abstract).

Adams, et al., (2012) "In vitro and in vivo regulation of FGF21 by FXR" 2012 Genetic and Molecular Basis of Obesity and Body Weight Regulation (J7) held jointly with 2012 Pathogenesis of Diabetes: Emerging Insights into Molecular Mechanisms (J8) (Abstract).

Adorini (2008) "Clinical Translation of FXR agonists for the Treatment of Liver and Metabolic Disorders" 2008 Nuclear Receptors: Orphan Brothers (Z1) (Abstract).

(Continued)

*Primary Examiner* — Timothy R Rozof
(74) *Attorney, Agent, or Firm* — Sheppard Mullin Richter & Hampton LLP

(57) ABSTRACT

The present invention relates to compounds which bind to the NR1H4 receptor (FXR) and act as agonists of FXR. The invention further relates to the use of the compounds for the preparation of a medicament for the treatment of diseases and/or conditions through binding of said nuclear receptor by said compounds and to a process for the synthesis of said compounds.

16 Claims, 1 Drawing Sheet

(56) References Cited

U.S. PATENT DOCUMENTS

| | | |
|---|---|---|
| 2004/0152699 A1 | 8/2004 | Arora et al. |
| 2004/0157881 A1 | 8/2004 | Maekawa et al. |
| 2005/0272779 A1 | 12/2005 | Edwards et al. |
| 2006/0063772 A1 | 3/2006 | Arora et al. |
| 2007/0010562 A1 | 1/2007 | Bauer et al. |
| 2008/0032990 A1 | 2/2008 | Khalifah et al. |
| 2008/0114044 A1 | 5/2008 | Epple et al. |
| 2008/0182837 A1 | 7/2008 | Steurer et al. |
| 2008/0194634 A1 | 8/2008 | Arndt et al. |
| 2008/0207910 A1 | 8/2008 | Podhorez et al. |
| 2009/0074717 A1 | 3/2009 | Leivers et al. |
| 2009/0076103 A1 | 3/2009 | Olson et al. |
| 2009/0105251 A1 | 4/2009 | Jones et al. |
| 2009/0143451 A1 | 6/2009 | Andrews et al. |
| 2009/0197880 A1 | 8/2009 | Leivers et al. |
| 2009/0286782 A1 | 11/2009 | Ibrahim et al. |
| 2009/0286806 A1 | 11/2009 | Pajouhesh et al. |
| 2009/0306086 A1 | 12/2009 | Ibrahim et al. |
| 2010/0016313 A1 | 1/2010 | Millan et al. |
| 2010/0029655 A1 | 2/2010 | Leivers et al. |
| 2010/0048910 A1 | 2/2010 | Godschalx et al. |
| 2010/0093751 A1 | 4/2010 | Hynd et al. |
| 2010/0184809 A1 | 7/2010 | Kremoser et al. |
| 2010/0197662 A1 | 8/2010 | Ogawa et al. |
| 2010/0210660 A1 | 8/2010 | Kremoser et al. |
| 2010/0216827 A1 | 8/2010 | Ma et al. |
| 2010/0234347 A1 | 9/2010 | Dollinger et al. |
| 2010/0240657 A1 | 9/2010 | Sapountzis et al. |
| 2010/0256145 A1 | 10/2010 | Bak-Jensen et al. |
| 2011/0044943 A1 | 2/2011 | Leivers et al. |
| 2011/0212975 A1 | 9/2011 | Kao et al. |
| 2011/0220880 A1 | 9/2011 | Cheng et al. |
| 2011/0257196 A1 | 10/2011 | Lu et al. |
| 2011/0306493 A1 | 12/2011 | Paulini et al. |
| 2011/0312950 A1 | 12/2011 | Eckhardt et al. |
| 2012/0015988 A1 | 1/2012 | Hickey et al. |
| 2012/0021519 A1 | 1/2012 | Ichida et al. |
| 2012/0022067 A1 | 1/2012 | Chen et al. |
| 2012/0029027 A1 | 2/2012 | Estenne-Bouhtou et al. |
| 2012/0071524 A1 | 3/2012 | Lu et al. |
| 2012/0110705 A1 | 5/2012 | Le Vezouet et al. |
| 2012/0122681 A1 | 5/2012 | Le Vezouet et al. |
| 2012/0220603 A1 | 8/2012 | Pajouhesh et al. |
| 2012/0232116 A1 | 9/2012 | Kremoser et al. |
| 2012/0245166 A1 | 9/2012 | Grimaldi et al. |
| 2013/0231348 A1 | 9/2013 | Campbell et al. |
| 2013/0261108 A1 | 10/2013 | Tully et al. |
| 2013/0281503 A1 | 10/2013 | Melander et al. |
| 2014/0039007 A1 | 2/2014 | Tully et al. |
| 2014/0249100 A1 | 9/2014 | Shalwitz et al. |
| 2015/0082981 A1 | 3/2015 | Shiflett |
| 2015/0291572 A1 | 10/2015 | Schunk et al. |
| 2016/0376279 A1 | 12/2016 | Evans et al. |
| 2017/0073635 A1 | 3/2017 | Zhang |
| 2017/0204073 A1 | 7/2017 | Almstead et al. |
| 2017/0204096 A1 | 7/2017 | Gelin et al. |
| 2017/0279055 A1 | 9/2017 | Jang et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0368038 A1 | 12/2017 | Badman et al. |
| 2018/0009754 A1 | 1/2018 | Long et al. |
| 2018/0030003 A1 | 2/2018 | Wang et al. |
| 2018/0051258 A1 | 2/2018 | Zhang et al. |
| 2018/0099957 A1 | 4/2018 | Ma et al. |
| 2018/0123052 A1 | 5/2018 | Zysman-Colman et al. |

FOREIGN PATENT DOCUMENTS

| | | |
|---|---|---|
| CN | 104513213 A | 4/2015 |
| CN | 106146483 A | 11/2016 |
| CN | 106588804 A | 4/2017 |
| CN | 106632294 A | 5/2017 |
| CN | 106748922 A | 5/2017 |
| CN | 107021957 A | 8/2017 |
| CN | 107021958 A | 8/2017 |
| EP | 1894924 A1 | 3/2008 |
| JP | 2008308448 A | 12/2008 |
| WO | WO-9417059 A1 | 8/1994 |
| WO | WO-9424095 A1 | 10/1994 |
| WO | WO-9712883 A1 | 4/1997 |
| WO | WO-0037077 A1 | 6/2000 |
| WO | WO-0077011 A1 | 12/2000 |
| WO | WO-03015771 A1 | 2/2003 |
| WO | WO-03015777 A1 | 2/2003 |
| WO | WO-03016280 A1 | 2/2003 |
| WO | WO-03016288 A1 | 2/2003 |
| WO | WO-03080803 A2 | 10/2003 |
| WO | WO-2004024162 A1 | 3/2004 |
| WO | WO-2004045511 A2 | 6/2004 |
| WO | WO-2004046068 A2 | 6/2004 |
| WO | WO-2004046162 A2 | 6/2004 |
| WO | WO-2004048349 A1 | 6/2004 |
| WO | WO-2004087076 A2 | 10/2004 |
| WO | WO-2005056554 A2 | 6/2005 |
| WO | WO-05077373 A2 | 8/2005 |
| WO | WO-2005077345 A1 | 8/2005 |
| WO | WO-2005123731 A2 | 12/2005 |
| WO | WO-2006101052 A1 | 9/2006 |
| WO | WO-2007070796 A1 | 6/2007 |
| WO | WO-2007076260 A2 | 7/2007 |
| WO | WO-2007092751 A2 | 8/2007 |
| WO | WO-2007095174 A2 | 8/2007 |
| WO | WO-2007140174 A2 | 12/2007 |
| WO | WO-2007140183 A1 | 12/2007 |
| WO | WO-2008002573 A2 | 1/2008 |
| WO | WO-2008025539 A1 | 3/2008 |
| WO | WO-2008025540 A1 | 3/2008 |
| WO | WO-2008051942 A2 | 5/2008 |
| WO | WO-2008073825 A1 | 6/2008 |
| WO | WO-2008097235 A1 | 8/2008 |
| WO | WO-2008155054 A1 | 12/2008 |
| WO | WO-2008157270 A1 | 12/2008 |
| WO | WO-2009005998 A1 | 1/2009 |
| WO | WO-2009012125 A1 | 1/2009 |
| WO | WO-2009127321 A1 | 10/2009 |
| WO | WO-2009149795 A2 | 12/2009 |
| WO | WO-2010034649 A1 | 4/2010 |
| WO | WO-2010034657 A1 | 4/2010 |
| WO | WO-2010036362 A1 | 4/2010 |
| WO | WO-2010093191 A2 | 8/2010 |
| WO | WO-2011020615 A1 | 2/2011 |
| WO | WO-2011109059 A1 | 9/2011 |
| WO | WO-2012087519 A1 | 6/2012 |
| WO | WO-2012087521 A1 | 6/2012 |
| WO | WO-2013007387 A1 | 1/2013 |
| WO | WO-2013037482 A1 | 3/2013 |
| WO | WO-2013192097 A1 | 12/2013 |
| WO | WO-2014181287 A1 | 11/2014 |
| WO | WO-2014184271 A1 | 11/2014 |
| WO | WO-2015017813 A2 | 2/2015 |
| WO | WO-2015036442 A1 | 3/2015 |
| WO | WO-2015065983 A1 | 5/2015 |
| WO | WO-2015069666 A1 | 5/2015 |
| WO | WO-2015116856 A2 | 8/2015 |
| WO | WO-2015138969 A1 | 9/2015 |
| WO | WO-2015138986 A1 | 9/2015 |
| WO | WO-2015162244 A1 | 10/2015 |
| WO | WO-2015162538 A1 | 10/2015 |
| WO | WO-2015165960 A1 | 11/2015 |
| WO | WO-2015181275 A1 | 12/2015 |
| WO | WO-2016055441 A1 | 4/2016 |
| WO | WO-2016073767 A1 | 5/2016 |
| WO | WO-2016081918 A1 | 5/2016 |
| WO | WO-2016086115 A1 | 6/2016 |
| WO | WO-2016086134 A1 | 6/2016 |

(56) References Cited

FOREIGN PATENT DOCUMENTS

| | | |
|---|---|---|
| WO | WO-2016086169 A1 | 6/2016 |
| WO | WO-2016086218 A1 | 6/2016 |
| WO | WO-2016096115 A1 | 6/2016 |
| WO | WO-2016096116 A1 | 6/2016 |
| WO | WO-2016112305 A1 | 7/2016 |
| WO | WO-2017011466 A1 | 1/2017 |
| WO | WO-2017096130 A1 | 6/2017 |
| WO | WO-2017097870 A1 | 6/2017 |
| WO | WO-2017117687 A1 | 7/2017 |
| WO | WO-2017118294 A1 | 7/2017 |
| WO | WO-2017118762 A1 | 7/2017 |
| WO | WO-2017122209 A2 | 7/2017 |
| WO | WO-2017128896 A1 | 8/2017 |
| WO | WO-2017133521 A1 | 8/2017 |
| WO | WO-2017147047 A1 | 8/2017 |
| WO | WO-2017162211 A1 | 9/2017 |
| WO | WO-2017210526 A1 | 12/2017 |
| WO | WO-2018024224 A1 | 2/2018 |
| WO | WO-2018039384 A1 | 3/2018 |
| WO | WO-2018039386 A1 | 3/2018 |
| WO | WO-2018059314 A1 | 4/2018 |
| WO | WO-2018060075 A1 | 4/2018 |
| WO | WO-2018075207 A1 | 4/2018 |
| WO | WO-2018087599 A1 | 5/2018 |
| WO | WO-2018089212 A1 | 5/2018 |

OTHER PUBLICATIONS

Akwabi-Ameyaw, et al., (2009) "FXR agonist activity of conformationally constrained analogs of GW 4064" Bioorganic & Medicinal Chemistry Letters 19: 4733-4739.
Alasmael, et al., (2014) "The regulatory role of Farnesoid X Receptor on Matrix Metalloproteinases-2 and -9 in advanced Breast Cancer the European Association for Cancer" Research Conference Series on Goodbye Flat Biology: 3D Models and the Tumour Microenvironment (Abstract).
Ali et al., (2014) "Recent advances in the development of farnesoid X receptor agonists" Annals of Translational Medicine 3(1): 1-16.
Alrashid, et al,. (2007) "FXR plays a key role in the antiproliferative and apoptotic responses of bile acids in coloncarcinoma cell lines" 98th Annual Meeting of the American Association for Cancer Research, (Abstract).
Alvarez et al., "Reduced hepatic expression of farnesoid X receptor in hereditary cholestasis associated to mutation in ATP8B1," Human Molecular Genetics,13(20): 2451-2460, 2004.
Ananthanarayanan et al., "Human Bile Salt Export Pump Promoter is Transactivated by the Farnesoid X Receptor/Bile Acid Receptor," The Journal of Biological Chemistry, 276(31): 28857-28865, Aug. 3, 2001.
Andreone, et al., (2014) "The FXR Agonist Obeticholic Acid (OCA) Improves Liver Biochemistry Parameters Correlated With Clinical Benefit Across a Range of Patient Characteristics" 65th Annual Meeting and Postgraduate Course of the American Association for the Study of Liver Diseases (AASLD) (Abstract).
Aparecida, et al., (2012) "Alcoholic liver steatosis in mice is aggravated by low-protein diet and reversed by FXR agonist" 1st Conference on Metabolism, Diet and Disease (Abstract).
Aranda et al., "Nuclear Hormone Receptors and Gene Expression," Physiological Reviews 81(3): 1269-1304, Jul. 2001.
Auwerx (2006) "Turning Up the Heat with Bile Acids" Nuclear Receptors: Steroid Sisters (X4) (Abstract).
Baghdasaryan, et al., (2010) "Therapeutic Effects of FXR and TGR5 Activation in the MDR2 (ABCB4)OUSE Modelof Sclerosing Cholangitis" 45th Annual Meeting of the European Association for the Study of the Liver (EASL) (Abstract).
Baghdasaryan, et al., (2010) "Therapeutic Targeting of Nuclear and Membrane Bile Acid Receptors in a Mouse Model of Chronic Cholestasis" 61st Annual Meeting of the American Association for the Study of Liver Diseases (AASLD) (Abstract).
Baghdasaryan, et al., (2011) "FXR but not Tgr5 activation stimulates HCO3—rich bile secretion and ameliorates liver damage in Mdr2−/− (Abcb4−/−) mouse model of chronic liver injury" 62nd Annual Meeting of the American Association for the Study of Liver Diseases (AASLD) (Abstract).
Balasubramaniyan, et al., (2005) "Human Organic Solute Transporter Alpha (Ost-Alpha) is Transactivated by FXR , HNF-4 Alpha and FTF/LRH-1: Implications for Basolateral Bile Acid Transport in Human Liver" 56th Annual Meeting of the American Association for the Study of Liver Diseases (AASLD) (Abstract).
Ballatori, et al., (2010) "Ost alpha-Ost beta: A key membrane transporter of bile acids and conjugated steroids" Front Biosci 14: 2829-2844.
Bart, et al., (2004) "Perspective targets in the treatment of the metabolic syndrome" 13th European Congress on Obesity (European Association for the Study of Obesity (Abstract).
Bass, et al., (2011) "Conformationally constrained farnesoid X receptor (FXR) agonists: Heteroaryl replacements of the naphthalene" Bioorganic & Medicinal Chemistry Letters 21: 1206-1213.
Bechmann, et al., (2011) "Free fatty acids repress SHP activation and adiponectin counteracts bile acid induced liver injury:new target options for NASH treatment?" 62nd Annual Meeting of the American Association for the Study of Liver Diseases (AASLD) (Abstract).
Beth, et al., "Soy Lipid-Derived Phytosterols are FXR Antagonists—Potential Role in Total Parenteral Nutrition-Associated Cholestasis (TPNAC)" Digestive Disease Week 2004: American Association for the Study of Liver Diseases, American Gastroenterological Association, American Society for Gastrointestinal Endoscopy, Society for Surgery of the Alimentary Tract (Abstract).
Beuers, et al., (2014) "FXR Agonist Obeticholic Acid: Pruritus, A Common Side Effect Ameliorated by Dose Titration" 65th Annual Meeting and Postgraduate Course of the American Association for the Study of Liver Diseases (AASLD) (Abstract).
Bianchi, et al., (2011) "Farnesoid-X-receptor (FXR) agonist INT-747 restores hepatic DDAH activity after ischemia/reperfusion injury" 35° Congresso Nazionale della Società Italiana di Farmacologia (SIF) / 35th National Congress of the Italian Society of Pharmacology (Abstract).
Bilz et al., "Activation of the farnesoid X receptor improves lipid metabolism in combined hyperlipidemic hamsters," Am. J. Physiol. Endocrinol. Metab., 290(4) E716-722, 2006, doi: 10.1152/aipendo. 00355.2005.
Boesjes, et al., (2014) "Hepatic Farnesoid X-Receptor Isoforms a2 and a4 Differentially Modulate Bile Salt and Lipoprotein Metabolism in Mice" PLOS One 9: 1-19.
Bowlus, et al., (2014) "Obeticholic Acid in PBC Patients: The Utility of Titration Based on Therapeutic Response and Tolerability" 65th Annual Meeting and Postgraduate Course of the American Association for the Study of Liver Diseases (AASLD) (Abstract).
Brzozowski et al., "Molecular basis of agonism and antagonism in the oestrogen receptor," Nature, 389:753-758, Oct. 16, 1997.
Buttar, et al., (2007) "Role of Farnesoid-X-receptor in Esophageal Carcinogenesis" Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Cai et al., "FXR: a target for cholestatic syndromes?" Expert Opin. Ther. Targets, 10(3): 409-421, 2006.
Cariou et al., "The Farnesoid X Receptor Modulates Adiposity and Peripheral Insulin Sensitivity in Mice," The Journal of Biological Chemistry, 28, 11039-11049, Apr. 21, 2006.
Cariou, et al., (2005) "Farnesoid X Receptor (FXR) regulates peripheral insulin sensitivity" 41st Annual Meeting of the European Association for the Study of Diabetes (EASD) (Abstract).
Carotti, et al., (2014) "Beyond Bile Acids: Targeting Farnesoid X Receptor (FXR) with Natural and Synthetic Ligands" Current Topics in Medicinal Chemistry 14: 2129-2142.
Cha, et al., (2009) "Farnesoid X Receptor (FXR) Agonist Improves Insulin Resistance and Ameliorates Diabetic Nephropathy in db/db Mice" 42nd Annual Meeting and Exposition of the American Society of Nephrology (ASN) (Abstract).

(56) References Cited

OTHER PUBLICATIONS

Changming, et al., (2009) "Ileal bile acid binding protein mediates the chemopreventative effect of ursodeoxycholic acid by activating nuclear receptor FXR in colorectal cancer cells" 100th Annual Meeting of the American Association for Cancer Research (AACR) (Abstract).
Chen et al., "Progressive Familial Intrahepatic Cholestasis. Type I, Is Associated With Decreased Farnesoid X Receptor Activity," Gastroenterology, 126, 756-764, Mar. 2004.
Cheng, et al., (2011) "Farnesoid X Receptor (FXR) controls expression of Fibroblast Growth Factor 21 (FGF21) in liver cells" 4th International Congress on Prediabetes and the Metabolic Syndrome (Abstract).
Chennamsetty, et al., (2010) "Role of Farnesoid X Receptor Agonists in the In Vivo and In Vitro Expression of Apolipoprotein(A)" 78th European Atherosclerosis Society Congress (EAS) (Abstract).
Chiang, et al., (2004) "Mechanisms of bile acid inhibition of genes in bile acid synthesis" Falk Symposium No. 141 Bile Acids and Cholesterol Metabolism and its Therapeutical Implications (Abstract).
Chignard, et al., (2003) "The VILP Receptor VPAC-1 in Highly Expressed and Regulated by FXR and RXR Alpha Nuclear Receptors in the Human Gallbladder Epithelifum" 54th Annual Meeting of the American Association for the Study of Liver Diseases (AASLD) (Abstract).
Cho, et al., (2011) "Guggulsterone Inhibits LXRa Mediated SREBP-1C-Dependent Hepatic Steatosis Through PKC Dependent Pathway" 46th Annual Meeting of the European Association for the Study of the Liver (EASL) (Abstract).
Chouinard, et al., (2007) "Bile Acid 7a-Hydroxylase and 12s-Hydroxylase Indices Convey Target Pharmacology, Predict Preclinical Endpoint Efficacy and Offer Utility as Clinical Translational Markers of FXR Agonist Activity" Nuclear Receptors and Metabolism (Z1) held jointly with Metabolic Syndrome and Cardiovascular Risk (Z2) (Abstract).
Chu, et al., (2013) "Bile Acids Induce COX-2 Expression in Human Esophagus via Activation of Farnesoid X Receptor (FXR) and Nf?B" 54th Annual Meeting at Digestive Disease Week (DDW 2013 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Claudel et al., "The Farnesoid X Receptor: A Molecular Link Between Bile Acid and Lipid and Glucose Metabolism," Arteriosclerosis, Thrombosis, and Vascular Biology, 25,2020-2031, 2005, obtained from URL=http://atvb.ahaioumals.org, download date Jan. 19, 2012.
Claudel, et al., (2005) "Constitutive Androstane Receptor Negatively Regulates Human Apolipoprotein A-1 Expression" 78th Annual Scientific Sessions of the American Heart Association (AHA) (Abstract).
Cortés, et al., (2005) "Recombinant Adenovirus-Mediated Functional Expression and Heterodimeric Nuclear Receptor-Dependent Regulation of Syndecan-1 in the Murine Liver: Implications in Cholesterol Metabolism" Digestive Disease Week 2005 (DDW): American Association for the Study of Liver Diseases, American Gastroenterological Association, American Society for Gastrointestinal Endoscopy, Society for Surgery of the Alimentary Tract (Abstract).
D'Amore, et al., (2014) "Design, Synthesis, and Biological Evaluation of Potent Dual Agonists of Nuclear and Membrane Bile Acid Receptors" Journal of Medicinal Chemistry 57: 937-954.
Das, et al., (2007) "Farnesoid X Receptor Dependent Regulation of MMP9 in Blood Outgrowth Endothelial Cells Contributes to Cell Migration and Homing Through a Pathway involving SHP and KLF repressor proteins" Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Das, et al., (2007) "FXR bile acid receptor activates focal adhesion kinase and stress fiber-mediated motility in endothelial cells" 58th Annual Meeting of the American Association for the Study of Liver Diseases (AASLD) (Abstract).
Das, et al., (2009) "FXR Promotes Endothelial Cell Motility through Reciprocal Regulation of FAK and MMP-9" 2009 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), and the American Society for Pharmacology and Experimental Therapeutics (ASPET) (Abstract).
De Oliveira, et al., (2012) "Bile acid receptor agonists INT-747 and INT-777 decrease estrogen deficiency-related postmenopausal obesity and hepatic steatosis" 63rd Annual Meeting and Postgraduate Course of the American Association for the Study of Liver Diseases (AASLD) (Abstract).
Demars, et al., (2005) "Farnesoid-X-receptor and carcinogenesis in Barrett's esophagus" 96th American Association for Cancer Research Annual Meeting (Abstract).
Deuschle, et al., (2012) "FXR Directly Controls the Tumor Suppressor NDRG2 and FXR Agonists Reduce Tumor Growth and Metastasis in an Orthotopic Xenograft Mouse Model" 47th Annual Meeting of the European Association for the Study of the Liver (EASL) (Abstract).
Deuschle, et al., (2014) "The nuclear bile acid receptor FXR controls the liver derived tumor suppressor histidine-rich glycoprotein" International Journal of Cancer 00: 00-00.
Dodson, et al., (2005) "Concerted Control of Lipids and Insulin Sensitization by FXR" 87th Annual Meeting of the Endocrine Society (ENDO) (Abstract).
Dodson, et al., (2007) "Concerted control of insulin sensitization through lipid and carbohydrate metabolism by FXR" Nuclear Receptors and Metabolism (Z1) held jointly with Metabolic Syndrome and Cardiovascular Risk (Z2) (Abstract).
Doggrell, "New targets in and potential treatments for cholesterol gallstone disease," Current Opinion in Investigational Drugs 7(4): 344-348, 2006.
Dossa, et al., (2014) "Bile Acids Differentially Control Intestinal Cell Proliferation via Src Kinase" 2014 Clinical Congress of the American College of Surgeons (ACS) (Abstract).
Dossa, et al., (2014) "Intestinal Bile Acids Differentially Control Intestinal Cell Proliferation" 34th Annual Meeting of the Surgical Infection Society (SIS) (Abstract).
Duran-Sandoval et al., "Potential regulatory role of the famesoid X receptor in the metabolic syndrome," Biochimie 87:93-98, 2005.
Edwards, et al., (2007) "FXR Modulates Lipid and Glucose Metabolism" Nuclear Receptors and Metabolism (Z1) held jointly with Metabolic Syndrome and Cardiovascular Risk (Z2) (Abstract).
Eloranta, et al., (2004) "Coordinate transcriptional regulation of bile acid homeostasis and drug metabolism" Archives of Biochemistry and Biophysics 433: 397-412.
Eloranta, et al., (2005) "Human Organic Solute Transporter-alpha (OSTalpha) and -beta (OSTbeta) Genes are Transactivated by the Nuclear Bile Acid Receptor/Farnesoid X Receptor (FXR)" 56th Annual Meeting of the American Association for the Study of Liver Diseases (AASLD) (Abstract).
European Search Report for EP11005722, completed Sep. 13, 2011.
European Search Report for EP15002478.4, completed Nov. 17, 2015.
Evans, "The Nuclear Receptor Superfamily: A Rosetta Stone for Physiology," Molecular Endocrinology 19(6): 1429-1438, Jun. 2005.
Evans, et al., (2007) "Activation of Farnesoid X Receptor (FXR) in the treatment of dyslipidemia" Nuclear Receptors and Metabolism (Z1) held jointly with Metabolic Syndrome and Cardiovascular Risk (Z2) (Abstract).
Evans, et al., (2007) "Activation of Farnesoid X Receptor (FXR) Protects Against Diet-Induced Dyslipidemia" 76th European Atherosclerosis Society Congress (EAS) (Abstract).
Falk, et al., (2006) "Primary biliary cirrhosis: From ursodeoxycholic acid towards targeting strategies for therapy" Falk Symposium No.

(56) References Cited

OTHER PUBLICATIONS

155: XIX International Bile Acid Meeting—Bile Acids: Biological Actions and Clinical Relevance (Abstract).
Fang, et al., (2008) "The acetylase p300 and deacetylase SIRT1 are critical in vivo FXR cofactors in regulation of liver metabolism" 2008 Nuclear Receptors: Orphan Brothers (Z1) (Abstract).
Feng, et al., (2009) "Identification of an N-oxide pyridine GW4064 analog as a potent FXR agonist" Bioorganic & Medicinal Chemistry Letters 19: 2595-2598.
Figge et al., "Hepatic Overexpression of Murine Abcb11 Increases Hepatobiliary Lipid Secretion and Reduces Hepatic Steatosis," The Journal of Biological Chemistry 279(4): 2790-2799, Jan. 23, 2004.
Fiorucci et al., "Protective Effects of 6-Ethyl Chenodeoxycholic Acid, a Farnesoid X Receptor Ligand, in Estrogen-Induced Cholestasis," The Journal of Pharmacology and Experimental Therapeutics 313(2): 604-612,2005.
Fiorucci et al., "The Nuclear Receptor SHP Mediates Inhibition of Hepatic Stellate Cells by FXR and Protects Against Liver Fibrosis," Gastroenterology 127(5): 1497-1512, Nov. 2004.
Fiorucci, et al., (2003) "The FXR-agonist, 6-Ethyl-Chenodeoxycholic Acid (6-ECDCA), protects against estrogen-induced cholestasis in rats" Pellicciari R Digestive Disease Week 2003 (DDW): American Association for the Study of Liver Diseases, American astroenterological Association, American Society for Gastrointestinal Endoscopy, Society for Surgery of the Alimentary Tract (Abstract).
Fiorucci, et al., (2005), "A Famesoid X Receptor-Small Heterodimer Partner Regulatory Cascade Modulates Tissue Metalloproteinase Inhibitor-1 and Matrix Metalloprotease Expression in Hepatic Stellate Cells and Promotes Resolution of Liver Fibrosis", TheJournal of Pharmacology and Experimental Therapeutics, 314: 584-595.
Fiorucci, et al., (2010) "The Bile Acid Sensor FXR Modulates Hydrogen Sulfide Generation in the Gastric Mucosa and Protects Against Injury Caused by Aspirin" Digestive Disease Week 2010 (DDW) (Abstract).
Fiorucci, et al., (2014) "Targeting FXR in cholestasis: hype or hope" Expert Opinion 18 (12).
Flatt, et al., (2005) "SAR of highly potent full-range modulators of the farnesoid X receptor" 229th National Meeting of the American Chemical Society (Abstract).
Flesch, et al., (2014) "Screening, synthesis and characterization of novel ligands for Farnesoid X Receptor (FXR)" 2014 Annual Meeting on Trends and Perspectives in Pharmaceutical Sciences (DPhG ) Annual Meeting of the German Pharmaceutical Society (DPhG) (Abstract).
Flesch, et al., (2014) "Screening, Synthesis and Characterization of Novel Ligands for Farnesoid X Receptor (FXR)" 23rd International Symposium on Medicinal Chemistry (ISMC) held Jointly with the European Federation for Medicinal Chemistry (EFMC) (Abstract).
Flesch, et al., (2015) "Fragmentation of GW4064 led to a highly potent partial Farnesoid X Receptor agonist with improved druglike properties" Bioorganic & Medicinal Chemistry 13: 3490-8.
Forman et al., "Identification of a Nuclear Receptor That is Activated by Farnesol Metabolites," Cell 81:687-693, Jun. 2, 1995.
Fuchs, et al., (2012) "Changes in hepatic bile acid composition protect BSEP (ABCB11) KO mice from hepatic inflammation in methionine choline deficient (MCD)-diet induced NASH" 63rd Annual Meeting and Postgraduate Course of the American Association for the Study of Liver Diseases (AASLD) (Abstract).
Fuchs, et al., (2012) "FXR is a Key Player in NAFLD Development by Controlling CHOP Expression" 47th Annual Meeting of the European Association for the Study of the Liver (EASL) (Abstract).
Fuchs, et al., (2013) "FXR controlled CHOP as novel key player in NAFLD progression" 64th Annual Meeting and Postgraduate Course of the American Association for the Study of Liver Diseases (AASLD) (Abstract).
Fuchs, et al., (2014) "Intrahepatic Changes in Bile Acid Composition Protects Bsep (ABCB11) KO Mice From Hepatic Injury in Methionine Choline-Deficient Diet Induced NASH" 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Gadaleta, et al., (2009) "FXR activation represses TNFa-induced NF-?B signalling" 2009 Spring Meeting of the Dutch Society for Gastroenterology/2009 Voorjaarsvergadering Nederlandse Vereniging voor Gastroenterologie (Abstract).
Gadaleta, et al., (2010) "Intestinal Bile Salt Nuclear Receptor FXR Protects From Inflammatory Bowel Disease: Potential Therapeutic Implications" Digestive Disease Week 2010 (DDW) (Abstract).
Gadaleta, et al., (2011) "Farnesoid X receptor activation inhibits inflammation and preserves the intestinal barrier in inflammatory bowel disease" Inflammatory bowel disease 60: 463-472.
Gautier, et al., (2011) "Farnesoid X Receptor Activation Induces Cholesteryl Ester Transfer Protein Expression in Humans and Transgenic Mice" 12th Annual Conference on Arteriosclerosis, Thrombosis and Vascular Biology (ATVB) in collaboration with the Council on Peripheral Vascular Disease (Abstract).
Gautier, et al., (2011) "Farnesoid X Receptor Activation Induces Cholesteryl Ester Transfer Protein Expression in Humans and Transgenic Mice" 79th European Atherosclerosis Society Congress (EAS) (Abstract).
Gege, et al., (2014) "Knocking on FXR's Door: The "Hammerhead"-Structure Series of FXR Agonists-Amphiphilic Isoxazoles with Potent In Vitro and In Vivo Activities" Current Topics in Medicinal Chemistry 14: 1-16.
Gioiello, et al., (2014) "Bile Acid Derivatives as Ligands of the Farnesoid X Receptor: Molecular Determinants for Bile Acid Binding and Receptor Modulation" Current Topics in Medicinal Chemistry 14: 2159-2174.
Giordano, et al., (2010) "Activated Farnesoid X Receptor Inhibits Growth of Tamoxif en-Resistant MCF-7 Breast Cancer Cells, through Down-Regulation of HER2 Expression" 92nd Annual Meeting of the Endocrine Society (ENDO) (Abstract).
Giordano, et al., (2010) "Activated Farnesoid X Receptor inhibits growth of tamoxifen-resistant breast cancer cells" 2010 Experimental Biology Annual Meeting (FASEB) held jointly with the the American Association of Anatomists (AAA), The American Physiological Society (APS), American Society for Biochemistry and Molecular Biology (ASBMB), American Society for Investigative Pathology (ASIP), American Society for Nutrition (ASN) and the American Society for Pharmacology and Experimental Therapeutics (ASPET) (Abstract).
Giordano, et al., (2014) "FXR Ligands, by Interfering with Tumor/ Microenvironment Crosstalk, Inhibit Breast Tumor Growth and Progression" 2nd Joint Meeting of Pathology and Laboratory Diagnostics, 32.Congress of the Società Italiana di Patologia e Medicina Traslazionale, 64.National Congress of the Associazione Italiana di Patologia Clinica e Medicina Molecolare/32nd Congress of the Italian Society of Pathology and Translational Medicine and 64th National Congress of the Italian Association of Clinical Pathology and Molecular Medicine (Abstract).
Glastras, et al., (2013) "The role of FXR in maternal obesity related renal injury in mother and offspring" 2013 Annual Scientific Meeting of the Australian Diabetes Educators Association (ADEA) and the Australian Diabetes Society (ADS) (Abstract).
Gnerre, et al., (2004) "CYP3A4 and CYP3A11 are Regulated by the Nuclear Receptor FXR and Primary Bile Acids in Cell Cultures and in Mice" 15th International Symposium on Microsomes and Drug Oxidations: Chemical Biology in the Postgenomic Era—New Approaches and Applications (Abstract).
Goodwin et al., "A Regulatory Cascade of the Nuclear Receptors FXR, SHP-1, and LRH-I Represses Bile Acid Biosynthesis," Molecular Cell 6: 517-526, Sep. 2000.
Grefhorst, et al., (2004) "The role of nuclear hormone receptors in hepatic insulin resistance" 3rd Dutch Endo-Neuro-Psycho Meeting 2004 (Abstract).
Guan, et al., (2008) "Nuclear receptors and metabolic syndrome" 2008 Beijing Conference of Physiological Sciences jointly supported by the American Physiological Society, Australian Physiological Society, Canadian Physiological Society, Chinese Association for Physiological Sciences, and the Physiological Society (UK) (Abstract).

(56) References Cited

OTHER PUBLICATIONS

Guo-Ning, et al., (2014) "Synthesis and Bioactivity of Chalcones and Related Compounds as Farnesoid X Receptor (FXR) Antagonists" 34th National Medicinal Chemistry Symposium (NMCS) (Abstract).

Habegger, et al., (2012) "Fibroblast Growth Factor 21 and Farnesoid X Receptor Mediate Chronic Glucagon Action" 72nd Annual Meeting and Scientific Sessions of the American Diabetes Association (ADA) (Abstract).

Hambruch, et al, (2013) "FXR agonist Px-102 improves hepatic steatosis in NAFLD mouse models" Phenex (Poster).

Hambruch, et al., (2012) "Synthetic Farnesoid X Receptor agonist PX20606 demonstrates anti-atherosclerotic effects and lowers cholesterol in HDL2 but not in HDL3 subfractions" Poster.

Hambruch, et al., (2013) "FXR Agonist Px-102 Improves Hepatic Steatosis in NAFLD Rodent Models" 23rd Conference of the Asia Pacific Associaton for the Study of the Liver (APASL 2013): Transforming Science to Clinical Practice (Abstract).

Hanniman et al., "Loss of functional farnesoid X receptor increases atherosclerotic lesions in apolipoprotein E-deficient mice," Journal of Lipid Research, 46:2595-2604, 2005.

Hansen, et al., (2014) "The FXR Agonist Obeticholic Acid Improves Alkaline Phospatase/Bilirubin Response Criterion Associated With Transplant-Free Survival in Primary Biliary Cirrhosis" 2014 European Association for the Study of the Liver (EASL) Monothematic Conference: Primary Biliary Cirrhosis (PBC) (Abstract).

Harnish, (2007) "A Synthetic Farnesoid X Receptor Agonist Protects Against Diet-Induced Dyslipidemia" 80th Annual Scientific Sessions of the American Heart Association (AHA) (Abstract).

Harnish, et al., (2007) "A Synthetic Farnesoid X Receptor (FXR) Agonist Protects Against Diet-Induced Dyslipidemia" 16th International Symposium on Drugs Affecting Lipid Metabolism (Abstract).

Harnish, et al., (2007) "The Farnesoid X Receptor (FXR) Antagonizes Oxidized LDL Receptor, LOX-1, Activation" 80th Annual Scientific Sessions of the American Heart Association (AHA) (Abstract).

Hartman, et al., (2007) "Farnesoid X Receptor (FXR) Regulates RECK Expression" 58th Annual Meeting of the American Association for the Study of Liver Diseases (AASLD) (Abstract).

Hawksworth, (2010) "Hepatic transporters—Regulation, induction and potential for drug-drug interactions" 8th Southeast European Congress on Xenobiotic Metabolism and Toxicity (XEMET 2010) (Abstract).

He et al., "Downregulation of Endothelin-1 by Farnesoid X Receptor in Vascular Endothelial Cells," Circulation Research 98(2): 192-199,2006, plus online supplement, obtained from URL=http://circres.ahaioumals.org, download date Jun. 11, 2012, 14pages.

Heery et al., "A signature motif in transcriptional co-activators mediates binding to nuclear receptors," Nature 387:733-736, Jun. 12, 1997.

Heinzel et al., "A complex containing N-CoR, mSin3 and histone deacetylase mediates transcriptional repression," Nature, 387:43-48, May 1, 1997.

Henry, et al., (2009) "Farnesoid X ReceptorAgonists: A New Therapeutic Class for Diabetes and Fatty Liver Disease? The First FXR Therapeutic Study in Diabetes" 69th Annual Meeting and Scientific Sessions of the American Diabetes Association (ADA) (Abstract).

Hirschfield, et al., (2014) "Efficacy of Obeticholic Acid in Patients with Primary Biliary Cirrhosis and Inadequate Response to Ursodeoxycholic Acid" Gastroenterology 148: 751-761.

Hoegenauer, et al., (2014) "G-Protein-coupled Bile Acid Receptor 1 (GPBAR1,TGR5) agonists reduce the production of proinflammatory cytokines and stabilize the 57alternative macrophage phenotype" Journal of Medicinal Chemistry 57: 10343-54.

Holt et al., "Definition of a novel growth factor-dependent signal cascade for the suppression of bile acid biosynthesis," Genes & Development 17:1581-1591, 2003.

Horth, et al., (2009) "Influence of bile acids on stimulus-secretion coupling in pancreatic beta cells" Frühjahrstagung der Deutschen Gesellschaft für Experimentelle und Klinische Pharmakologie und Toxikologie/50th Spring Meeting of the German Society for Experimental and Clinical Pharmacology and Toxicology (Abstract).

Horth, et al., (2010) "The function of murine pancreatic beta cells is affected by bile acids" Frühjahrstagung der Deutschen Gesellschaft für Experimentelle und Klinische Pharmakologie und Toxikologie/51st Spring Meeting of the German Society for Experimental and Clinical Pharmacology and Toxicology (Abstract).

Horth, et al., (2011) "Bile acids affect the function of murine pancreatic beta cells" 47th Annual Meeting of the European Association for the Study of Diabetes (EASD) (Abstract).

Horth, et al., (2011) "Link between the nuclear farnesoid receptor and KATP channel activity in beta-cells" 90th Annual Meeting of the German Physiological Society/Deutsche Physiologische Gesellschaft (DPG) (Abstract).

Houssin, et al., (2010) "The FXR activators, chenodeoxycholic acid and GW4064 inhibit the proliferation of prostate cancer LNCaP and LAPC-4 cells" 2010 Nuclear Receptors: Signaling, Gene Regulation and Cancer (X7) (Abstract).

Howarth, et al., (2007) "Is the Farnesoid X Receptor in Japanese medaka (Oryzias latipes) a target for exogenous compounds?" 46th Annual Meeting of the Society of Toxicology (Abstract).

Hsu, et al., (2014) "Quantitative Profiling of Environmental Chemicals and Drugs for Farnesoid X Receptor Activity" 53rd Annual Meeting of the Society of Toxicology (SOT 2014) (Abstract).

Huang et al., "Farnesoid X Receptor Activates Transcription of the Phospholipid Pump MDR3," The Journal of Biological Chemistry 278(51): 51085-51090. Dec. 19, 2003.

Huang et al., "Nuclear Receptor-Dependent Bile Acid Signaling Is Required for Normal Liver Regeneration," Science 312:233-236, Apr. 14, 2006.

Huang, et al., (2014) "Recent Advances in Non-Steroidal FXR Antagonists Development for Therapeutic Applications" Current Topics in Medicinal Chemistry 14: 2175-2187.

Hulzebos, et al., (2005) "Pharmacological FXR Activation and the Enterohepatic Circulation of Bile Salts in Rats: Inhibition of Cholate Synthesis Rate and Reduced Cholate Pool Size" 115th Annual Meeting of the American Pediatric Society and 74th Annual Meeting of the Society for Pediatric Research together with the American Society of Pediatric Hematology/Oncology (ASPHO), the American Society of Pediatric Nephrology, the Lawson Wilkins Pediatric Endocrine Society and the Pediatric Infectious Disease Society (Abstract).

Hwang, et al., (2004) "The Cellular Distribution of FXR and RXRa Expression in Developing Rat Ileal Mucosa" Digestive Disease Week 2004 (DDW): American Association for the Study of Liver Diseases, American Gastroenterological Association, American Society for Gastrointestinal Endoscopy, Society for Surgery of the Alimentary Tract (Abstract).

Idelman, et al., (2012) "Activation of the farnesoid X-receptor (FXR) suppresses cyclin D1 expression and decreases proliferation of colon and breast cancer cells" 63rd Annual Meeting and Postgraduate Course of the American Association for the Study of Liver Diseases (AASLD) (Abstract).

Idelman, et al., (2014) "Activation of the farnesoid X-receptor suppresses cyclin D1 expression and decreases proliferation" 2014 Experimental Biology Annual Meeting (FASEB) held jointly with the the American Association of Anatomists (AAA), the American Physiological Society (APS), American Society for Biochemistry and Molecular Biology (ASBMB), American Society for Investigative Pathology (ASIP), American Society for Nutrition (ASN), Chinese Pharmacological Society (CPS) and the American Society for Pharmacology and Experimental Therapeutics (ASPET) (Abstract).

Ikpa. et al., (2014) "Impaired FXR Signaling in the CF Intestine" 28th Annual North American Cystic Fibrosis Conference (NACFC) (Abstract).

Inagaki et al., "Regulation of antibacterial defense in the small intestine by the nuclear bile acid receptor," Proc. Natl. Acad. Sci USA, 103, 3920-3905, 2006, doi:10.1073/pnas.0509592103.

Inagaki, et al., (2004) "Bile acid receptor, FXR, regulates host defense in intestine" 18th International Bile Acid Meeting: Bile Acid and Cholesterol Metabolism and its Therapeutic Implications (Abstract).

(56) References Cited

OTHER PUBLICATIONS

Inagaki, et al., (2004) "Bile acid receptor, FXR, regulates host defense in intestine" Falk Symposium No. 141 Bile Acids and Cholesterol Metabolism and its Therapeutical Implications (Abstract).
Inagaki, et al., (2006) "Regulation of Mucosal Defense in Intestine by the Nuclear Bile Acid Receptor" Nuclear Receptors: Orphan Brothers (X3) (Abstract).
Inagakj et al., "Fibroblast growth factor 15 functions as an enterohepatic signal to regulate bile acid homeostasis," Cell Metabolism, 2, 217-225, Oct. 2005.
Ishii, (2010) "Bile acids and their pathophysiological role in metabolic disorders" 83rd Annual Meeting of the Japanese Society for Pharmacology (Abstract).
Jae, et al., (2009) "Antidiabetic Effects of Novel Ligands for the Orphan Nuclear Receptor LRH-1" 2009 Type 2 Diabetes and Insulin Resistance (J3) (Abstract).
Jain, et al., (2009) "Enteral Bile Acids Improve TPN Related Cholestasis and Gut Mucosal Atrophy: Potential Role of FXR and FGF19" 22nd Annual Meeting of the North American Society for Pediatric Gastroenterology, Hepatology and Nutrition (NASPGHAN) (Abstract).
Jeong, et al., (2005) "Expression of All 48 Nuclear Hormone Receptors in Lung Cancer" Molecular Pathogenesis of Lung Cancer: Opportunities for Translation to the Clinic (Abstract).
Jiang, et al., (2006) "Protective Role of FXR Activation in Diabetic Nephropathy" 39th Annual Meeting and Exposition of the American Society of Nephrology (ASN): Renal Week 2006 (Abstract).
Jiang, et al., (2007) "FXR Modulates Renal Lipid Metabolism, Fibrosis, and Inflammation" 40th Annual Meeting and Exposition of the American Society of Nephrology (ASN): Renal Week 2007 (Abstract).
Jiang, et al., (2009) "A Novel Bile Acid Receptor Agonist Prevents Diabetic Nephropathy" 42nd Annual Meeting and Exposition of the American Society of Nephrology (ASN): Renal Week 2009 (Abstract).
Jiang, et al., (2014) "Intestinal farnesoid X receptor signaling promotes nonalcoholic fatty liver disease" The Journal of Clinical Investigation 125: 386-402.
Johansson, (2004) "Effects of the thyroid receptor-beta agonist, GC-1, on bile acid in intact male mice" 18th International Bile Acid Meeting: Bile Acid and Cholesterol Metabolism and its Therapeutic Implications (Abstract).
John, et al., (2004) "18th International Bile Acid Meeting: Bile Acid and Cholesterol Metabolism and its Therapeutic Implications" 18th International Bile Acid Meeting: Bile Acid and Cholesterol Metabolism and its Therapeutic Implications (Abstract).
Johnston. et al., (2013) "A New Therapy for Chronic Diarrhea? a Proof of Concept Study of the FXR Agonist Obeticholic Acid in Patients With Primary Bile Acid Diarrhea" 54th Annual Meeting at Digestive Disease Week (DDW 2013 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Journe et al., "Association between farnesoid X receptor expression and cell proliferation in estrogen receptor-positive luminal-iike breast cancer from postmenopausal patients," Breast Cancer Res. Treat. 115(3): 523-534, 2009, doi: 10.1007/s10549-008-0094-2.
Journe, et al., (2006) "Bone-Derived Lipid Stimulates MCF-7 Breast Cancer Cell Growth through Farnesoid X Receptor-Mediated Estrogen Receptor Activation" 28th Annual Meeting of the American Society for Bone and Mineral Research (ASBMR) (Abstract).
Journe, et al., (2006) "Crosstalk Between Farnesoid X Receptor and Estrogen Receptor Might Account for Mitogenic Effect of Bone-Derived Lipids in Bone Metastasis From Breast Cancer" 6th International Meeting on Cancer Induced Bone Disease (CABS) (Abstract).
Journe, et al., (2006) "Farnesoid X receptor: a new marker of poor prognosis in luminal subtype of breast carcinomas?" 29th Annual San Antonio Breast Cancer Symposium (SABCS) (Abstract).
Journe, et al., (2006) "Farnesol, an intermediate of the mevalonate pathway, stimulates MCF-7 breast cancer cell growth: evidence for a positive crosstalk between Farnesoid X Receptor and estrogen receptor" 29th Annual San Antonio Breast Cancer Symposium (SABCS) (Abstract).
Journe, et al., (2007) "Activation of Farnesoid X Receptor in Breast Cancer Cell Lines by Bone-Derived Lipid" 29th Annual Meeting of the American Society for Bone and Mineral Research (ASBMR) (Abstract).
Journe, et al., (2007) "Bone-Derived Lipids Stimulate Breast Cancer Cell Growth Through a Crosstalk Between Farnesoid X Receptor and Estrogen Receptor: In Vitro and Clinical Data" 34th European Symposium on Calcified Tissues (ECTS) (Abstract).
Jung, et al., (2004) "Reverse Cholesterol Transport in Cholangiocytes is Regulated by LXR" 55th Annual Meeting of the American Association for the Study of Liver Diseases (AASLD) (Abstract).
Jung, et al., (2006) "PXR is a Target of FXR" 16th International Symposium on Microsomes and Drug Oxidations (MDO) (Abstract).
Kainuma, M. et al., "Design, synthesis, and evaluation of non-steroidal farnesoid X receptor (FXR) antagonist," 2007, Bioorg. Med. Chem., 15, 2587-2600.
Kansy et al., "Physicochemical high throughput screening: parallel artificial membrane permeation assay in the description of passive absorption processes," J. Med. Chem. 41(7), 1007-1010, Mar. 26, 1998.
Kast et al., "Farnesoid X-Activated Receptor Induces Apolipoprotein C-II Transcription: a Molecular Mechanism Linking Plasma Triglyceride Levels to Bile Acids," Molecular Endocrinology, 5(10): 1720-1728, 2001.
Kast et al., "Regulation of Multidrug Resistance-associated Protein 2 (ABCC2) by the Nuclear Receptors Pregnane X Receptor, Farnesoid X-activated Receptor, and Constitutive Androstane Receptor," The Journal of Biological Chemistry, 277(4):2908-2915, 2002.
Katona, et al., (2006) "Synthesis and Nuclear Receptor Agonistic/Antagonistic Profiles of Enantiomeric Bile Acids" 97th Annual Meeting and Expo of the American Oil Chemists Society Joint Symposium on Biosciences: A Global Business Forum on Fats, Oils, Surfactants, Lipids, and Related Materials (Abstract).
Kawamura. et al., (2012) "Functional Analysis of the Farnesoid X Receptor in Colorectal Cancer Cells" 35th Annual Meeting of Molecular Biology Society of Japan (MBSJ) (Abstract).
Keating, et al., (2009) "Farnesoid X Receptor Activation Downregulates Chloride Secretion in Colonic Epithelial Cells" Digestive Disease Week 2009 (DDW) (Abstract).
Keating, et al., (2010) "Farnesoid X-receptor Agonists Inhibit Colonic Secretion In Vitro and In Vivo" Digestive Disease Week 2010 (DDW) (Abstract).
Keitel, et al., (2014) "TGR5: Pathogenetic Role and/or Therapeutic Target in Fibrosing Cholangitis?" Clinic Rev Allerg Immunol 48: 218-25.
Kennie, et al., (2013) "Relative Potencies of Bile Acids in Inducing Fibroblast Growth Factor 19 in the Human Ileum" 54th Annual Meeting at Digestive Disease Week (DDW 2013 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Kerr, et al., (2012) "Cysteine Sulfinic Acid Decarboxylase Regulation by Bile Acids: A Role for FXR and SHP in Hepatic Taurine Metabolism" 53rd Annual Meeting at Digestive Disease Week (DDW 2012 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Kim et al., "Spontaneous hepatocarcinogenesis in farnesoid X receptor-null mice," Carcinogenesis 28(5): 940-946, 2007.
Kim, et al., (2014) "Therapeutic Targets and Management of Non-Alcoholic Steatohepatitis" 20th Annual Meeting of the Korean Association for the Study of the Liver (KASL) and Postgraduate Course—Liver Week (Abstract).
Kirr, et al., (2011) "FGF19 as a Postprandial, Insulin-Independent Activator of Hepatic Protein and Glycogen Synthesis" Science 331: 1621-4.
Klaman, et al., (2007) "Potent FXR Agonist Decreases Triglyceride and Cholesterol Levels in Dyslipidemic Mice, but Does Not Lower

(56) References Cited

OTHER PUBLICATIONS

Glycemia in Insulin Resistant Mouse Models" 67th Annual Meeting and Scientific Sessions of the American Diabetes Association (ADA) (Abstract).
Kliewer, (2006) "Coordinate Regulation of Bile Acid Homeostasis & Innate Immunity by the Nuclear Bile Acid Receptor" 88th Annual Meeting of the Endocrine Society (ENDO) (Abstract).
Komichi, et al., (2004) "A Nuclear Receptor Ligand Down-Regulates Cytosolic Phospholipase A2 (cPLA2) Expression to Reduce bile Acid-Induced Cyclooxygenase 2 (COX-2) Activity in Cholangiocytes: Implication of Anti-Carcinogenic Action of Farnesoid X Receptor (FXR) Agonist" Digestive Disease Week 2004 (DDW): American Association for the Study of Liver Diseases, American Gastroenterological Association, American Society for Gastrointestinal Endoscopy, Society for Surgery of the Alimentary Tract (Abstract).
Kong, et al., (2009) "Suppression of cyp7a1 gene transcription by FXR in mice is mediated through the intestineinitiated FGF15/FGFR4 pathway rather than the liver-initiated SHP/LRH1 pathway" 60th Annual Meeting of the American Association for the Study of Liver Diseases (AASLD) (Abstract).
Kong, et al., (2011) "Differential Roles of Intestinal Fgf15 and Hepatic Shp in Feed-back Suppression of Cyp7a1 and Cyp8b1 Gene Transcription in Mice" 62nd Annual Meeting of the American Association for the Study of Liver Diseases (AASLD) (Abstract).
Kowdley, et al., (2011) "An International Study Evaluating the Farnesoid X Receptor Agonist Obeticholic Acid as Monotherapy in PBC" 46th Annual Meeting of the European Association for the Study of the Liver (EASL) (Abstract).
Kowdley, et al., (2014) "FXR Agonist Obeticholic Acid: Sustained Improvement in Markers of Cholestasis and Long-Term Safety in Patients with Primary Biliary Cirrhosis through 4 Years" 65th Annual Meeting and Postgraduate Course of the American Association for the Study of Liver Diseases (AASLD) (Abstract).
Kremoser, et al., (2010) "FXR Agonists as Novel Medication for Metabolic Syndrome and NASH" 16th World Congress of Basic and Clinical Pharmacology (WorldPharma 2010) of the International Union of Pharmacology (IUPHAR) (Abstract).
Kremoser, et al., (2010) "Phenex Pharmaceuticals AG" Poster.
Kremoser, et al., (2012) "FXR Agonists Prevent Steatosis, Hepatocyte Death and Progression of NASH Towards HCC in a Hypoinsulinaemic Mouse Model of Progressive Liver Disease" 47th Annual Meeting of the European Association for the Study of the Liver (EASL) (Abstract).
Kremoser, et al., (2012) "Synthetic FXR agonists improve liver histopathology and reduce liver tumor formation in mouse models of NASH and liver cancer" 22nd Conference of the Asian Pacific Association for the Study of the Liver (APASL) (Abstract).
Kumar, et al., (2009) "Farnesoid X ReceptorAgonist (GW4064) Protects the Kidney from Ischemic Acute Kidney Injury" 42nd Annual Meeting and Exposition of the American Society of Nephrology (ASN): Renal Week 2009 (Abstract).
Kunne, et al., (2011) "Hepatic steatosis in mice lacking hepatic cytochrome p450 activity is bile salt dependent" 62nd Annual Meeting of the American Association for the Study of Liver Diseases (AASLD) (Abstract).
Kurata, et al., (2011) Pathophysiological Role of Chenodeoxycholic Acid on Hepatic Disposition of Metformin via Organic Cation Transporter 1 in Acute Cholestasis 2011 Annual Meeting of the American Association of Pharmaceutical Scientists (AAPS) (Abstract).
Lambert et al., "The Farnesoid X-receptor is an Essential Regulator of Cholesterol Homeostasis," The Journal of Biological Chemistry, 278, 2563-2570, 2003.
Lamers, et al., (2012) "Structure and Ligand-Based Identification of Novel Synthetic Ligands for Farnesoid X Receptor" 22nd Biennial International Symposium on Medicinal Chemistry (EFMC-ISMC 2012) (Abstract).
Lamers, et al., (2014) "Medicinal Chemistry and Pharmacological Effects of Farnesoid X Receptor (FXR) Antagonists" Current Topics in Medicinal Chemistry 14: 2188-2205.

Lamers, et al., (2014) "Pyridinol/Pyridinon Tautomerism Determining Activity at Farnesoid X Receptor (FXR): New Agonistic or Antagonistic Ligands of FXR" 23rd International Symposium on Medicinal Chemistry (ISMC) held Jointly with the European Federation for Medicinal Chemistry (EFMC) (Abstract).
Lamers, et al., (2014) "Pyridinol/Pyridinon-tautomerism determining activity at Farnesoid X Receptor: new agonistic or antagonistic ligands of FXR" 2014 Annual Meeting on Trends and Perspectives in Pharmaceutical Sciences (DPhG) Annual Meeting of the German Pharmaceutical Society (DPhG) (Abstract).
Lavine, et al., (2014) "Association of Hepatic Nuclear Hormone Receptor Expression Profiles with Features of Hepatic Histology in Children with Nonalcoholic Fatty Liver Disease" 65th Annual Meeting and Postgraduate Course of the American Association for the Study of Liver Diseases (AASLD) (Abstract).
Lawson, J. et al.. "Diarylcyclobutane analogs of diethylstilbestrol," 1974, J. Med. Chem., 17, 383-386.
Leckie, et al., (2009) "Modulation of the DDAH-ADMA pathway with the Farnesoid receptor (FXR) agonist INT-747 restores hepatic eNOS activity and lowers portal pressure in cirrhotic rats" 2009 Annual Meeting of the British Association for the Study of the Liver (BASL) (Abstract).
Leclercq, (2009) "Experimental Therapies in NASH" 2009 European Association for the Study of Liver Special Conference: Non Alcoholic Fatty Liver Disease/Non Alcoholic Steato-Hepatitis (NAFLD/NASH) and Related Metabolic Disease (Abstract).
Lee, et al., (2010) "FXR Positively Regulates Hepatic SIRT1 Levels Via MicroRNA-34a Inhibition" 92nd Annual Meeting of the Endocrine Society (ENDO) (Abstract).
Li, et al., (2010) "Transgenic expression of CYP7A1 in mouse livers promotes biliary cholesterol secretion via FXRdependent induction of hepatic ABCG5 and ABCG8 expression" 61st Annual Meeting of the American Association for the Study of Liver Diseases (AASLD) (Abstract).
Li, et al., (2015) "Bile acids as metabolic regulators" Curr Opin Gastroenterol 31: 000-000.
Lian, et al., (2011) "Hepatoprotective Effect of Farnesoid X Receptor on Liver Injury in Systemic Lupus Erythematosus" 12th Annual European League Against Rheumatism (EULAR 2011) (Abstract).
Liebman, et al., (2004) "PPAR-? Agonists Modulate Renal Lipid Metabolism and Prevent the Development of Glomerulosclerosis in Zucker Diabetic Fatty Rats" 37th Annual Meeting and Exposition of the American Society of Nephrology (ASN) (Abstract).
Liem, et al., (2010) "Regulation of FXR transcriptional activity by AMPK" 2010 Nuclear Receptors: Signaling, Gene Regulation and Cancer (X7) (Abstract).
Lihong et al., American Diabetes Association (ADA) 66th annual scientific sessions, Jun. 2006, Abstract No. 856-P.
Lihong, et al., (2006) "FXR Agonist, GW4064, Reverses Metabolic Defects in High-Fat Diet Fed Mice" 66th Annual Meeting and Scientific Sessions of the American Diabetes Association (ADA) (Abstract).
Lin, (2008) "Study of role of Farnesoid X Receptor in hepatocarcinoma cells" Biennial Shanghai—Hong Kong International Liver Congress 2008 (Abstract).
Liu et al., "Hepatoprotection by the farnesoid X receptor agonist GW4064 in rat models of intra- and extrahepatic cholestasis," The Journal of Clinical Investigation, 112, 1678-1687, 2003, doi: 10.1172/JCI200318945.
Liu, et al., (2004) "Protection Against Cclinduced Hepatic Fibrosis by the Farnesoid X Receptor Agonist GW4064 in Rat" 55th Annual Meeting of the American Association for the Study of Liver Diseases (AASLD) (Abstract).
Loomba, et al., (2015) "Polyunsaturated fatty acid metabolites as novel lipidomic biomarkers for noninvasive diagnosis of nonalcoholic steatohepatitis" Journal of Lipid Research 56: 2015.
Lu et al., "Molecular Basis for Feedback Regulation of Bile Acid Synthesis by Nuclear Receptors," Molecular Cell, 6, 507-515, 2000.
Luketic, et al., (2014) "Efficacy of Obeticholic Acid in Primary Biliary Cirrhosis as Assessed by Response Criteria Associated With Clinical Outcome: A Poise Analysis" 65th Annual Meeting and Postgraduate Course of the American Association for the Study of Liver Diseases (AASLD) (Abstract).

(56) References Cited

OTHER PUBLICATIONS

Lundquist, et al., (2010), "Improvement of Physiochemical Properties of the Tetrahydroazepinoindole Series of Farnesoid X Receptor (FXR) Agonists: Beneficial Modulation of Lipids in Primates", J. Med. Chem., 53:1774-1787.

Ma et al., "Farnesoid X receptor is essential for normal glucose homeostasis," The Journal of Clinical Investigation, 116, 1102-1109, 2006, doi: 10.1172/JCI25604.

Ma, et al., (2004) "The Role of Farnesoid X Receptor (FXR) in Glucose Metabolism" 86th Annual Meeting of the Endocrine Society (ENDO) (Abstract).

Makishima et al., "Identification of a Nuclear Receptor for Bile Acids," Science, 284,:1362-1365, 1999.

Makishima, et al., (1999) "Identification of a Nuclear Receptor for Bile Acids" Science 284: 1362-1365.

Maloney et al., "Identification of a Chemical Tool for the Orphan Nuclear Receptor FXR," Journal of Medicinal Chemistry, 43, 2971-2974, 2000.

Maloney, et al., (2000) "Identification of a Chemical Tool for the Orphan Nuclear Receptor FXR" Journal of Medicinal Chemistry 43(16): 2971-2974.

Maloney, et al., (2000) "Identification of Chemical Tool for the Orphan Nuclear Receptor FXR".

Maneschi, et al., (2013) "The FXR agonist obeticholic acid normalizes lipid droplet and triglyceride handling in visceral adipose tissue preadipocytes from a non-genomic rabbit model of metabolic syndrome" 16th European Congress of Endocrinology (ECE) (Abstract).

Mangelsdorf et al., "The Nuclear Receptor Superfamily: The Second Decade," Cell, 83, 835-839, 1995.

Mangelsdorf, (2005) "The Contrasting Roles of LXRs and FXR in Lipid Metabolism" Bioactive Lipids, Lipidomics and their Targets (Z1) (Abstract).

Mangelsdorf, (2006) "Nuclear receptors and transcriptional control of lipid metabolism" 197th Annual Meeting of the Society for Endocrinology (Abstract).

Maran et al., "FXR Deficiency in Mice Leads to Increased Intestinal Epithelial Cell Proliferation and Tumor Development," American Society for Pharmacology and Experimental Therapeutics, Published on Nov. 3, 2008 as DOI: 10.1124/jpet.108.145409, 35pages.

Marinozzi, et al., (2014) "Medicinal Chemistry of Farnesoid X Receptor (FXR) Modulators: The-State-of-the-Art" Current Topics in Medicinal Chemistry 14 (19): 2127-2128.

Martinez-Fernandez, et al., (2008) "Specific down-regulation of the bile acid sensor FXR by silencing ATP8B1 in HepG2 cells. Effect of the FXR agonist GW4064" 3rd World Congress of Pediatric Gastroenterology, Hepatology and Nutrition (WCPGHAN) held jointly with the 41st Annual Meeting of the European Society for Paediatric Gastroenterology, Hepatology and Nutrition (ESPGHAN) (Abstract).

Maruyama, et al., (2010) "Selective anti-androgens with a 3,3-diphenylpentane skeleton" 2010 International Chemical Congress of Pacific Basin Societies (PACIFICHEM 2010) (Abstract).

Marzolini, et al., (2004) "Unexpected Complexity in Nuclear Receptor Activation by HIV Protease Inhibitors and Induction of CYP Enzymes and Transporters" 2004 Annual Meeting and Science Innovation Exposition of the American Association for the Advancement of Science (Abstract).

Mason, et al., (2010) "Farnesoid-X Receptor Agonists: a New Class of Drugs for the Treatment of PBC? An International Study Evaluating the Addition of Obeticholic Acid (INT-747) to Ursodeoxycholic Acid" 61st Annual Meeting of the American Association for the Study of Liver Diseases (AASLD) (Abstract).

Matsumura, S. et al., "Palladium-Catalyzed Asymmetric Arylation, Vinylation, and Allenylation of Tert-cyclobutanols via Enantioselective C—C Bond Cleavage," 2003, J. Am. Chem. Soc., 125, 8862-8869.

Matsuzaki, et al., (2012) "FXR Activation Promotes CDX2 Degradation via the Ubiquitin-Proteosome System with Upregulation of microRNA-221/222 in Human Esophageal Cells" 5th Annual International Gastrointestinal Consensus Symposium (IGICS) (Abstract).

McMahan, et al., (2009) "FXR and TGR5 Activation Improves Nonalcoholic Fatty Liver Disease (NAFLD) and Increases Intrahepatic Myeloid Suppressor Cells" 60th Annual Meeting of the American Association for the Study of Liver Diseases (AASLD) (Abstract).

McMahan, et al., (2011) "Bile-Acid Receptor Activation Shifts Hepatic Monocytes/Macrophages Towards an Anti-Inflammatory Phenotype and Improves Non-Alcoholic Fatty Liver Disease" 62nd Annual Meeting of the American Association for the Study of Liver Diseases (AASLD) (Abstract).

McMahan, et al., (2014) "Downregulation of pro-fibrotic and pro-inflammatory genes in liver sinusoidal endothelial cells following activation of the bile acid receptors FXR and TGR5" 65th Annual Meeting and Postgraduate Course of the American Association for the Study of Liver Diseases (AASLD) (Abstract).

McMillin, et al., (2014) "Central expression of the hypothalamic neuropeptide galanin is upregulated in rodent models of primary sclerosing cholangitis" 65th Annual Meeting and Postgraduate Course of the American Association for the Study of Liver Diseases (AASLD) (Abstract).

McNulty, et al., (2007) "FXR? Plays a Major Role in Cholic Acid Mediated Effects in High-fat Diet Fed Mice" 67th Annual Meeting and Scientific Sessions of the American Diabetes Association (ADA) (Abstract).

Meech, et al., (2014) "UDP-glycosyltransferase 8 (UGT8) galactosidates bile acids and modulates FXR signalling" 2014 Joint Scientific Meeting of the Australasian Society of Clinical and Experimental Pharmacologists and Toxicologists (ASCEPT) and the Molecular Pharmacology of GPCRs (MPGPCR) (Abstract).

Mencarelli, et al., (2009) "FXR Activation Corrects Immune-Dysfunction and Attenuates Inflammation in a Rodent Model of Hepatitis" Digestive Disease Week 2009 (DDW) (Abstract).

Menendez, et al., (2014) "The Effects of Bile Acids on Intestinal Antimicrobial Peptides Expression" 2014 Annual Meeting of the Canadian Association of Gastroenterology (CAG) held jointly with the Canadian Association for the Study of the Liver (CASL): Canadian Digestive Disease Week (CDDW) (Abstract).

Merk, et al., (2014) "Development of Partial Farnesoid X Receptor (FXR) Agonists" 23rd International Symposium on Medicinal Chemistry (ISMC) held Jointly with the European Federation for Medicinal Chemistry (EFMC) (Abstract).

Merk, et al., (2014) "Development of partial Farnesoid X Receptor (FXR) agonists" 2014 Annual Meeting on Trends and Perspectives in Pharmaceutical Sciences (DPhG) Annual Meeting of the German Pharmaceutical Society (DPhG) (Abstract).

Merk, et al., (2012) "Medicinal chemistry of farnesoid X receptor ligands: from agonists and antagonists to modulators" Future Med. Chem. 4(8), 1015-1036.

Miyata et al., "Role of Farnesoid X Receptor in the Enhancement of Canalicular Bile Acid Output and Excretion of Unconjugated Bile Acids: A Mechanism for Protection against Cholic Acid-Induced Liver Toxicity," The Journal of Pharmacology andExperimental Therapeutics, 312,: 759-766, 2005.

Miyazaki, et al., (2013) "Deoxycholic Acid Contributes to Chronic Kidney Disease-Dependent Vascular Calcification" 86th Annual Scientific Sessions of the American Heart Association (AHA 2013) and 2013 ReSuscitation Science Symposium (RSS) (Abstract).

Modica et al., Nuclear Bile Acid Receptor FXR Protects against Intestinal Tumorigenesis, Cancer Res, 68, 9589-9594, Dec. 1, 2008.

Mohan, et al., (2014) "Mechanism of FXR Mediated Apoptosis in Breast Cancer" 2014 Surrey Postgraduate Research Conference of the University of Surrey (Abstract).

Moloney, et al., (2009) "The Effect of the Farnesoid X Receptor (FXR) and It'S Agonist—GSK488062B—On Experimental Models of Colitis and Cytokine Production from IBD Tissue" Digestive Disease Week 2009 (DDW) (Abstract).

Mookerjee, et al., (2014) "Effects of the FXR Agonist Obeticholic Acid on Hepatic Venous Pressure Gradient (HVPG) in Alcoholic Cirrhosis: A Proof of Concept Phase 2A Study" 2014 International Liver Congress (ILC) and 49th annual meeting of the European Association for the Study of the Liver (EASL) (Abstract).

Moraes, et al., (2009) "The Nuclear Receptor FXR as a Novel Regulator of Platelet Function" 22nd Biennial Congress of the

(56) References Cited

OTHER PUBLICATIONS

International Society on Thrombosis and Haemostasis (ISTH) held jointly with the 55th Scientific and Standardisation Committee (SSC) (Abstract).
Moschetta et al., "Prevention of cholesterol gallstone disease by FXR agonists in a mouse model," Nature Medicine, 10, 1352-1358, 2004.
Moschetta, et al., (2005) "The Role of LXRs and FXR in Enterohepatic Lipid Metabolism" Tissue-Selective Nuclear Receptors (D4) (Abstract).
Moscovitz, et al., (2014) "Activation of the Farnesoid X Receptor Restores Hepatic and Intestinal Bile Acid Synthetic Enzyme and Transporter Expression in Pregnant Mice" 53rd Annual Meeting of the Society of Toxicology (SOT 2014) (Abstract).
Moussa, et al., (2014) "Activation of Bile Acid Receptor (FXR) Attenuates Osteoclast Differentiation, Survival and Function" 60th Annual Meeting of the Orthopaedic Research Society (ORS 2014) (Abstract).
Moya, et al., (2009) "Role of Nuclear Receptor Ligands in Fatty Acid-Induced Hepatic Steatosis" 2009 Joint Meeting of the European Association for the Study of the Liver (EASL) and the American Association for the Study of Liver Diseases (AASLD) Monothematic Conference: Nuclear Receptors and Liver Disease (Abstract).
Mroz, et al., (2011) "The nuclear bile acid receptor, farnesoid X receptor, inhibits CFTR expression and Clsecretion in colonic epithelial cells" 2011 Annual Conference of the Physiological Society (Abstract).
Mroz, et al., (2013) "Activation of the nuclear bile acid receptor, Farnesoid X Receptor, acutely regulates cAMPstimulated Cl-secretion in colonic epithelial cells" 2013 Physiological Society Joint Themed Meeting on Epithelia and Smooth Muscle Interactions in Health and Disease (Abstract).
Mroz, et al., (2014) "Agonists of the nuclear bile acid receptor, FXR, prevent secretory diarrhoea by a novel mechanism involving repression of CFTR promoter activity" 2014 Conference on Physiology—Physiological Society (Abstract).
Mudaliar, et al., (2009) "Farnesoid-X receptor agonists—a new therapeutic class for diabetes and NAFLD—first clinical data" 45th Annual Meeting of the European Association for the Study of Diabetes (EASD) (Abstract).
Nejak-Bowen, et al., (2013) "Novel therapeutic implications of modulating ß-Catenin during intrahepatic cholestasis" 64th Annual Meeting and Postgraduate Course of the American Association for the Study of Liver Diseases (AASLD) (Abstract).
Nettles et al., "Ligand Control of Coregulator Recruitment to Nuclear Receptors," Annu. Rev. Physiol. 67, 09-333, 2005.
Neuschwander Tetri, (2015) "Targeting the FXR Nuclear Receptor to Treat Liver Disease" Division of Gastroenterology and Hepatology.
Neuschwander-Tetri, et al., (2014) "Farnesoid X nuclear receptor ligand obeticholic acid for non-cirrhotic, non-alcoholic steatohepatitis (FLINT): a multicentre, randomised, placebo-controlled trial" The Lancet 385 (9972): 956-965.
Neuschwander-Tetri, et al., (2014) "Farnesoid-X nuclear receptor ligand obeticholic acid for non-cirrhotic, non-alcoholic steatohepatitis (FLINT): a multicentre, randomised, placebocontrolled trial" The Lancet.
Nevens, et al., (2014) "An International Phase 3 Study of the FXR Agonist Obeticholic Acid in PBC Patients: Effects on Markers of Cholestasis Associated with Clinical Outcomes and Hepatocellular Damage" 65th Annual Meeting and Postgraduate Course of the American Association for the Study of Liver Diseases (AASLD) (Abstract).
Nevens, et al., (2014) "The First Primary Biliary Cirrhosis (PBC) Phase 3 Trial in Two Decades—An International Study of the FXR Agonist Obeticholic Acid in PBC Patients" 2014 International Liver Congress (ILC) and 49th annual meeting of the European Association for the Study of the Liver (EASL) (Abstract).

Nijmeijer, et al., (2009) "Genetic Variants of Farnesoid X Receptor (FXR) Predispose to Mortality and Infectious Complications in Acute Pancreatitis" Digestive Disease Week 2009 (DDW) (Abstract).
Nolan, et al., (2012) "The Induction of FGF19 in Human Ileum by Bile Acids Reflects Their Relative Potencies as FXR-Binding Ligands" 20th Annual Meeting of the United European Gastroenterology Week (UEGW) (Abstract).
Nolan, et al., (2014) "The Effects of Obeticholic Acid, a Farnesoid X Receptor Agonist, in Patients With Chronic Diarrhea Secondary to Crohn's Ileal Disease" 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Parks et al., "Bile Acids: Natural Ligands for an Orphan Nuclear Receptor," Science,284, 1365-1368, May 21, 1999.
Patman, et al., (2014) "A variant of FGF19 protects the liver from cholestatic injury without inducing cancer" Nature Reviews Gastroenterology & Hepatology.
Payer, et al., (2014) "The synthetic FXR agonist PX20606 attenuates bacterial translocation, intestinal inflammation, and reduces splanchnic blood flow in portal hypertensive mice" 47. Jahrestagung der Österreichischen Gesellschaft für Gastroenterologie und Hepatologie (ÖGGH) statt gemeinsam mit der 25. Lehrgang der Österreichischen Gesellschaft für Gastroenterologie und Hepatologie / 47th Annual Meeting of the Austrian Society for Gastroenterology and Hepatology held jointly with the 25th training course of the Austrian Society of Gastroenterology and Hepatology (Abstract).
Pedraz, et al., (2012) "Transcription elongation factor TFIIS.1 gene is regulated by farnesoid X receptor" 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SEBBM) (Abstract).
Pellicciari et al., "6a-Ethyl-Chenodeoxycholic Acid (6-ECDCA), a Potent and Selective FXR Agonist Endowed with Anticholestatic Activity," Journal of Medicinal Chemistry, 45. 3569-3572, Aug. 15, 2002.
Pellicciari, (2008) "Novel Targets for Metabolic Diseases" Metabolic Disorders: From Bench to Bedside (Abstract).
Pellicciari, (2009) "Genomic and Nongenomic Bile Acid Receptors as Novel Targets for the Treatment of Metabolic Disorders" 6th Biennial Joint Meeting of the European Federation for Medicinal Chemistry (EFMC) (Abstract).
Peng, et al., (2012) "SRC-Mediated Cross-Talk Between Farnesoid X and Epidermal Growth Factor Receptors Inhibits Human Intestinal Cell Proliferation and Tumorigenesis" 53rd Annual Meeting at Digestive Disease Week (DDW 2012 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Penna, et al., (2009) "Inhibition of Experimental Colitis by Farnesoid X Receptor Agonists" 2009 European Congress of Immunology (ECI): 2nd Joint Meeting of European National Societies of Immunology under the Auspices of EFIS (Abstract).
Perttilä, et al., (2010) "Adiponutrin, a lipid droplet surface enzyme—evidence for regulation by ChREBP, SREBP1c and FXR in human hepatocytes" 46th Annual Meeting of the European Association for the Study of Diabetes (EASD) (Abstract).
Plass et al., "Farnesoid X Receptor and Bile Salts are Involved in Transcriptional Regulation of the Gene Encoding the Human Bile Salt Export Pump," Hepatology, 35, 589-596, Mar. 2002.
Poupon, (2007) "Targeting Cholestasis" European Association for the Study of the Liver Monothematic Conference: Primary Biliary Cirrhosis (PBC) (Abstract).
Prentiss, et al., (2008) "Characterization of Transporter Expression in Primary Cultures of Human Hepatocytes" 10th European Meeting of the International Society for the Study of Xenobiotics (ISSX) (Abstract).

(56) References Cited

OTHER PUBLICATIONS

Prough, et al., (2014) "PCB regulation of hepatic nuclear receptors: Implications for hepatic steatosis" 5th Asia Pacific Regional Meeting of the International Society for the Study of Xenobiotics (ISSX 2014) (Abstract).
Qin, et al., (2006) "Bile acids induces hypercholesterolemia through a FXR-independent mechanism in LDLR Knockout mice" Nuclear Receptors: Orphan Brothers (X3) (Abstract).
Qin, et al., (2006) "Bile ACIS Induce Hypercholesterolemia Through a FXR-Independent Mechanism in LDLR Knockout Mice" 14th International Symposium on Atherosclerosis (ISA) (Abstract).
Quiroga, et al., (2012) "Deficiency of Carboxylesterase 1/Esterase-x Results in Obesity, Hepatic Steatosis, and Hyperlipidemia" Hepatology, 56 (6): 2188-2198.
Radreau, et al., (2014) "Bile acids receptor FXR agonists repress HBV replication in HepaRG cell" 65th Annual Meeting and Postgraduate Course of the American Association for the Study of Liver Diseases (AASLD) (Abstract).
Ratziu, et al., (2014) "Starting the battle to control non-alcoholic steatohepatitis" Institute for Cardiometabolism and Nutrition, Universite Pierre et Marie Curie, Assistance Publique Hopitaux de Paris.
Renga, et al., (2009) "A Dark Side of FXR Activation in Cholestasis. FXR is a Negative Regulator of MRP4" Digestive Disease Week 2009 (DDW) (Abstract).
Renga, et al., (2012) "A Farnesoid-X-receptor (FXR)-Glucocorticoid Receptor (GR) Cascade Regulates Intestinal Innate Immunity in Response to FXR Activation" 53rd Annual Meeting at Digestive Disease Week (DDW 2012 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Renga, et al., (2012) "Theonellasterol: a highly selective FXR antagonist that protects against liver injury in cholestasis" 34th National Conference of the Division of Organic Chemistry—Italian Chemical Society/ 34 Convegno Nazionale della Divisione di Chimica Organica—Società Chimica Italiana (SCI) (Abstract).
Richter, et al., (2011) "Discovery of novel and orally active FXR agonists for the potential treatment of dyslipidemia & diabetes" Bioorganic & Medicinal Chemistry Letters 21: 191-194.
Richter, et al., (2011) "Optimization of a novel class of benzimidazole-based farnesoid X receptor (FXR) agonists to improve physicochemical and ADME properties" Bioorganic & Medicinal Chemistry Letters 21: 1134-1140.
Ricketts, et al., (2006) "The coffee diterpene, cafestol regulates cholesterol homeostasis from the intestine via FXR and FGF15" Nuclear Receptors: Orphan Brothers (X3) (Abstract).
Rizzo et al., "Role of FXR in Regulating Bile Acid Homeostasis and Relevance for Human Diseases," Current Drug Targets—Immune, Endocrine & Metabolic Disorders, 5, 289-303, 2005.
Rizzo, et al., (2009) "INT-747: a Potent and Selective FXR Agonist Regulating Glucose Metabolism and Enhancing Insulin Secretion" 60th Annual Meeting of the American Association for the Study of Liver Diseases (AASLD) (Abstract).
Rizzo, et al., (2009) "The Farnesoid X Receptor Agonist INT-747 Enhances Glucose-Induced Insulin Secretion" 2009 Joint Meeting of the European Association for the Study of the Liver (EASL) and the American Association for the Study of Liver Diseases (AASLD) Monothematic Conference: Nuclear Receptors and Liver Disease (Abstract).
Rizzo, et al., (2010) "Functional Characterization of the Semi-Synthetic Bile Acid Derivative INT-767, A Dual FXR and TGR5 Agonist" 16th World Congress of Basic and Clinical Pharmacology (WorldPharma 2010) of the International Union of Pharmacology (IUPHAR) (Abstract).
Rizzo, et al., (2010) "Functional Characterization of the Semi-Synthetic Bile Acid Derivative INT-767, A Dual FXR and TGR5 Agonist" 45th Annual Meeting of the European Association for the Study of the Liver (EASL) (Abstract).
Rizzo, et al., (2010) "Functional characterization of the semi-synthetic bile acid derivative INT-767, A dual FXR and TGR5 agonist" 61st Annual Meeting of the American Association for the Study of Liver Diseases (AASLD) (Abstract).
Rizzo, et al., (2011) "Functional Characterization of the Semi-synthetic Bile Acid Derivative Int-767, a Dual FXR and TGR5 Agonist" 21st Conference of the Asian Pacific Association for the Study of the Liver (APASL) (Abstract).
Robitaille, et al., (2008) "Role of the Farnesoid X Receptor (FXR) in Intestinal Epithelial Cell Growth and Differentiation" 2008 Annual Meeting of the Canadian Digestive Disease Week (CDDW) (Abstract).
Sanyal, (2011) "Emerging Treatments of NASH" 21st Conference of the Asian Pacific Association for the Study of the Liver (APASL) (Abstract).
Sanyal, et al., (2009) "A New Therapy for Nonalcoholic Fatty Liver Disease and Diabetes? INT-747—the First FXR Hepatic Therapeutic Study" 60th Annual Meeting of the American Association for the Study of Liver Diseases (AASLD) (Abstract).
Sanyal, et al., (2013). "Novel therapeutic targets for alcoholic hepatitis" 14th Biennial Congress of the European Society for Biomedical Research on Alcoholism (ESBRA) (Abstract).
Sanz Ortega, et al., (2012) "Effect of treatment with glucocorticoids FXR-mediated signaling pathway and bile acid homeostasis" 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (SEBBM) (Abstract).
Savkur, et al., (2005) "Regulation of Pyruvate Dehydrogenase Kinase Expression by the Farnesoid X Receptor" Bioactive Lipids, Lipidomics and their Targets (Z1) (Abstract).
Schaap, et al., (2006) "Evidence for regulation of human FGF19 gene expression by ileal FXR" 57th Annual Meeting of the American Association for the Study of Liver Diseases (AASLD) (Abstract).
Schaap, et al., (2009) "FGF19 Represses CYP7A1 Through an ERK1/2-Dependent Pathway" 2009 Joint Meeting of the European Association for the Study of the Liver (EASL) and the American Association for the Study of Liver Diseases (AASLD) Monothematic Conference: Nuclear Receptors and Liver Disease (Abstract).
Schaap, et al., (2014) "Bile acid receptors as targets for drug development" Nat. Rev. Gastroenterol. Hepatol. 11, 55-67.
Schena et al., "Mammalian Glucocorticoid Receptor Derivatives Enhance Transcription in Yeast," Science 241, 965-967, Aug. 19, 1988.
Schittenhelm, et al., (2013) "Bile acids affect beta-cell function and glucose homeostasis by interference with the Farnesoid X Receptor (FXR)" 92nd Annual Meeting of the German Physiological Society/ Deutsche Physiologische Gesellschaft (DPG) (Abstract).
Schonewille, et al., (2014) "Combination Treatment of the Novel Pharmacological FXR-Compound PX20606 and Ezetimibe Leads to Massively Increased Neutral Sterols Excretion in Mice" 82nd European Atherosclerosis Society Congress (EAS) (Abstract).
Schubert-Zsilavecz, (2014) "Medicinal chemistry of Farnesoid X Receptor ligands" 134th Annual Meeting of the Pharmaceutical Society of Japan (PSJ) (Abstract).
Schwabl, et al., (2014) The Synthetic FXR Agonist PX20606 Attenuates Bacterial Translocation, Intestinal Inflammation, and Reduces Splanchnic Blood Flow in Portal Hypertensive Mice 2014 International Liver Congress (ILC) and 49th annual meeting of the European Association for the Study of the Liver (EASL) (Abstract).
Sepe, et al., (2012) "Conicasterol E, a small heterodimer partner sparing farnesoid-X-receptor modulator endowed with a pregnane-X-receptor agonistic activity, from the marine sponge *Theonella swinhoei*" 34th National Conference of the Division of Organic Chemistry—Italian Chemical Society/ 34 Convegno Nazionale della Divisione di Chimica Organica—Società Chimica Italiana (SCI) (Abstract).
Shapiro, et al., (2009) "First Human Experience With a Synthetic Farnesoid X Receptor (FXR) Agonist-INT-747 (6-Ethylchenodeoxycholic Acid)" 2009 Joint Meeting of the European Association for the Study of the Liver (EASL) and the

(56) References Cited

OTHER PUBLICATIONS

American Association for the Study of Liver Diseases (AASLD) Monothematic Conference: Nuclear Receptors and Liver Disease (Abstract).
Shapiro, et al., (2009) "First Human Experience With a Synthetic Farnesoid X Receptor (FXR) Agonist-INT-747 (6a-Ethylchenodeoxycholic Acid)" 60th Annual Meeting of the American Association for the Study of Liver Diseases (AASLD) (Abstract).
Sinal et al., "Targeted Disruption of the Nuclear Receptor FXR/BAR Impairs Bile Acid and Lipid Homeostasis," Cell 102:731-744, Sep. 15, 2000.
Smalley Jr., et al., (2015) "Novel heterocyclic scaffolds of GW4064 as farnesoid X receptor agonists" Bioorganic & Medicinal Chemistry Letters 25: 280-284.
Song, et al., (2008) "Bile Acids Activate Farnesoid X Receptor and Fibroblast Growth Factor 19 Signaling to Inhibit Cholesterol 7a-Hydroxylase Gene Expression in Human Hepatocytes" 90th Annual Meeting of the Endocrine Society (ENDO) (Abstract).
Soo Shin, et al., (2013) "Positive regulation of osteogenesis by bile acid through FXR" 40th Annual Congress of the European Calcified Tissue Society (ECTS 2013) (Abstract).
Staels, (2006) "Nuclear receptors as therapeutic targets to modulate the metabolic syndrome" 31st International Meeting of the Federation of the European Biochemical Societies (FEBS) (Abstract).
Staels, (2009) "Bile acids : from simple detergents to complex signalling molecules controlling lipid and glucose homeostasis" 6th Annual Congress on Metabolic Syndrome, Type II Diabetes and Atherosclerosis (Abstract).
Stayrook et al., Regulation of Carbohydrate Metabolism by the Farnesoid X Receptor, Endocrinology, 146, 984-991, 2005.
Stayrook, et al., (2005) "Regulation of Carbohydrate Metabolism by the Farnesoid X Receptor" Bioactive Lipids, Lipidomics and their Targets (Z1) (Abstract).
Suzuki, et al., (2008) "Mechanism of regulation of bile acid transport in the small intestine" Falk Symposium 165: 20th International Bile Acid Meeting (Abstract).
Swales et al., "The Farnesoid X Receptor is Expressed in Breast Cancer and Regulates Apoptosis and Aromatase Expression," Cancer Res., 66, 10120-10126, Oct. 15, 2006.
Taiwanese Search Report for TW101123785, completed Jan. 16, 2013.
Takada, et al., (2006) "Transcriptional regulation of mouse organic solute transporter alpha and beta by FXR and LXR alpha" Falk Symposium No. 155: XIX International Bile Acid Meeting—Bile Acids: Biological Actions and Clinical Relevance (Abstract).
Tazuma, (2004) "A nuclear receptor ligand down-regulates cytosolic phosphollpaseA2(cPLA2)expression to reduce bile acid-Induced cyclooxygenase 2 (COX-2) activity in cholanglocytes: Implication of anticarcinogenic action of farnesold X receptor (FXR) agonist" 18th International Bile Acid Meeting: Bile Acid and Cholesterol Metabolism and its Therapeutic Implications. (Abstract).
Tazuma, et al., (2004) "A nuclear receptor ligand down-regulates cytosolic phospholipase AcPLA expression to reduce bile acid-induced cyclooxygenase 2 (COX-2) activity in cholangiocytes: Implication of anticarcinogenic action of Farnesoid X Receptor (FXR) agonist" Falk Symposium No. 141 Bile Acids and Cholesterol Metabolism and its Therapeutical Implications (Abstract).
Tomlinson et al., "Transgenic Mice Expressing Human Fibroblast Growth Factor-19 Display Increased Metabolic Rate and Decreased Adiposity," Endocrinology, 143, 1741-1747, May 2002.
Trauner, (2010) "Nuclear hormone receptors—biliary diseases" 2010 European Association for the Study of the Liver (EASL) Monothematic Conference: Signaling in the Liver (Abstract).
Trauner, (2014) "Bile acids as regulators of hepatic transport and metabolism in cholestatic and metabolic liver diseases" 20th International Symposium on MIcrosomes and Drug Oxidations (Abstract).
Trauner, (2014) "FXR VS PPAR Agonists: Competitors or Fellow-Combatants" 2014 European Association for the Study of the Liver (EASL) Monothematic Conference: Primary Biliary Cirrhosis (PBC) (Abstract).

Unsworth, et al., (2014) "Non-genomic effects of nuclear receptors: Different mechanisms of regulation of outside—in signalling in platelets" 2nd European Platelet Group Conference (EUPLAN) (Abstract).
Uriarte, et al., (2014) "Ileal FGF15 contributes to fibrosis-associated hepatocellular carcinoma development" International Journal of Cancer.
Urizar et al., "A Natural Product That Lowers Cholesterol as an Antagonist Ligand for FXR," Science, 296, 1703-1706, May 31, 2002.
Urizar et al., "The Farnesoid X-activated Receptor Mediates Bile Acid Activation of Phospholipid Transfer Protein Gene Expression," The Journal of Biological Chemistry, 275, 39313-39317, Dec. 15, 2000.
Vairappan, et al., (2009) "Modulation of the DDAH-ADMA pathway with the Farnesoid receptor (FXR) agonist INT-747 restores hepatic eNOS activity and lowers portal pressure in cirrhotic rats" 2009 Annual Meeting of the British Association for the Study of the Liver (Abstract).
Vairappan, et al., (2009) "Modulation of the DDAH-ADMA pathway with the Farnesoid X Receptor (FXR) agonist INT-747 restores hepatic eNOS activity and lowers portal pressure in cirrhotic rats" 60th Annual Meeting of the American Association for the Study of Liver Diseases (Abstract).
Vaquero, et al., (2012) "Role of BCRP in FXR-induced chemoresistance in liver and intestinal cancer cells" 37th Congress of Federation of the European Biochemical Societies (FEBS) held jointly with the 22nd Conference of the International Union of Biochemistry and Molecular Biology (IUBMB) and the Spanish Society of Biochemistry and Molecular Biology (Abstract).
Vassie, et al., (2014) "Obeticholic Acid, a Farnesoid X Receptor Agonist, Reduces Bile Acid Synthesis in Patients With Primary Bile Acid Diarrhea" 55th Annual Meeting at Digestive Disease Week (DDW 2014 ): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Verbeke, et al., (2013) "Obeticholic acid, a farnesoid-X receptor agonist, improves portal hypertension by two distinct pathways in cirrhotic rats" 64th Annual Meeting and Postgraduate Course of the American Association for the Study of Liver Diseases (Abstract).
Verbeke, et al., (2014) "Obeticholic Acid, A Farnesoid-X Receptor Agonist, Improves Portal Hypertension in Cirrhotic Rats" 26th Belgian Week of Gastroenterology (Abstract).
Verbeke, et al., (2014) "Obeticholic Acid, A Farnesoid-X Receptor Agonist, Reduces Bacterial Translocation and Restores Intestinal Permeability in a Rat Model of Cholestatic Liver Disease" 2014 International Liver Congress (ILC) and 49th annual meeting of the European Association for the Study of the Liver (Abstract).
Verbeke, et al., (2014) "Obeticholic Acid, An FXR Agonist, Reduces Bacterial Translocation in Experimental Cholestasis" 26th Belgian Week of Gastroenterology (Abstract).
Visschers, et al., (2011) "FXR stimulation with INT-747 in a rat biliary drainage model protects from hepatocellular injury after loss of enterohepatic circulation" 2011 Annual Meeting of the British Association for the Study of the Liver (Abstract).
Visschers, et al., (2012) "Cholangiopathy is the Trigger for Intestinal Failure Associated Liver Disease Through Failure of CYP7A1 Inhibition Resulting From Lack of FXR Stimulation After Biliary Drainage in Rats" 34th Annual Congress of the European Society for Clinical Nutrition and Metabolism (Abstract).
Visschers, et al., (2012) "FXR Stimulation With INT-747 in a Rat Biliary Drainage Model Protects From Hepatocellular Injury After Loss of Enterohepatic Circulation" 47th Annual Meeting of the European Association for the Study of the Liver (Abstract).
Vlasuk, et al., (2007) "Introduction to mechanistic approaches to increasing high density lipoprotein cholesterol" 233rd National Meeting of the American Chemical Society (Abstract).
Wagner, et al., (2007) "Absence of FXR Protects Mice From Bile-Infarcts in Biliary Obstruction Byreduction of Bile Acid-Independent Bile Flow: Implications for Targeting FXR in Treatment of Cholestasis?" 42nd Annual Meeting of the European Association for the Study of the Liver (Abstract).

(56) References Cited

OTHER PUBLICATIONS

Wagner, et al., (2007) "Ursodeoxycholic acid (UDCA) stimulates intestinal fibroblast growth factor 15 (Fgf-15) expression independent of the Farnesoid X Receptor (FXR)" Digestive Disease Week 2007 (DDW): American Association for the Study of Liver Diseases (AASLD), American Gastroenterological Association (AGA), American Society for Gastrointestinal Endoscopy (ASGE), Society for Surgery of the Alimentary Tract (SSAT) (Abstract).
Wang et al., "FXR: a metabolic regulator and cell protector," Cell Research 18(11): 10871095, 2008, doi: 10.1038/cr.2008.289.
Wang, et al., (2007) "FXR Modulates Renal Lipid Metabolism and Fibrosis in Diabetic Nephropathy" 2007 Experimental Biology Annual Meeting (FASEB) held jointly with the 2007 Annual Meeting of the American Society for Investigative Pathology (Abstract).
Wang, et al., (2008) "FXR Agonist Modulates Renal lipid Metabolism, Inflammation, Oxidative Stress and Fibrosis in Diet-induced Obesity and Renal Disease" 2008 Nuclear Receptors: Orphan Brothers (Abstract).
Wang, et al., (2009) "Farnesoid X Receptor Deficiency Accelerates Diabetic Nephropathy in Nephropathy-Resistant C57BL/6 Mice" 42nd Annual Meeting and Exposition of the American Society of Nephrology (Abstract).
Wang, et al., (2010) "Dual Bile Acid Receptors Agonist INT-767 Prevents Diabetic Nephropathy through Multiple Mechanisms" 43rd Annual Meeting and Exposition of the American Society of Nephrology (Abstract).
Wang, et al., (2014) "Treatment with the FXR-TGR5 dual agonist INT-767 decreases NAFLD-NASH in mice fed a Western diet" 65th Annual Meeting and Postgraduate Course of the American Association for the Study of Liver Diseases (Abstract).
Watanabe et al., "Bile acids lower triglyceride levels via a pathway involving FXR, SHP, and SREBP-1c," The Journal of Clinical Investigation, 113, 1408-1418, May 2004.
Watanabe, et al., (2006) "Bile acids induce energy expenditure by promoting intracellular thyroid hormone activation" Nature Publishing Group 439 (26): 484-489.
Watanabe, et al., (2010) "Lowering bile acid pool size with an FXR agonist induces obesity and diabetes through the decrease of energy expenditure" 2010 Nuclear Receptors: Development, Physiology and Disease (Abstract).
Watts (2013) "Hepatic Steatosis, Dyslipoproteinaemia and Cardiometabolic Disease" 2013 Annual Scientific Meeting of the Australian Diabetes Educators Association (ADEA) and the Australian Diabetes Society (ADS) (Abstract).
Willson et al., "Chemical Genomics: Functional Analysis of Orphan Nuclear Receptors in the Regulation of Bile Acid Metabolism," Medicinal Research Reviews, 21, 513-522, 2001.
Winkler, et al., (2012) "Transcriptional regulation of hepatic and extrahepatic glucuronidation in tgUGT1A WT mice in obstructive cholestasis (BDL) and by FXR agonist GW4064" 63rd Annual Meeting and Postgraduate Course of the American Association for the Study of Liver Diseases (Abstract).
Wittenburg et al., "FXR and ABCG5/ABCG8 as Determinants of Cholesterol Gallstone Formation From Quantitative Trait Locus Mapping in Mice," Gastroenterology, 125, 868-881, Sep. 2003.

Xie, et al., (2014) "Metabolites Profiling Identifies a Key Role of Farnesoid X Receptor for Glucose Metabolism in Proliferating Cells" 5th Asia Pacific Regional Meeting of the International Society for the Study of Xenobiotics (Abstract).
Xing, et al., (2007) "Adrenal Expression of 3s-Hydroxysteroid Dehydrogenase Type II is Regulated by the Farnesoid X Receptor (FXR, NR1H4)" 89th Annual Meeting of the Endocrine Society (Abstract).
Xing, et al., (2008) "FXR Induces Liver Hypertrophy Through the Homeobox Factor Hex" Digestive Disease Week 2008 (Abstract).
Xu, et al., (2014) "The Role of Bile Acid Receptor FXR Activation on NHE8 Expression Regulation." 55th Annual Meeting at Digestive Disease Week (Abstract).
Yamada, et al., (2008) "Bile Acids Induce CDX2 Expression via Farnesoid X Receptor (FXR) in Barrett's Oesophagus." 16th Annual Meeting of the United European Gastroenterology Week (Abstract).
Yang et al., "Spontaneous Development of Liver Tumors in the Absence of the Bile Acid Receptor Farnesoid X Receptor," Cancer Res, 67, 863-867, Feb. 1, 2007.
Yingji, et al., (2009) "Bile Acids Induce Expression of CDx2 and MUC2 in Normal Rat Gastric Epithelial Cells via Activation of Nuclear Receptor FXR—a Possible Mechanism of Intestinal Metaplasia in the Stomach." Digestive Disease Week 2009 (Abstract).
Yu, et al., (2014) "A Novel Treatment for Liver Injury in Western Diet Mouse Models" 1st Annual in Silico Drug Discovery Conference (Abstract).
Yu, et al., (2014) "A novel treatment for liver injury in Western diet mouse models." 70th Annual Southwest Regional Meeting of the American Chemical Society (Abstract).
Zhan, et al., (2013) "Genome-wide binding and transcriptome analysis of human Farnesoid X Receptor in the liver" 2013 Experimental Biology Annual Meeting (Abstract).
Zhan, et al., (2014) "Genome-Wide Binding and Transcriptome Analysis of Human Farnesoid X Receptor in Primary Human Hepatocytes" PLOS One 9(9).
Zhang et al., "Activation of the nuclear receptor FXR improves hyperglycemia and hyperlipidemia in diabetic mice," PNAS 103(a): 1006-1011, Jan. 24, 2006.
Zhang, et al., (2007) "FXR signaling in metabolic disease" FEBS Letters 582: 10-18.
Zhang, et al., (2009) "Farnesoid X receptor agonist WAY-362450 attenuatesliver inflammation and fibrosis in murine model of non-alcoholic steatohepatitis" Journal of Hepatology 51: 380-388.
Zhang, et al., (2010) "Identification of Novel Pathways That Control FXR-mediated Hypocholesterolemia" 2010 Nuclear Receptors: Development, Physiology and Disease (X8) (Abstract).
Zhang, et al., (2010) "Identification of Novel Pathways that Control FXR-Regulated Cholesterol Homeostasis" 11th Annual Conference on Arteriosclerosis, Thrombosis and Vascular Biology (Abstract).
Zhang, et al., (2015) "GW4064, an agonist of farnesoid X receptor (FXR), represses CYP3A4 expression in human hepatocytes by inducing small heterodimer partner (SHP) expression".
Zollner et al., "Role of Nuclear Receptors in the Adaptive Response to Bile Acids and Cholestasis: Pathogenetic and Therapeutic Considerations," Molecular Pharmaceutics 3(3): 231-251,2006.

* cited by examiner

FXR (NR1H4) BINDING AND ACTIVITY MODULATING COMPOUNDS

CROSS-REFERENCE TO RELATED APPLICATIONS

This application is a continuation of U.S. application Ser. No. 15/369,521, filed Dec. 5, 2016, now U.S. Pat. No. 9,820,979, which is a continuation of U.S. application Ser. No. 14/824,971, filed Aug. 12, 2015, now U.S. Pat. No. 9,539,244, which is a continuation of U.S. application Ser. No. 14/232,118, filed Apr. 11, 2014, now U.S. Pat. No. 9,139,539, which is a national phase application under 35 U.S.C. § 371 of International Application No. PCT/EP2012/002941, filed Jul. 12, 2012, which claims the benefit of U.S. Application Ser. No. 61/507,153 and European Patent Application Serial No. 11005722.1, both filed Jul. 13, 2011. The entire contents of these applications are incorporated herein by reference in their entireties.

The present invention relates to compounds which bind to the NR1H4 receptor (FXR) and act as agonists or modulators of FXR. The invention further relates to the use of the compounds for the treatment and/or prophylaxis of diseases and/or conditions through binding of said nuclear receptor by said compounds.

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface (D. J. Mangelsdorf et al., Cell 1995, 83, 835; R. M. Evans, Mol. Endocrinol. 2005, 19, 1429).

In general, three functional domains have been defined in NRs. An amino terminal domain is believed to have some regulatory function. It is followed by a DNA-binding domain hereinafter referred to as "DBD" which usually comprises two zinc finger elements and recognizes a specific Hormone Responsive Element hereinafter referred to as "HRE" within the promoters of responsive genes. Specific amino acid residues in the "DBD" have been shown to confer DNA sequence binding specificity (M. Schena and K. R. Yamamoto, Science 1988, 241, 965). A ligand-binding-domain hereinafter referred to as "LBD" is at the carboxy-terminal region of known NRs.

In the absence of hormone, the LBD appears to interfere with the interaction of the DBD with its HRE. Hormone binding seems to result in a conformational change in the NR and thus opens this interference (A. M. Brzozowski et al., Nature 1997, 389, 753). A NR without the LBD constitutively activates transcription but at a low level.

Coactivators or transcriptional activators are proposed to bridge between sequence specific transcription factors, the basal transcription machinery and in addition to influence the chromatin structure of a target cell. Several proteins like SRC-1, ACTR, and Grip1 interact with NRs in a ligand enhanced manner (D. M. Heery et al., Nature 1997, 387, 733; T. Heinzel et al., Nature 1997, 387, 43; K. W. Nettles and G. L. Greene, Annu. Rev. Physiol. 2005, 67, 309).

Nuclear receptor modulators like steroid hormones affect the growth and function of specific cells by binding to intracellular receptors and forming nuclear receptor-ligand complexes. Nuclear receptor-hormone complexes then interact with a HRE in the control region of specific genes and alter specific gene expression (A. Aranda and A. Pascual, Physiol. Rev. 2001, 81, 1269).

The Farnesoid X Receptor alpha (hereinafter also often referred to as NR1H4 when referring to the human receptor) is a prototypical type 2 nuclear receptor which activates genes upon binding to promoter region of target genes in a heterodimeric fashion with Retinoid X Receptor (B. M. Forman et al., Cell 1995, 81, 687). The relevant physiological ligands of NR1H4 are bile acids (D. J. Parks et al., Science 1999, 284, 1365; M. Makishima et al., Science 1999, 284, 1362). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signalling by upregulating the expression of the cytokine Fibroblast Growth Factor 15 (rodents) or 19 (monkeys, humans, J. A. Holt et al., Genes Dev. 2003, 17, 1581; T. Inagaki et al., Cell Metab. 2005, 2, 217).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539 and WO 2008/025540. Further small molecule FXR modulators have been recently reviewed (M. L. Crawley, Expert Opin Ther. Pat. 2010, 20, 1047; D. Merk et al., Future Med. Chem. 2012, 4, 1015).

In WO 2011/020615 we disclosed chiral cyclopropylidene compounds of the following general formula

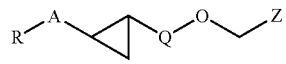

wherein the variables are defined similar as in this application.

The problem underlying the present invention is to generate FXR-agonists with improved physicochemical properties in general, and reduced hydrophobicity, improved aqueous solubility and better membrane permeability, in particular, compared to compounds claimed in WO 2011/020615.

Said problem has been solved by a compound according to the following Formula (1), an enantiomer, diastereomer, tautomer, solvate, prodrug or pharmaceutical acceptable salt thereof

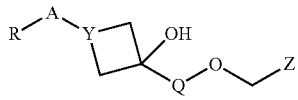
(1)

wherein
R is selected from the group consisting of $COOR_6$, $CONR_7R_8$, tetrazolyl, $SO_2NR_7R_8$, $C_{1-6}$ alkyl, $SO_2$—$C_{1-6}$ alkyl and H, with $R_6$ independently selected from the group consisting of H or $C_{1-6}$ alkyl, and $R_7$ and $R_8$ independently from each other selected from the group consisting of H, $C_{1-6}$ alkyl, halo-$C_{1-6}$ alkyl, $C_{1-6}$ alkylene-$R_9$, $SO_2$—$C_{1-6}$ alkyl, wherein $R_9$ is selected from the group consisting of COOH, OH and $SO_3H$;

A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, each optionally substituted with one or two groups independently selected from the group consisting of OH, O—$C_{1-6}$ alkyl, O-halo-$C_{1-6}$ alkyl, $C_{1-6}$ alkyl, halo-$C_{1-6}$ alkyl, $C_{3-6}$ cycloalkyl and halogen;

Q is selected from the group consisting of phenyl, pyridyl, thiazolyl, thiophenyl, pyrimidyl, each optionally substituted with one or two groups independently selected from the group consisting of $C_{1-6}$ alkyl, halo-$C_{1-6}$ alkyl, halogen and $CF_3$;

Y is selected from N or CH;
Z is selected from

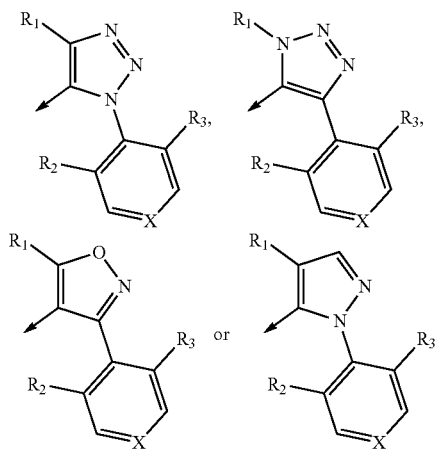

wherein
X=CH, N, NO;
$R_1$ is selected from the group consisting of hydrogen, $C_{1-3}$ alkyl, $C_{3-6}$ cylcoalkyl, $C_{4-5}$ alkylcycloalkyl, wherein $C_{1-3}$ alkyl is optionally substituted with 1 to 3 substituents independently selected from halogen, hydroxy or $C_{1-6}$ alkoxy;
$R_2$ and $R_3$ are independently selected from the group consisting of hydrogen, $C_{1-3}$ alkyl, $C_{1-3}$ haloalkyl, $C_{1-3}$ alkoxy, $C_{1-3}$ haloalkoxy and halogen.

In another embodiment in combination with any of the above or below embodiments, R-A in the compound according to Formula (1) is selected from

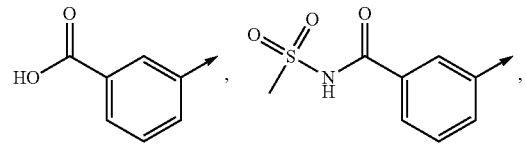

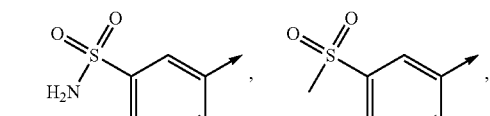

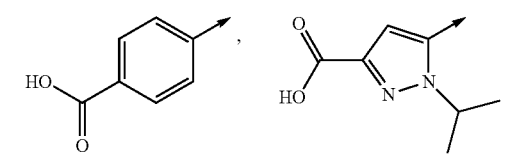

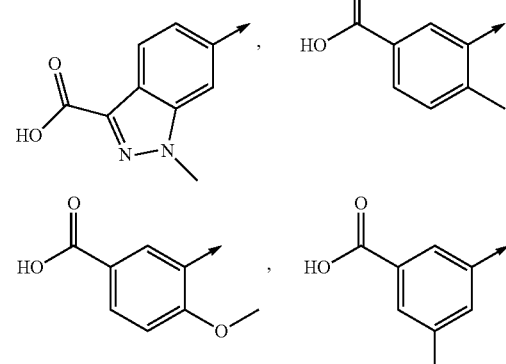

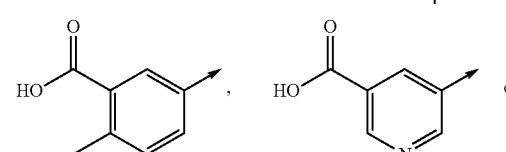

or

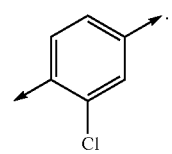

In another embodiment in combination with any of the above or below embodiments, Q in the compound according to Formula (1) is

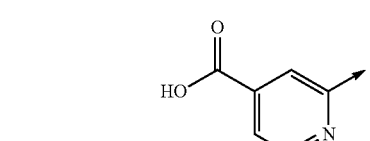

In another embodiment in combination with any of the above or below embodiments, Z in the compound according to Formula (1) is

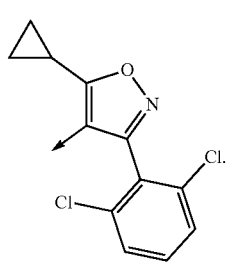
In another embodiment in combination with any of the above or below embodiments, the compound according to Formula (1) is selected from
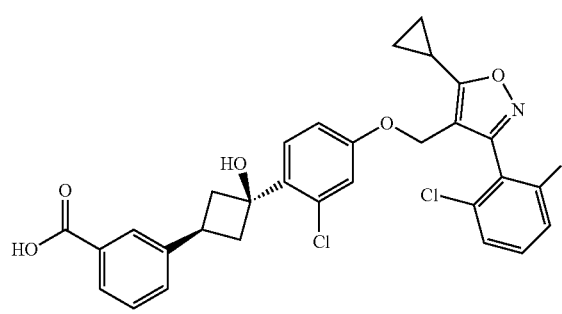
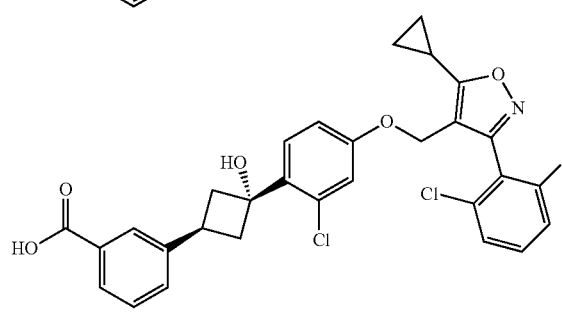
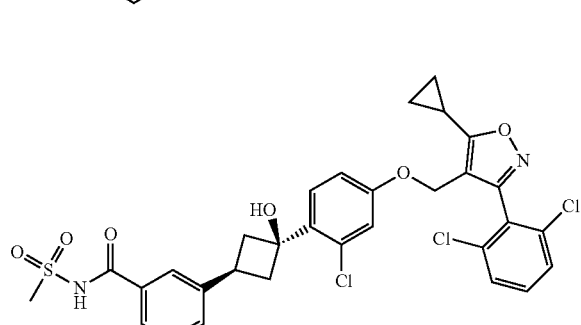
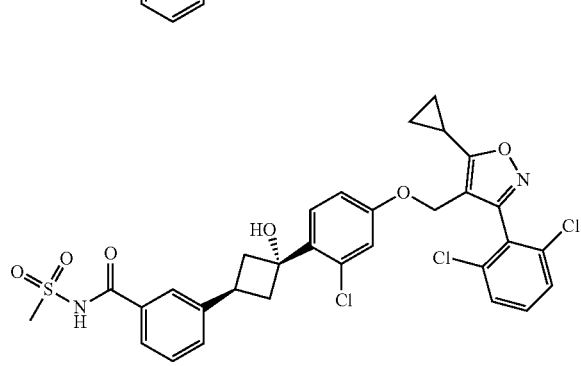
-continued
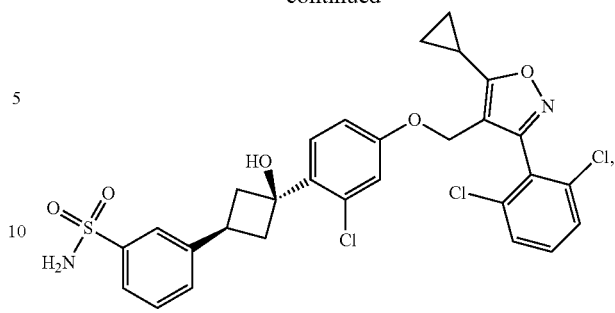
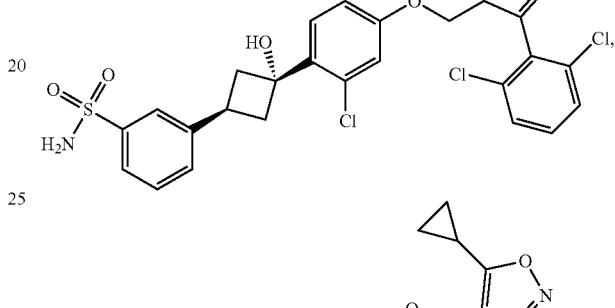
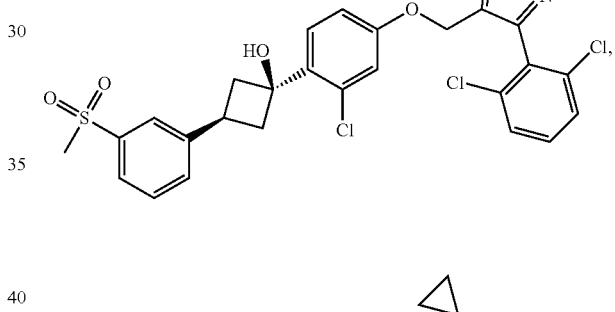
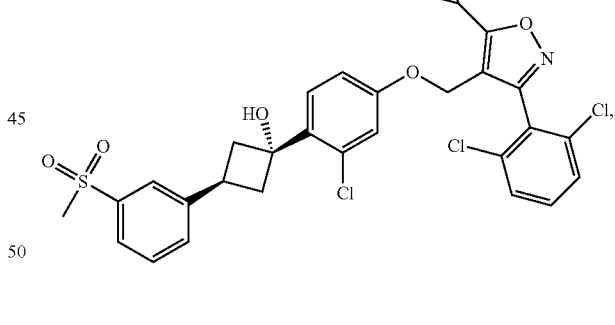
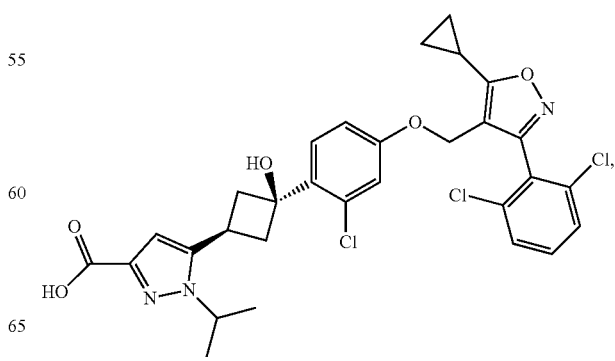

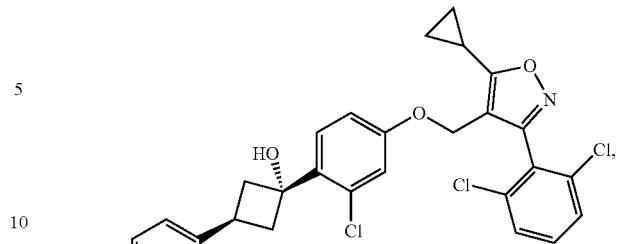
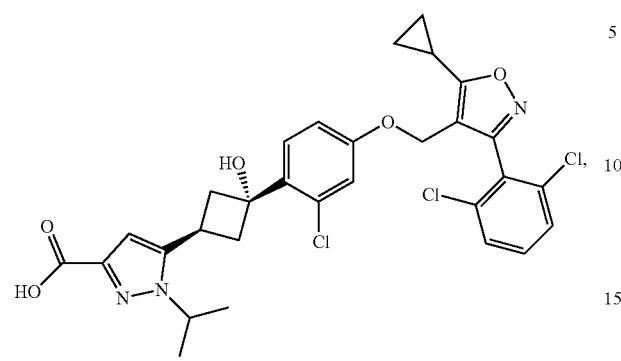
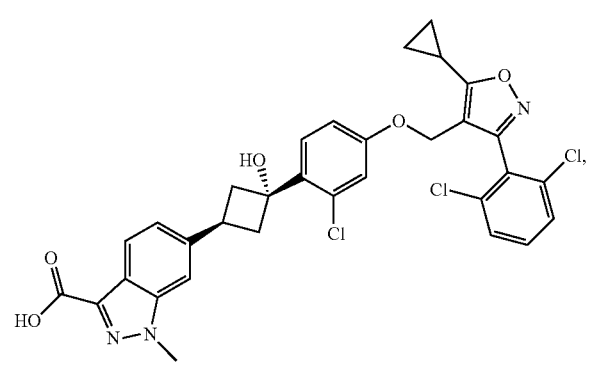
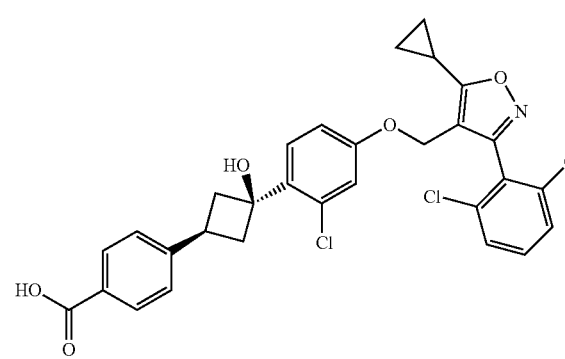

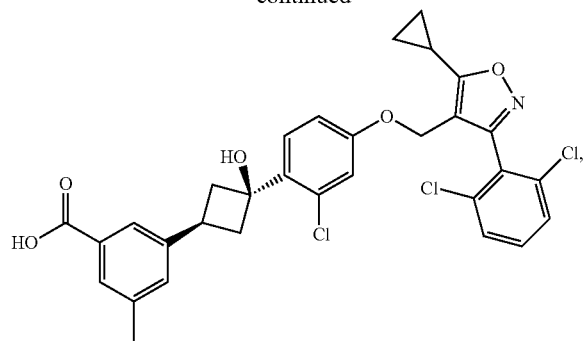
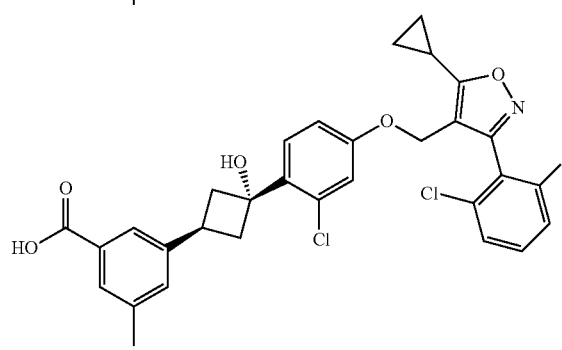
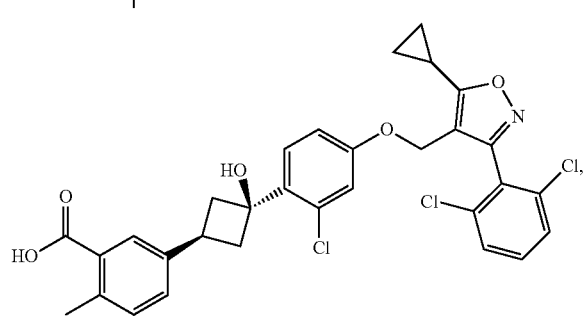
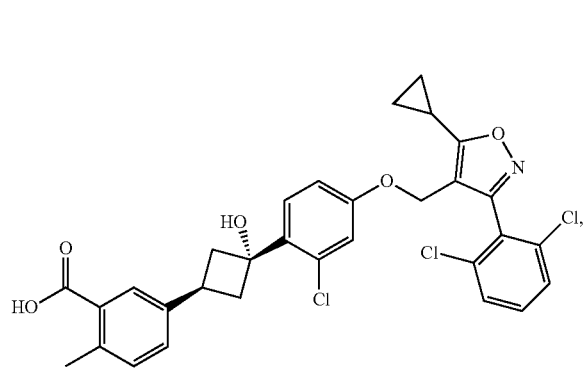
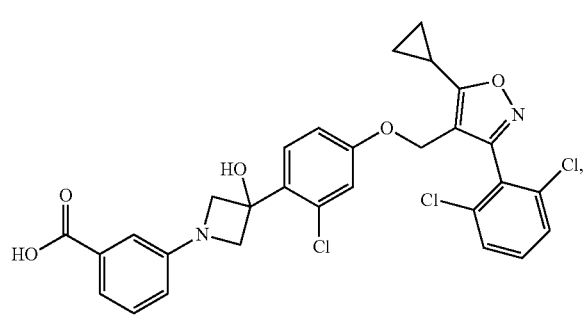

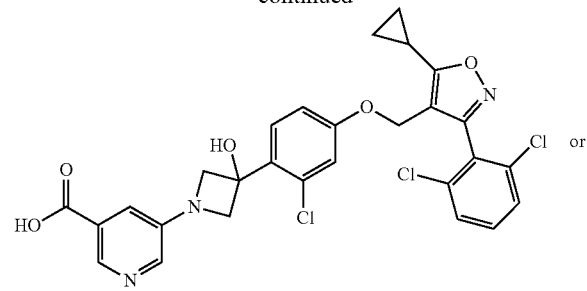
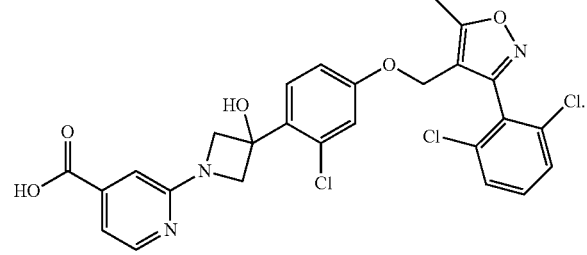
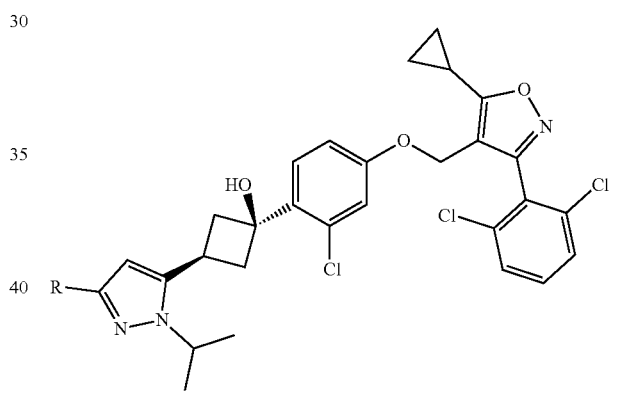

In another embodiment in combination with any of the above or below embodiments, the compound according to Formula (1) is

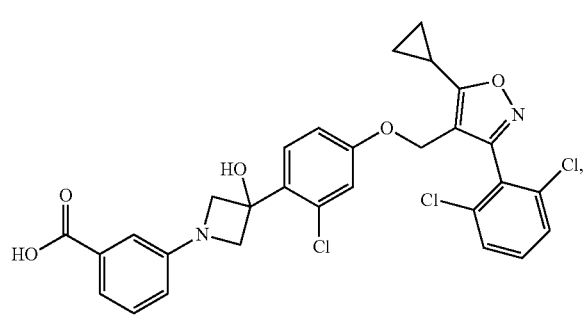

wherein R is selected from the group consisting of CO$_2$H, CONHSO$_2$Me, and tetrazolyl.

In another embodiment, the present invention is directed to a compound according to Formula (1) for use as a medicament.

In another embodiment, the present invention is directed to a compound according to Formula (1) for use in the prophylaxis and/or treatment of diseases mediated by FXR.

In another embodiment, the present invention is directed to the use of a compound according to Formula (1) for the preparation of a medicament for the prophylaxis and/or treatment of diseases mediated by FXR.

In another embodiment in combination with any of the above or below embodiments, the disease is selected from chronic intrahepatic or some forms of extrahepatic cholestatic conditions; liver fibrosis; obstructive or chronic inflammatory disorders of the liver; liver cirrhosis; liver steatosis and associated syndromes, cholestatic or fibrotic effects that are associated with alcohol-induced cirrhosis or with viral-borne forms of hepatitis; liver failure or liver ischemia after major liver resection; chemotherapy associated steatohepatitis (CASH); acute liver failure; and/or Inflammatory Bowel Diseases.

In another embodiment in combination with any of the above or below embodiments, the disease is selected from lipid and lipoprotein disorders; Type II Diabetes and clinical complications of Type I and Type II Diabetes, including diabetic nephropathy, diabetic neuropathy, diabetic retinopathy and other observed effects of clinically manifest long term Diabetes; conditions and diseases which result from chronic fatty and fibrotic degeneration of organs due to enforced lipid and specifically triglyceride accumulation and subsequent activation of profibrotic pathways, such as Non-Alcoholic Fatty Liver Disease (NAFLD), or Non-Alcoholic Steatohepatitis (NASH); obesity or metabolic syndrome (combined conditions of dyslipidemia, diabetes or abnormally high body-mass index); and/or cute myocardial infarction, acute stroke or thrombosis which occurs as an endpoint of chronic obstructive atherosclerosis.

In another embodiment in combination with any of the above or below embodiments, the disease is selected from non-malignant hyperproliferative disorders and malignant hyperproliferative disorders, specifically of hepatocellular carcinoma, colon adenoma and polyposis, colon adenocarcinoma, breast cancer, pancreas adenocarcinoma, Barrett's esophagus or other forms of neoplastic diseases of the gastrointestinal tract and the liver.

Figure 1A:
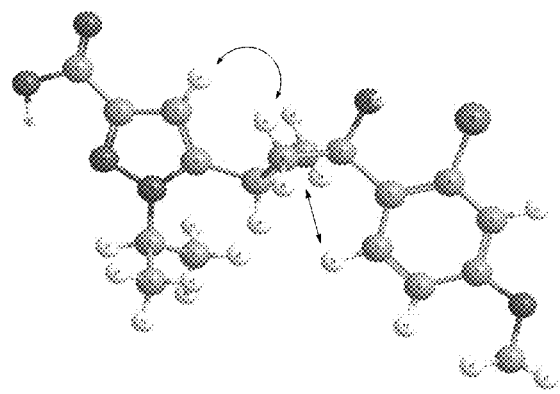
FIG. 1A: NOEs detected for example 8 with 1,3-trans transannular configuration of the aromatic moieties are shown with double arrows.

The improved physico-chemical properties have been achieved by the introduction of a polar hydroxyl group on a 1,3-cyclobutylidene or 1,3-azetidinylidene group replacing the former 1,2-cyclopropylidene ring.

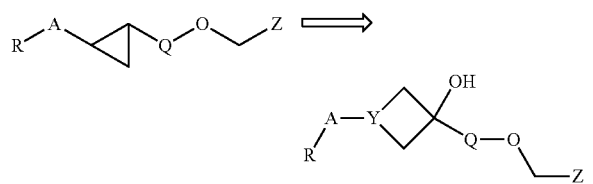

Surprisingly, the resulting compounds maintained their activity on the FXR receptor but demonstrated improved physico-chemical properties, such as higher aqueous solubility and/or membrane permeability.

The compounds of the present invention share a common chemical structure according to Formula (1) in claim 1.

In a preferred embodiment in combination with any of the above or below embodiments, the present invention is directed to an enantiomer, diastereomer or pharmaceutically acceptable salt of a compound according to Formula (1).

In a preferred embodiment in combination with any of the above or below embodiments, R in Formula (1) is selected from the group consisting of $COOR_6$, $CONR_7R_8$, $SO_2NR_7R_8$, and $SO_2$—$C_{1-6}$ alkyl.

In a preferred embodiment in combination with any of the above or below embodiments, $R_6$ in Formula (1) is H.

In a preferred embodiment in combination with any of the above or below embodiments, $R_7$ and $R_8$ in Formula (1) are independently from each other selected from the group consisting of H and $SO_2$—$C_{1-8}$ alkyl.

In a preferred embodiment in combination with any of the above or below embodiments, $R_7$ in Formula (1) is H.

In a preferred embodiment in combination with any of the above or below embodiments, $R_8$ in Formula (1) is $SO_2$—$C_{1-8}$ alkyl.

In a preferred embodiment in combination with any of the above or below embodiments, A is selected from the group consisting of phenyl, pyridyl, pyrimidyl, pyrazolyl, indazolyl, and oxadiazolyl.

In a preferred embodiment in combination with any of the above or below embodiments, A is substituted with one or two groups independently selected from $C_{1-6}$ alkyl, more preferably $C_{1-3}$ alkyl. In another preferred embodiment in combination with any of the above or below embodiments, A is unsubstituted.

In a preferred embodiment in combination with any of the above or below embodiments, Q is phenyl.

In a preferred embodiment in combination with any of the above or below embodiments, Q is substituted with one or two groups independently selected from halogen, more preferably one group selected from halogen, in particular Cl.

In a preferred embodiment in combination with any of the above or below embodiments, Z is

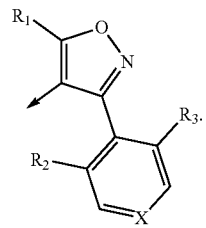

In a preferred embodiment in combination with any of the above or below embodiments, X=CH.

In a preferred embodiment in combination with any of the above or below embodiments, $R_1$ is $C_{3-6}$ cylcoalkyl, in particular cyclopropyl.

In a preferred embodiment in combination with any of the above or below embodiments, $R_2$ and $R_3$ are independently selected from halogen, in particular Cl.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carboxylate in a compound of the present invention is, for example, converted into an alkyl-, aryl-, choline-, amino, acyloxymethylester, linolenoylester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

The compounds of the present invention can be prepared by a combination of methods described in Schemes I to III. As depicted in Scheme I a 4-membered cyclic ketone, substituted with substituent A in the 3-position can react with a metalated aromatic or heteroaromatic ring M-Q-O—CH$_2$Z (M=metal, e.g. Li) in aprotic solvents and preferably at low temperatures to afford a hydroxyl substituted 4-membered ring bearing the substituents A and Q. In the case where Y is CH two isomers can form (A and Q transannular cis or trans to each other). Under optimized conditions the formation of mainly one of the two isomers can be achieved. The two isomers can be separated by appropriate methods known in the art like e.g. silica gel chromatography or preparative RP-HPLC.

Scheme I

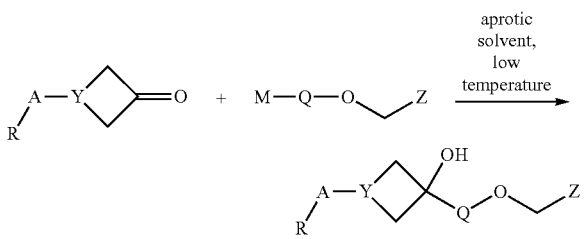

In Scheme II the methods are summarized which are used to prepare the 4-membered cyclic ketones needed for the synthesis of the compounds of this invention. In option a) a vinyl bearing intermediate, e.g. prepared by vinylation of a corresponding halogen-containing starting material R-A-X (X=halogen) can react with in situ formed α,α-dichloro ketene to form a 2,2-dichlorocyclobutanone. After dehalogenation, e.g. with Zn in acetic acid under reflux, the desired 3-substituted cyclobutanones are obtained. Alternatively, the vinyl-intermediates can react with in situ generated unsubstituted ketene to afford in one step the desired cyclobutanone intermediates. In option b) 3-methylenecyclobutanecarbonitrile is used as starting material. Substituted heterocycles can be built up from the cyano group in several steps by methods known to those skilled in the art. The desired cyclobutanones can be obtained by oxidative cleavage of the exocyclic double bond using conditions and reagents known to those skilled in the art, e.g. by the use of OsO$_4$, ozone or RhCl$_3$/NaIO$_4$ as oxidants. Option c) shows the methods used to prepare the substituted azetidinones. Cu- or Pd-catalysed C—N cross coupling between 3-hydroxy-azetidine and halo-aromatic or halo-heteroaromatic rings afford the corresponding N-substituted 3-hydroxy-azetidines which can be transformed into the desired azetidinones by oxidation.

As a result, the present invention relates to compounds according to the general Formula (1) which bind to FXR and act as agonists or modulators of FXR.

The invention further relates to the use of said compounds for the treatment and/or prophylaxis of diseases and/or conditions through binding of said nuclear receptor by said compounds. Further the present invention relates to the use of said compounds for the preparation of a medicament for the treatment and/or prophylaxis of diseases and/or conditions through binding of said nuclear receptor by said compounds. Specifically, the present invention relates to the use of compounds according to Formula (1) in the preparation of a medicament for the prophylaxis and/or treatment of chronic intrahepatic or some forms of extrahepatic cholestatic conditions, of liver fibrosis, of acute intraheptic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and

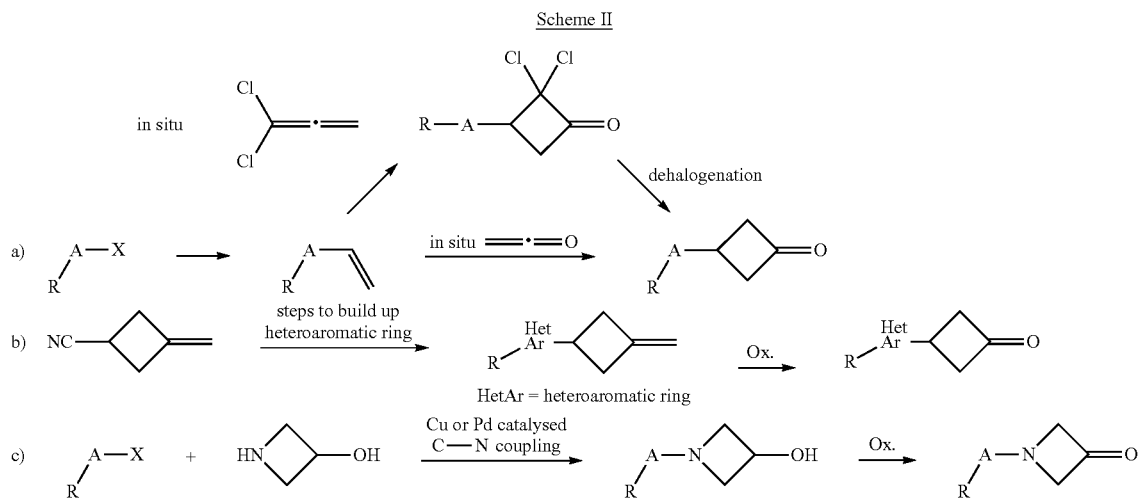

Scheme III illustrates some possibilities to perform modifications of the substituents at the A group after the formation of the 4-membered hydroxy-bearing rings. For example, a leaving group X (e.g. bromide) can be substituted by a cyano group, a carboxylic ester, methylsulfonyl or thioether by transition metal catalysed cross coupling reactions. The obtained derivatives can be further transformed into other derivatives by methods known to those skilled in the art. For example, the cyano and the ester group can be hydrolysed under basic conditions to the afford a carboxylic acid which in turn can be transformed into acyl-sulfonamides. A benzyl thioether can be chlorinated to afford the chlorosulfonyl intermediate which reacts with ammonia to the corresponding sulfonamides.

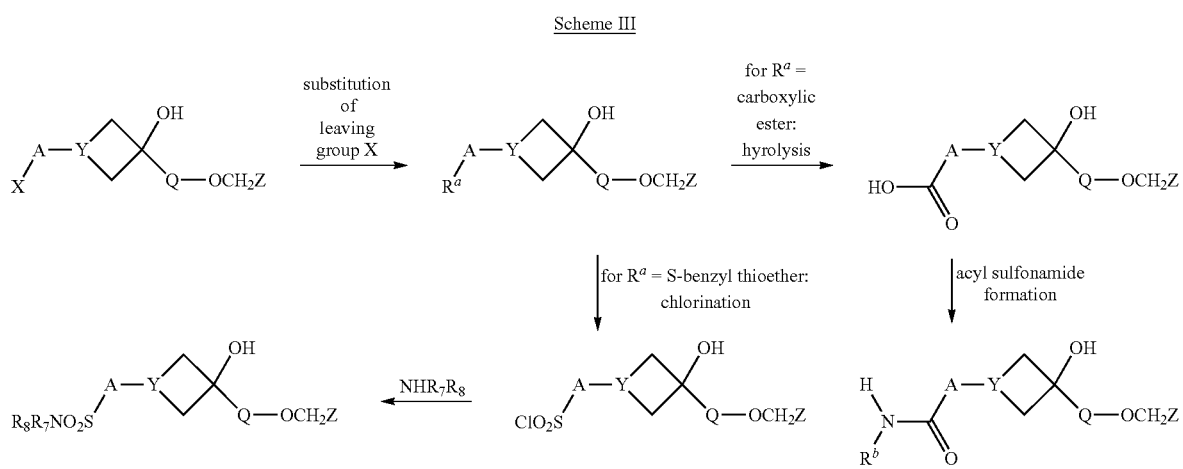

subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistant infections by intracellular bacteria or parasitic protozoae, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis.

Medicaments as referred to herein may be prepared by conventional processes, including the combination of a compound according to the present invention and a pharmaceutically acceptable carrier.

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (T. Claude) et al., Arterioscler. Thromb. Vasc. Biol. 2005, 25, 2020; Y. D. Wang et al., Cell Res. 2008, 18, 1087.

FXR regulates a complex pattern of response genes in the liver and in the gastrointestinal tract. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or CDCA, this can be regarded as an example of feedback inhibition on the gene expression level (B. Goodwin et al., Mol. Cell 2000, 6, 517; T. T. Lu et al., Mol. Cell 2000, 6, 507). Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice (C. J. Sinal et al., Cell 2000, 102, 731). where under- or overexpression of several ABC-transporters in the liver was shown. Further detailed analysis revealed that the major bile salt excretory pump BSEP or ABCB11 (M. Ananthanarayanan et al., J. Biol. Chem. 2001, 276, 28857; J. R. Plass et al., Hepatology 2002, 35, 589) as well as the key enzyme which mediates lipid transfer from lipoproteins to phospholipids, PLTP (N. L. Urizar et al., J. Biol. Chem. 2000, 275, 39313), and the two key canalicular membrane transporters for phospholipids, MRP-2 (ABCC4) (H. R. Kast et al., J. Biol. Chem. 2002, 277, 2908) and MDR-3 (ABCB4); L. Huang et al., J. Biol. Chem. 2003, 278, 51085) are direct targets for ligand-directed transcriptional activation by FXR (summarized in: M. Miyata, J. Pharmacol. Exp. Ther. 2005, 312, 759; G. Rizzo et al., Curr. Drug Targets Immune Endocr. Metabol. Disord. 2005, 5, 289).

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 (P. R. Maloney et al., J. Med. Chem. 2000, 43, 2971; T. M. Willson et al., Med. Res. Rev. 2001, 21, 513) as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated (R. Pellicciari et al., J. Med. Chem. 2002, 45, 3569; Y. Liu et al., J. Clin. Invest. 2003, 112, 1678). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 in hepatic stellate cells and the subsequent reduction of alpha-collagen mRNA and Transforming growth factor beta (TGF-beta) mRNA which are both pro-fibrotic factors by FXR agonists (S. Fiorucci et al., Gastroenterology 2004, 127, 1497; S. Fiorucci et al., J. Pharmacol. Exp. Ther. 2005, 314, 584). Furthermore, anti-cholestatic activity was demonstrated in bile-duct ligated animal models as well as in animal models of estrogen-induced cholestasis (S. Fiorucci et al., J. Pharmacol. Exp. Ther. 2005, 313, 604).

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al., Gastroenterology 2004, 126, 756; L. Alvarez et al., Hum. Mol. Genet. 2004, 13, 2451) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: G. Rizzo et al., Curr. Drug Targets Immune Endocr. Metabol. Disord. 2005, 5, 289; G. Zollner et al., Mol. Pharm. 2006, 3, 231; S. Y. Cai et al., Expert Opin. Ther. Targets 2006, 10, 409).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease (H. Wittenburg, Gastroenterology 2003, 125, 868). Using the synthetic FXR tool compound GW4064 it could be demonstrated that activation of FXR leads to an improvement of the Cholesterol Saturation Index (CSI) and directly to an abolishment of gallstone formation in C57L gallstone susceptible mice whereas drug treatment in FXR knockout mice shows no effect on gallstone formation (A. Moschetta et al., Nature Medicine 2004, 10, 1352).

These results qualify FXR as a good target for the development of small molecule agonists that can be used to prevent cholesterol gallstone formation or to prevent reformation of gallstones after surgical removal or shockwave lithotripsy (discussed in: S. A. Doggrell, Curr. Opin. Investig. Drugs 2006, 7, 344).

Thus, in one embodiment of the invention, the compound according to Formula (1) and pharmaceutical compositions comprising said compound is used for the prophylaxis and/or treatment of obstructive or chronic inflammatory disorders that arise out of improper bile composition such as cholelithiasis also known as cholesterol gallstones.

Beyond its strong hepatoprotective and choleretic as well as anti-fibrotic effects that FXR shows upon small molecule stimulated activation in the liver, FXR seems to have a role in protecting the intestine from neoplastic transformation and from the development of polyps and their transition into adenocarcinoma in the gut (S. Modica et al., Cancer Res. 2008, 68, 9589 and R. R. Maran et al., J. Pharmacol. Exp. Ther. 2009, 328, 469). Similar to the situation in the intestine absence of FXR leads to a high increase in the formation of Hepatocellular Cacrcinoma (HCC), the most prominent form of liver cancer (I. Kim et al., Carcinogenesis 2007, 28, 940 and F. Yang et al., Cancer Res. 2007, 67, 863). Whereas a functional FXR prevents the formation of colon adenocarcinoma and hepatocellular carcinoma, FXR activation induces liver regeneration after hepatectomy (W. Huang et al., Science 2006, 312, 233).

The combined hepatoprotective, anti-neoplastic and liver regenerative effects associated with FXR activation can be therapeutically exploited for the use of FXR agonists in the treatment of sever liver diseases. In one embodiment, the compounds according to the invention and pharmaceutical compositions comprising said compounds are used in the treatment of liver diseases such as HCC, stimulation of liver regrowth and amelioration of side effects associated with major liver resection, liver cirrhosis independent of the etiology and prevention or treatment of liver ischemia in the course of liver transplantation or major liver surgery.

Since the discovery of the first synthetic FXR agonist and its administration to rodents it became evident that FXR is a key regulator of serum triglycerides (P. Maloney et al., J. Med. Chem. 2000, 43, 2971; T. Willson et al., Med. Res. Rev. 2001, 21, 513). Over the past six years accumulating evidence has been published that activation of FXR by synthetic agonists leads to significant reduction of serum triglycerides, mainly in the form of reduced VLDL, but also to reduced total serum cholesterol (H. R. Kast et al., Mol. Endocrinol. 2001, 15, 1720; N. L. Urizar et al., Science 2002, 296, 1703; G. Lambert et al., J. Biol. Chem. 2003, 278, 2563; M. Watanabe et al., J. Clin. Invest. 2004, 113, 1408; A. Figge et al., J. Biol. Chem. 2004, 279, 2790; S. Bilz et al., Am. J. Physiol. Endocrinol. Metab. 2006, 290, E716).

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (K. R. Stayrook et al., Endocrinology 2005, 146, 984; Y. Zhang et al., PNAS 2006, 103, 1006; B. Cariou et al., J. Biol. Chem. 2006, 281, 11039; K. Ma et al., J. Clin. Invest. 2006, 116, 1102; D. Duran-Sandoval et al., Biochimie 2005, 87, 93). An effect on reduction of body weight was also recently observed in mice overfed with a high lipid diet (C. Lihong et al., American Diabetes Association (ADA) 66th annual scientific sessions, June 2006, Abstract Number 856-P). This weight loss effect might results from FXR's induction of FGF-19, a fibroblast growth factor that is known to lead to weight loss and athletic phenotype (J. Holt et al., Genes Dev. 2003, 17, 1581; E. Tomlinson et al., Endocrinology 2002, 143, 1741). In recent patent applications, the effect of FXR agonist on reduction of body weight was demonstrated (WO 2004/087076; WO 2003/080803).

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the invention and pharmaceutical compositions comprising said compounds are used in the prophylaxis and/or treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the prophylaxis and/or treatment of chronic intrahepatic, such as PBC, PSC, progressive familiar cholestasis (PFIC), alcohol-induced cirrhosis and associated cholestasis, and some forms of extrahepatic cholestatic conditions, or liver fibrosis.

The invention also relates to a compound of Formula (1) or to a pharmaceutical composition comprising said compound for the prophylaxis and/or treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for preventing and/or treating a disease selected from the group consisting of lipid and lipoprotein disorders such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the prophylaxis and/or treatment of diseases where the combined lipid lowering, anti-cholestatic and anti-fibrotic effects of FXR-targeted medicaments can be exploited for the treatment of liver steatosis and associated syndromes such as NASH, or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice (E. A. Hanniman et al., J. Lipid Res. 2005, 46, 2595). Therefore, FXR agonists might have clinical utility as anti-atherosclerotic and cardioprotective drugs. The downregulation of Endothelin-1 in Vascular Smooth Muscle Cells might also contribute to such beneficial therapeutic effects (F. He et al., Circ. Res. 2006, 98, 192).

The invention also relates to a compound according to Formula (1) or a pharmaceutical composition comprising said compound for preventive and posttraumatic treatment of cardiovascular disorders such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells (K. E. Swales et al., Cancer Res. 2006, 66, 10120 and F. Journe et al., Breast Cancer Res. Treat. 2009, 115, 523).

This would allow to regard FXR also as a potential target for the treatment of proliferative diseases, especially metastasizing cancer forms that express a small molecule responsive form of FXR.

In a further embodiment, said compounds and pharmaceutical compositions are used for the prophylaxis and/or treatment of malignant hyperproliferative disorders such as different forms of cancer, specifically certain forms of breast, liver or colon cancer where interference with an FXR ligand will have a beneficial impact.

Finally, FXR seems also to be involved in the control of antibacterial defense in the intestine (T. Inagaki et al., PNAS. 2006, 103, 3920) although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the invention also relates to a compound according to Formula (1) or a pharmaceutical composition comprising said compound for preventing and/or treating a disease related to Inflammatory Bowel Diseases such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the prophylaxis and/or treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In a further embodiment, the compounds or pharmaceutical composition of the present invention are useful in preventing and/or treating clinical complications of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of Diabetes are also encompassed by the present invention.

Furthermore, conditions and diseases which result from chronic fatty and fibrotic degeneration of organs due to enforced lipid and specifically triglyceride accumulation and subsequent activation of profibrotic pathways may also be prevented and/or treated by applying the compounds or pharmaceutical composition of the present invention. Such conditions and diseases encompass NASH and chronic cholestatic conditions in the liver, Glomerulosclerosis and Diabetic Nephropathy in the kidney, Macula Degeneration and Diabetic Retinopathy in the eye and Neurodegenerative diseases such as Alzheimer's Disease in the brain, or Diabetic Neuropathies in the peripheral nervous system.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Since the compounds of the present invention mostly represent carboxylic acids or similar anionic isosters thereof, and since it is well known that salt forms of ionic drug compounds can substantially affect the bioavailability of drug compounds, the compounds of the present invention may also be used as salts with various countercations to yield an orally available formulation. Such pharmaceutically acceptable cations may be amongst others mono- or bivalent ions such as ammonium, the alkaline metals sodium or potassium or the alkaline earth metals magnesium or calcium, certain pharmaceutically acceptable amines such as tris(hydroxymethyl)aminomethane, ethylendiamine, diethylamine, piperazine or others, or certain cationic amino acids such as lysine or arginine.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described above.

The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present invention is shown below. Unless otherwise indicated in the schemes, the variables have the same meaning as described above. The examples presented below are intended to illustrate particular embodiments of the invention. Suitable starting materials, building blocks and reagents employed in the synthesis as described below are commercially available from Sigma-Aldrich or Acros Organics, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

EXAMPLES

Example 1: Methyl 3-((1s,3s)-3-(2-chloro-4-((5-cyclopropyl-3-(2,6-dichlorophenyl)isoxazol-4-yl)methoxy)phenyl)-3-hydroxycyclobutyl)benzoate (1)

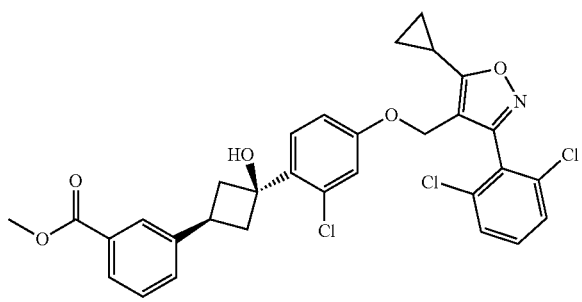 [SMILES: COC(=O)c1cccc([C@H]2C[C@](O)(c3ccc(OCc4c(-c5c(Cl)cccc5Cl)noc4C4CC4)cc3Cl)C2)c1]

Step 1: 4-((4-Bromo-3-chlorophenoxy)methyl)-5-cyclopropyl-3-(2,6-dichlorophenyl)-isoxazole (1a)

To a solution of (5-cyclopropyl-3-(2,6-dichlorophenyl)isoxazol-4-yl)methanol (13 g, 45.8 mmol) in $CH_2Cl_2$ (DCM) (200 mL) was added dropwise $SOCl_2$ (40 mL, 336 mmol). The resulting mixture was stirred at rt for 2 h and the solvents were removed under reduced pressure. The residue was dissolved in N,N-dimethylformamide (DMF) (200 ml) and 4-bromo-3-chlorophenol (9.7 g, 47 mmol), $K_2CO_3$ (40 g, 290 mmol) and NaI (12 g, 80 mmol) were added to this solution. The mixture was stirred at 60° C. overnight, then cooled to rt, diluted with water (1000 mL) and extracted with ethyl acetate (EA) (500 mL×3). The combined organic phases were washed with brine (500 mL×3), dried over $Na_2SO_4$ and concentrated in vacuo. The residue was purified by flash chromatography on silica gel (CC) to give the title compound 1a (19 g, 88%) as a white solid.

Step 1: Methyl 3-(2,2-dichloro-3-oxocyclobutyl)benzoate (1b)

To a 3-necked round bottomed flask, under a nitrogen atmosphere, fitted with a condenser, an overhead stirrer and pressure equalised dropping funnel was dissolved methyl 3-vinylbenzoate (5 g, 31 mmol) in dry $Et_2O$ (150 mL). To this flask was added zinc dust (6 g, 3 eq) and the reaction was sonicated for 30 min. After this time a solution of trichloroacetylchloride (8.7 mL, 2.5 eq) in dry $Et_2O$ (50 mL) was added dropwise whilst continuing the sonication over the next 30 min. During the process the reaction mixture was heated to 35° C. The sonication was continued for 2.5 h at reflux and the reaction appeared to be complete by $^1$H NMR analysis. The reaction was allowed to cool to rt and quenched with water (~50 mL). This was done in a dropwise manner interspersed sveral times by a few minutes since a delayed exothermic reaction occurred. After 20 min stirring in water the reaction mixture was filtered through a pad of celite and rinsed through with $Et_2O$. The organic layer was washed with portions of water (2×250 mL), saturated sodium bicarbonate (2×250 mL) and brine (1×250 mL), dried over sodium sulfate, filtered and concentrated under reduced pressure to afford the crude product 1b as a dark yellow thick oil (crude 8.7 g).

Step 2: Methyl 3-(3-oxocyclobutyl)benzoate (1c)

Crude compound 1b (8.7 g) was dissolved in glacial acetic acid (55 mL) in a round bottomed flask under a nitrogen atmosphere. To this flask was added zinc dust (4.6 g, 2.2 eq) and the reaction was stirred and heated to 120° C. for 3 h. After cooling to rt the mixture was filtered though a pad of celite, this was washed with portions of EA. The combined solution was concentrated under reduced pressure before being dissolved in EA (500 mL), washed with brine (150 mL×2) and then dried over sodium sulfate, filtered and concentrated again. The crude mixture was stirred for 5 min in chloroform (250 mL) and filtered through a sintered funnel. The filtrate was concentrated to give the crude product as a pale yellow oil. The crude product was purified by CC in (PE/EA=9:1, PE=petroleum ether) to give the desired product 1c (2.5 g, 38% for 2 steps) as a pale yellow oil.

Step 3: Methyl 3-(3-(2-chloro-4-((5-cyclopropyl-3-(2,6-dichlorophenyl)isoxazol-4-yl)methoxy)phenyl)-3-hydroxycyclobutyl)benzoate (1)

To a stirring solution of compound 1a (1.67 g, 3.5 mmol) in dry THF (30 mL) was added n-BuLi (2.5 M in hexane, 1.2 eq, 1.69 mL) dropwise over 10 min at −78° C. under a nitrogen atmosphere. This was stirred for 1 h at this temperature before adding a solution of compound 1c (0.72 g, 1 eq) in dry THF (10 mL) dropwise and stirred for 1 h at this temperature. The reaction mixture was allowed to warm to rt slowly and left stirring overnight. The reaction was quenched with a solution of saturated ammonium chloride solution (50 mL) and EA (250 mL). The organic layer was separated and the aq. layer was washed with EA (2×100 mL). The combined organic extracts were dried over sodium sulfate, filtered and concentrated to give the crude product as a brown oil. The product was isolated following CC with PE/EA (19:1 to 3:1). The reaction and purification was repeated twice on the same scale and the combined product (3.13 g) was repurified under the same conditions to afford the final product 1 (1.7 g, 19%). $^1$H NMR (CDCl$_3$): 7.93 (m, 1H), 7.90-7.85 (m, 1H), 7.50-7.30 (m, 5H), 6.88 (s, 1H), 6.75-6.72 (m, 1H), 4.80 (s, 2H), 3.88 (s, 3H), 3.20-3.10 (m, 1H), 3.00-2.91 (m, 2H), 2.60-2.49 (m, 2H), 2.15-2.08 (m, 1H), 1.30-1.25 (m, 2H), 1.15-1.10 (m, 2H).

Example 2: 3-((1s,3s)-3-(2-Chloro-4-((5-cyclopropyl-3-(2,6-dichlorophenyl)isoxazol-4-yl)methoxy)phenyl)-3-hydroxycyclobutyl)benzoic acid (2)

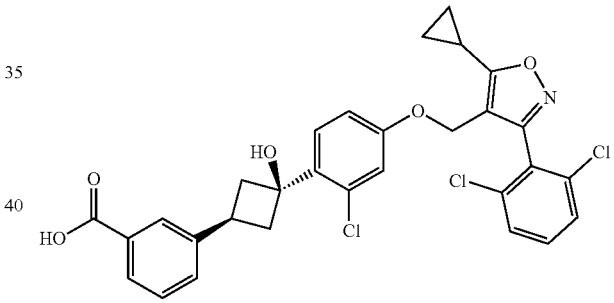

Compound 1 (1.7 g, 2.84 mmol) was dissolved in THF (100 mL) at rt. A solution of LiOH (285 mg, 4.2 eq) in water (20 mL) was added and the solution was stirred and warmed to 35° C. for three days. After this time the THF was removed under reduced pressure. The remaining aq. solution was diluted with water (25 mL) and washed with $Et_2O$ (2×50 mL). The aq. layer was then transferred to a round bottomed flask and acidified to pH 6 using 1N HCl. The formed white precipitated was filtered off and dried under reduced pressure at 50° C. to give title compound 2 (1.3 g, 78%, single isomer by $^1$H-NMR and LC-MS) as white solid. $^1$H NMR (400 MHz, $CD_3OD$) δ: 7.98 (s, 1H), 7.86 (d, J=7.6 Hz, 1H), 7.58-7.46 (m, 5H), 7.41 (t, J=7.6 Hz, 1H), 6.91 (d, J=2.4 Hz, 1H), 6.80 (dd, J=8.8, 2.4 Hz, 1H), 4.95 (s, 2H), 3.29-3.25 (m, 2H), 2.96 (m, 1H), 2.55-2.49 (m, 2H), 2.37 (m, 1H), 1.24-1.22 (m, 4H). MS (ESI) m/z: 584 (582) [M−1]$^-$.

Relevant intensive NOEs (obtained from the ROESY spectra; arrows below) indicate that the two aromatic moieties are 1,3-trans oriented in Example 2.

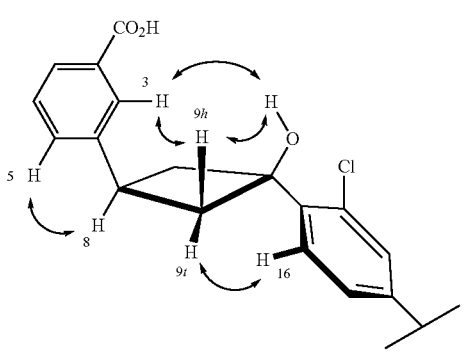

Alternative Route to Example 2

Step 1: 3-(3-Bromophenyl)cyclobutanone (2a)

N,N-Dimethylacetamide (9.0 g, 103 mmol) was dissolved in 1,2-dichloroethane (200 mL). The solution was cooled to 0° C. before trifluoromethanesulfonic anhydride (63 g, 223 mmol) was added. The reaction was stirred for an additional 60 min at 0° C. Then 1-bromo-3-vinylbenzene (15 g, 81.9 mmol) and 2,4,6-collidine (10.5 g, 86.6 mmol) were added. The reaction was heated to reflux overnight, quenched by addition of water (300 mL) and stirred for 2 hr at rt. The mixture was extracted with DCM (300 mL×3). The combined organic layers were dried over $Na_2SO_4$ and concentrated in vacuo. Purification by CC (EA/PE=1:20) gave the title compound 2a (5.0 g, 27%) as a pale yellow solid.

Step 2: 3-(3-Bromophenyl)-1-(2-chloro-4-((5-cyclopropyl-3-(2,6-dichlorophenyl)isoxazol-4-yl)methoxy)phenyl)cyclobutanol (2b)

To a solution of compound 1a (14 g, 29.6 mmol) in dry THF (500 ml) at −78° C. was added dropwise n-BuLi (18.5 mL, 1.6 M in hexane, 29.6 mmol). The mixture was stirred for an additional 1 h at −78° C. and a solution of compound 2a (6.5 g, 28.9 mmol) in dry THF (50 mL) was added dropwise. The resulting mixture was stirred at −78° C. for 1 h and then warmed to rt and quenched with saturated aq. $NH_4Cl$ (500 mL). The mixture was extracted with EA (500 mL×2), the combined organic layers were washed with brine, dried over $Na_2SO_4$ and concentrated in vacuo. The residue was purified by CC (EA/PE=1:5) to give the title compound 2b (6.5 g, 37%) as a white solid.

Step 3: 3-(3-Cyanophenyl)-1-(2-chloro-4-((5-cyclopropyl-3-(2,6-dichlorophenyl)isoxazol-4-yl)methoxy)phenyl)cyclobutanol (2c)

To a solution of compound 2b (3.1 g, 5 mmol) in DMF (50 mL) were added under argon atmosphere $Zn(CN)_2$ (500 mg, 4.3 mmol), $Pd_2(dba)_3$ (300 mg, 0.33 mmol) and Xantphos (150 mg, 0.31 mmol). The mixture was stirred for 10 h at 115° C. under microwave irradiation. After cooling to rt the reaction mixture was diluted with water (250 mL) and extracted with EA (250 mL×2). The combined organic layers were washed with brine (100 mL×3) and dried over $Na_2SO_4$. The residue was purified by CC (EA/PE) to give the title compound 2c (1.2 g, 42%) as a pale yellow solid.

Step 4: 3-((1s,3s)-3-(2-Chloro-4-((5-cyclopropyl-3-(2,6-dichlorophenyl)isoxazol-4-yl)methoxy)phenyl)-3-hydroxycyclobutyl)benzoic acid (2)

To a solution of compound 2c (15 g, 24.2 mmol) in EtOH (750 mL) was added aq. NaOH (40 g in 100 mL of water). The resulting mixture was heated to reflux overnight and then cooled to rt. The reaction was concentrated in vacuo to remove the volatile solvent, diluted with water (1000 mL) and the pH was adjusted to 2 with diluted aq. HCl (1N). The formed precipitate was collected by filtration to give the crude product as a yellow solid (13.8 g). Purification by preparative preversed phase HPLC (RP-HPLC) afforded the title compound 2 (8.0 g, 56%, single isomer by $^1$H-NMR) as a white solid.

Preparative Example 3

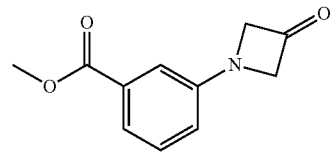

Step 1: Methyl 3-(3-hydroxyazetidin-1-yl)benzoate (3a)

To a solution of methyl 3-iodobenzoate (4.5 g, 17.2 mmol) in DMSO (30 mL) was added 3-azetidin-3-ol hydrogen chloride salt (1.3 g, 11.8 mmol), $Cs_2CO_3$ (9.5 g, 29.2 mmol), CuI (446 mg, 2.3 mmol) and L-proline (540 mg, 4.7 mmol) and then the mixture was heated at 90° C. for 18 h under argon atmosphere. The solution was diluted with EA and water and the organic layer was washed with brine three times, concentrated under reduced pressure and purified by CC (PE/EA=2:1) to give compound 3a (1.6 g, 66%) as a yellow solid.

Step 2: Methyl 3-(3-oxoazetidin-1-yl)benzoate (3)

To a solution of compound 3a (1.60 g, 7.7 mmol) in dry DCM (30 mL) was added Dess-Martin periodinane (6.5 g, 15.4 mmol) at 0° C. and the mixture was stirred at rt for 2 h under $N_2$ atmosphere. The mixture was quenched with saturated sodium bicarbonate solution and diluted with EA. The organic portion was washed with brine, dried over $Na_2SO_4$, filtered, concentrated under reduced pressure and purified by CC (PE/EA=4:1) to give compound 3 (1.2 g, 75%) as a white solid.

Example 4: 3-((1s,3s)-3-(2-Chloro-4-((5-cyclopropyl-3-(2,6-dichlorophenyl)isoxazol-4-yl)methoxy)phenyl)-3-hydroxycyclobutyl)-N-(methylsulfonyl)benzamide (4)

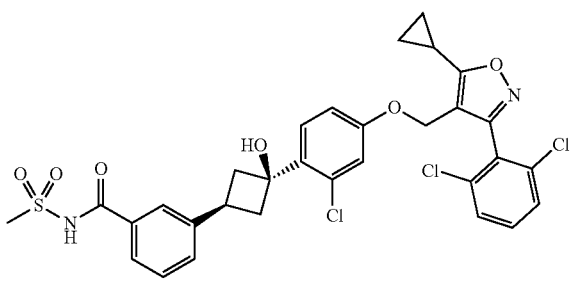 [SMILES: CS(=O)(=O)NC(=O)c1cccc([C@H]2C[C@](O)(c3ccc(OCc4c(-c5c(Cl)cccc5Cl)noc4C4CC4)cc3Cl)C2)c1]

To the solution of compound 2 (100 mg, 0.17 mmol) in DCM (5 mL) were added EDCl.HCl (100 mg, 0.52 mmol), DMAP (100 mg, 0.81 mmol) and MeSO$_2$NH$_2$ (40 mg, 0.42 mmol). The mixture was stirred at 30° C. overnight and then diluted with EA and washed by H$_2$O, brine and dried over Na$_2$SO$_4$. Concentration in vacuo and purification by prep-TLC gave crude target compound as a light yellow solid. RP-HPLC purification afforded the title compound 4 (38 mg, 33%) as a white solid. $^1$H NMR (400 MHz, CD$_3$OD) δ: 7.87 (s, 1H), 7.74 (d, J=7.6 Hz, 1H), 7.61-7.53 (m, 4H), 7.50-7.46 (m, 2H), 6.91 (d, J=2.4 Hz, 1H), 6.80 (dd, J=8.8, 2.4 Hz, 1H), 4.95 (s, 2H), 3.38 (s, 3H), 3.30-3.26 (m, 2H), 3.01 (m, 1H), 2.57-2.51 (m, 2H), 2.37 (m, 1H), 1.25-1.23 (m, 4H). MS (ESI) m/z: 659 [M−1]$^-$.

Example 5: 3-(3-(2-Chloro-4-((5-cyclopropyl-3-(2,6-dichlorophenyl)isoxazol-4-yl)methoxy)phenyl)-3-hydroxycyclobutyl)benzenesulfonamide (5)

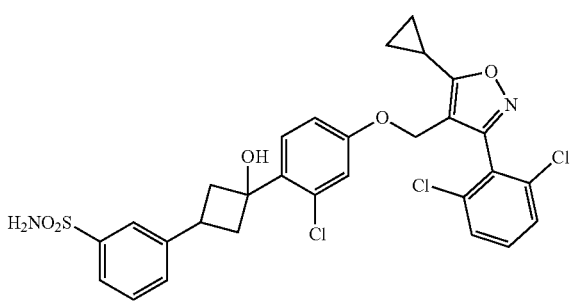 [SMILES: NS(=O)(=O)c1cccc(C2CC(O)(c3ccc(OCc4c(-c5c(Cl)cccc5Cl)noc4C4CC4)cc3Cl)C2)c1]

Step 1: 3-(3-(Benzylthio)phenyl)-1-(2-chloro-4-((5-cyclopropyl-3-(2,6-dichlorophenyl)isoxazol-4-yl)methoxy)phenyl)cyclobutanol (5a)

To a solution of compound 2b (619 mg, 1 mmol) in toluene (20 mL) under argon atmosphere were added K$_2$CO$_3$ (276 mg, 2 mmol), phenylmethanethiol (125 mg, 1 mmol), Pd$_2$(dba)$_3$ (200 mg, 0.22 mmol) and Xantphos (75 mg, 0.16 mmol). Then the mixture was stirred at 115° C. for 4 h. After being cooled to rt, the reaction was diluted with water (100 mL) and extracted with EA (100 mL×2). The combined organic layers were washed with brine (100 mL×2), dried over Na$_2$SO$_4$ and concentrated to dryness. Purification by CC gave compound the compound 5a (200 mg; 30%) as a pale yellow solid. $^1$H NMR (400 MHz, CDCl$_3$) δ: 7.36-7.32 (m, 3H), 7.28-7.07 (m, 9H), 7.01 (d, J=7.2 Hz, 1H), 6.82 (d, J=2.0 Hz, 1H), 6.66 (dd, J=8.8, 2.0 Hz, 1H), 4.75 (s, 2H), 4.04 (s, 2H), 3.06-3.00 (m, 2H), 2.84-2.78 (m, 2H), 2.44-2.38 (m, 3H), 2.09 (m, 1H), 1.24-1.18 (m, 2H), 1.11-1.08 (m, 2H). MS (ESI) m/z: 662 [M+1]$^+$.

Step 2: 3-(3-(2-Chloro-4-((5-cyclopropyl-3-(2,6-dichlorophenyl)isoxazol-4-yl)methoxy)phenyl)-3-hydroxycyclobutyl)benzene-1-sulfonyl chloride (5b)

To a solution of compound 5a (34 mg, 0.05 mmol) in CH$_3$CN/HOAc/H$_2$O (1 mL/37 μL/25 μL) was added 2,4-dichloro-5,5-dimethylhydantion (20 mg, 0.1 mmol). The mixture was stirred at 0-5° C. for 2 h. The reaction was diluted with water and extracted with CH$_2$Cl$_2$. The combined organic layers were washed with a 5% NaHCO$_3$ solution, brine and dried over Na$_2$SO$_4$. Concentration to dryness afforded the crude product 5b (30 mg) as a colorless oil, which was used directly in the next step.

Step 3: 3-(3-(2-Chloro-4-((5-cyclopropyl-3-(2,6-dichlorophenvnisoxazol-4-yl)methoxy)phenyl)-3-hydroxycyclobutyl)benzenesulfonamide (5)

To the solution of compound 5b (30 mg) in CH$_3$CN (2 mL) was added NH$_4$OH (0.3 mL). The mixture was stirred at rt for 1 h. Concentration to dryness and purification by prep. RP-HPLC gave the title compound 5 (3.5 mg, 10% for two steps) as a white solid. $^1$H NMR (400 MHz, CDCl$_3$) δ: 7.85 (s, 1H), 7.77 (d, J=7.6 Hz, 1H), 7.54-7.41 (m, 5H), 7.35 (d, J=8.4 Hz, 1H), 6.90 (s, 1H), 6.75 (d, J=8.4 Hz, 1H), 4.83 (s, 2H), 4.77 (s, broad, 2H), 3.20 (t, J=10.4 Hz, 2H), 3.04 (m, 1H), 2.58 (t, J=10.6 Hz, 2H), 2.17 (m, 1H), 1.31-1.30 (m, 2H), 1.20-1.16 (m, 2H). MS (ESI) m/z: 617 [M−1]$^-$.

Example 6: 1-(2-Chloro-4-((5-cyclopropyl-3-(2,6-dichlorophenyl)isoxazol-4-yl)methoxy)phenyl)-3-(3-(methylsulfonyl)phenyl)cyclobutanol (6)

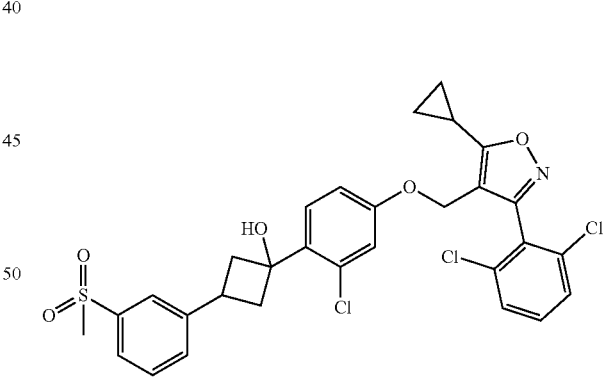

To the solution of compound 2b (200 mg, 0.32 mmol) in DMSO, sodium methanesulfinate (50 mg, 0.46 mmol), CuI (20 mg, 0.1 mmol), L-proline (37 mg, 0.32 mmol) and diisopropylethylamine (DIEA) (41 mg, 0.32 mmol) was added. The mixture was stirred at 95° C. overnight and then diluted with water and extracted with EA. The combined organic layers were washed with water and dried over Na$_2$SO$_4$. Concentration to dryness under reduced pressure and purification by prep. RP-HPLC gave the title compound 6 as a white solid (35 mg, 21%, single isomer by $^1$H NMR and LC-MS). $^1$H NMR (400 MHz, CDCl$_3$) δ: 7.84 (s, 1H), 7.79 (d, J=7.6 Hz, 1H), 7.60 (d, J=7.6 Hz, 1H), 7.53 (t, J=7.6

Hz, 1H), 7.44-7.41 (m, 3H), 7.34 (t, J=7.2 Hz, 1H), 6.90 (d, J=2.8 Hz, 1H), 6.75 (dd, J=8.4, 2.0 Hz, 1H), 4.83 (s, 2H), 3.24-3.19 (m, 2H), 3.08-3.04 (m, 4H), 2.62-2.56 (m, 2H), 2.17 (m, 1H), 1.31-1.29 (m, 2H), 1.20-1.16 (m, 2H). MS (ESI+) m/z: 618 (620) [M+1]$^+$, 600 (602) [M−H$_2$O+1]$^+$.

Example 7: Methyl 5-((1s,3s)-3-(2-chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylate (7)

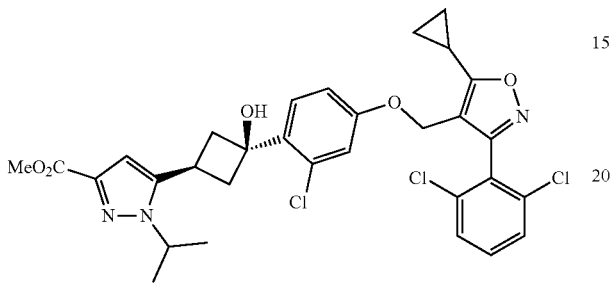

Step 1: Methyl 1-isopropyl-5-vinyl-1H-pyrazole-3-carboxylate (7a)

A suspension of methyltriphenylphosphonium bromide (2.69 g, 7.52 mmol) in dry THF (40 mL) was cooled to −78° C. and n-butyllithium (1.6 M solution in hexane, 3.7 mL, 5.91 mmol) was added dropwise. The yellow-orange suspension was stirred at −78° C. for 50 min and then a solution of methyl 5-formyl-1-isopropyl-1H-pyrazole-3-carboxylate (prepared as described in WO 2011/020615, 1.05 g, 5.37 mmol) in dry THF (10 mL) was added dropwise. The mixture was stirred at −78° C. for 1.75 h, the cooling bath was removed and the mixture (off-white suspension) was stirred at rt for 1 h. The mixture was then partitioned between diluted aq. NaHCO$_3$ solution (150 mL) and EA (150 mL). The aq. layer was extracted twice with EA (50 mL each) and the combined organic layer was washed twice with water (50 mL each) and concentrated without drying to give 2.74 g of a yellow oil which slowly crystallized. The crude product was purified by CC (preadsorption with CH$_2$Cl$_2$, hexane/EA 4:1) to give alkene 7a (590 mg, 57%) as a colorless oil. $^1$H NMR (DMSO-d$_6$) δ: 7.02 (s, 1H), 6.87 (dd, J=17.3, 11.2 Hz, 1H), 5.94 (dd, J=17.3, 1.3 Hz, 1H), 5.45 (dd, J=11.2, 1.3 Hz, 1H), 4.80 (sept, J=6.6 Hz, 1H), 3.79 (s, 3H), 1.38 (d, J=6.6 Hz, 6H). C$_{10}$H$_{14}$N$_2$O$_2$ (194.23). LC-MS (ESI): 195 [M+H]$^+$.

Step 2: Methyl 1-isopropyl-5-(3-oxocyclobutyl)-1H-pyrazole-3-carboxylate (7b)

The reaction was performed in two dry sealed tubes (two batches of equal quantity). The batches were combined for workup and purification. Single batch procedure: To a solution of N,N-dimethylacetamide (0.22 mL, 2.34 mmol) in 1,2-dichloroethane (12 mL) under nitrogen at −15 to −20° C. was added dropwise trifluoromethanesulfonic anhydride (0.43 mL, 2.57 mmol), forming an opaque suspension. The mixture was stirred at −15° C. for 10 min, and a solution of alkene 7a (151 mg, 0.78 mmol) and sym.-collidine (0.42 mL, 3.12 mmol) in 1,2-dichloroethane (3 mL) was added dropwise (yellow solution formed). Upon completion of the addition the cooling was bath removed, the mixture was allowed to warm to rt (orange turbid solution) and the tube was sealed. The mixture was then stirred at 90° C. for 15 h (brown mixtures). Water (5 mL) was added at rt and the mixtures were stirred at 100° C. for 2 h (turbid two-phase solutions). After cooling to rt, the mixtures were combined and partitioned between diluted aq. NaHCO$_3$ solution and CH$_2$Cl$_2$ and the aq. layer was extracted three times with CH$_2$Cl$_2$ (30 mL each). The combined organic layer was dried (Na$_2$SO$_4$), filtered and concentrated to give a brown oil (2.2 g). Purification by CC (6×13 cm, preadsorption with CH$_2$Cl$_2$, toluene/EA 3:1) gave cyclobutanone 7b (115.5 mg, 31%) as a yellow oil. $^1$H NMR (DMSO-d$_6$) δ: 6.81 (s, 1H), 4.58 (sept, J=6.5 Hz, 1H), 3.78 (s, 3H), 3.85-3.73 (m, 1H), 3.59-3.45 (m, 2H), 3.37-3.24 (m, 2H, partially overlapped by water signal), 1.39 (d, J=6.6 Hz, 6H). C$_{12}$H$_{16}$N$_2$O$_3$ (236.27). LC-MS (ESI): 237 [M+H]$^+$.

Step 3: Methyl 5-((1s,3s)-3-(2-chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylate (7)

A solution of bromide 1a (368 mg, 0.78 mmol) in dry THF (6 mL) was cooled to −78° C. and a 1.6M n-butyllithium solution in hexanes (0.48 mL, 0.76 mmol) was added dropwise. The mixture was stirred at −78° C. for 20 min and a solution of cyclobutanone 7b (164 mg, 0.69 mmol) in dry THF (4 mL) was added dropwise. The mixture was stirred at −78° C. for 2.5 h and saturated aq. NH$_4$Cl solution (1 mL) was added dropwise at this temperature. The cooling bath was removed and the mixture was allowed to warm to rt and stirred at rt for 0.5 h. The mixture was then added to diluted aq. NH$_4$Cl solution and extracted three times with EA. The combined organic layer was dried (Na$_2$SO$_4$), filtered and concentrated to give 516 mg of an almost colorless oil. Purification by CC (4.5×23 cm, preadsorption with CH$_2$Cl$_2$, eluent hexane/acetone=2:1) afforded recovered cyclobutanone 7b (31.3 mg, 19%, slightly yellow oil) and impure product (333 mg). Repurification by CC (4×22 cm, hexane/EA=1:1) or prep-TLC gave pure product 7 (210 mg, 48%) as white foam. $^1$H NMR (DMSO-d$_6$) δ: 7.65 (d, J=2.1 Hz, 1H), 7.62 (s, 1H), 7.59-7.48 (m, 2H), 6.92 (d, J=2.4 Hz, 1H), 6.76 (dd, J=8.6, 2.6 Hz, 1H), 6.66 (s, 1H), 5.49 (s, 1H), 4.92 (s, 2H), 4.42 (quint-like m, J=6.5 Hz, 1H), 3.78 (s, 3H), 3.24-3.11 (m, 2H, partially overlapped by water signal), 3.04-2.90 (m, 1H), 2.54-2.33 (m, 3H, partially overlapped by DMSO signal), 1.32 (d, J=6.5 Hz, 6H), 1.26-1.08 (m, 4H). C$_{31}$H$_{30}$Cl$_3$N$_3$O$_5$ (630.95). LC-MS (ESI): 630, 632 [M+H]$^+$.

Example 8: 5-((1s,3s)-3-(2-Chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylic acid (8)

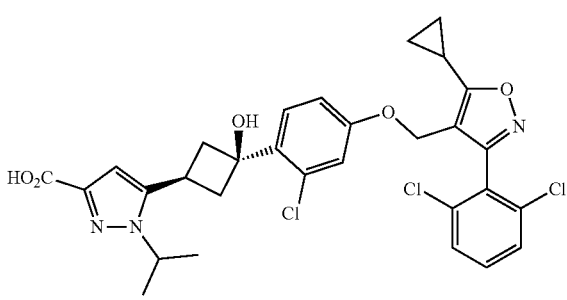 [SMILES: CC(C)n1nc(C(=O)O)cc1[C@H]1C[C@](O)(c2ccc(OCc3c(-c4c(Cl)cccc4Cl)noc3C3CC3)cc2Cl)C1]

Ester 7 (98.3 mg, 0.156 mmol) was dissolved in a mixture of THF (7.5 mL), MeOH (2.5 mL) and water (2.5 mL) and LiOH.H$_2$O (65 mg, 1.56 mmol) was added at rt. The mixture was stirred at rt for 18 h. The mixture was partitioned between diluted aq. NH$_4$Cl solution and EA and the organic layer was washed once with water. The combined aq. layer was extracted twice with EA. The combined organic layer was dried (Na$_2$SO$_4$), filtered and concentrated to give 103 mg of an almost white solid. The product was purified by CC (3×3.5 cm, EA/EtOH=10:1 to 1:4) to afford 8 (94.8 mg, 99%) as a white solid. $^1$H NMR (DMSO-d$_6$) δ: 7.66-7.60 (m, 1H), 7.62 (s, 1H), 7.59-7.49 (m, 2H), 6.91 (d, J=2.5 Hz, 1H), 6.76 (dd, J=8.6, 2.4 Hz, 1H), 6.38 (s, 1H), 5.51 (s, 1H, exchangeable with D$_2$O), 4.92 (s, 2H), 4.31 (quint-like m, J=6.5 Hz, 1H), 3.25-3.08 (m, 2H, partially overlapped by water signal), 2.93-2.77 (m, 1H), 2.57-2.43 (m, 1H, hidden by DMSO signal), 2.43-2.29 (m, 2H, partially overlapped by DMSO signal), 1.29 (d, J=6.5 Hz, 6H), 1.26-1.08 (m, 4H). The CO$_2$H signal does not appear in the spectrum. C$_{30}$H$_{28}$Cl$_3$N$_3$O$_6$ (616.92). LC-MS (ESI): 616, 618 [M+H]$^+$.

Alternative Route to Example 8

Step 1: 1-(3-Methylenecyclobutyl)ethanone (8a)

Methylene cyclobutane carbonitrile (5.0 g, 53.7 mmol) was dissolved in dry diethylether (25 mL), cooled in an ice bath and MeMgBr (26.8 mL, 80.5 mmol, 3 M in ether) was added dropwise. The mixture was left stirring overnight at rt, cooled to 0° C., quenched carefully with 15% NaHSO$_4$ aq. sol. (100 mL). The mixture was stirred at rt for 30 min. and the layers were separated. The aq. phase was extracted with pentane (50 mL) and diethylether (50 mL). The combined organic layers were washed with brine and dried over Na$_2$SO$_4$. The solvents were removed under vacuum at rt and the crude product was obtained as a yellowish liquid.

Step 2: Ethyl 4-(3-methylenecyclobutyl)-2,4-dioxobutanoate (8b)

Sodium (1.15 g, 49.9 mmol) was dissolved in dry EtOH (30 mL, denaturated with 5% diethylether). Compound 8a (5.5 g, 49.9 mmol, crude) was dissolved in dry EtOH (45 mL) and the above prepared sodium ethoxide solution was added. This mixture was stirred at rt for 15 min and then diethyl oxalate (6.8 mL, 49.9 mmol) was added dropwise. The reaction mixture was placed in a pre-heated (to 67° C.) oil bath and stirred at this temperature for 4.5 h. The mixture was left at rt overnight. The solvent was removed, EA (100 mL) and 1 M HCl (70 mL) were added and organic phase was separated. The aq. phase was re-extracted with EA (50 mL). The combined organic phases were washed with water, brine and dried over anh. Na$_2$SO$_4$. The solvent was removed under reduced pressure and the residue was purified on silica using hexanes/MTBE 9:1 as eluent giving pure product 8b. Yield: 6.29 g, 56% over two steps. $^1$H-NMR (CDCl$_3$), δ (ppm): 6.36 (s, 1H), 4.85-4.80 (m, 2H), 4.34 (q, J=8.0 Hz, 2H), 3.35-3.25 (m, 1H), 3.05-2.85 (m, 4H), 1.36 (t, J=8.0 Hz, 3H).

Step 3: Ethyl 1-isopropyl-5-(3-methylenecyclobutyl)-1H-pyrazole-3-carboxylate (8c)

Compound 8b (6.29 g, 29.9 mmol) was dissolved in dry EtOH (65 mL, denaturated with 5% of MeOH) and isopropyl hydrazine hydrochloride (3.97 g, 35.9 mmol) was added. The reaction mixture was stirred for 3 h at rt. The solvent was removed and to the oily residue were added EA (100 mL), water (50 mL) and sat. NaHCO$_3$ (50 mL) sequentially. The layers were separated and the aq. phase was re-extracted with EA (50 mL). The combined organic phases were washed with brine (70 mL) and dried over anh. Na$_2$SO$_4$. The solvent was removed under vacuum and the residue was dried under reduced pressure. Yield: 7.23 g (contains 3.4% of EtOAc by NMR, recalculated pure yield: 6.98 g, 94%). Crude product 8c is 98% pure by HPLC and NMR. $^1$H-NMR (CDCl$_3$), δ (ppm): 6.62 (s, 1H), 4.88-4.82 (m, 2H), 4.42-4.32 (m, 3H), 3.56-3.45 (m, 1H), 3.17-3.07 (m, 2H), 2.88-2.79 (m, 2H), 1.49 (d, J=8.0 Hz, 6H), 1.37 (t, J=8.0 Hz, 3H).

Step 4: Ethyl 1-isopropyl-5-(3-oxocyclobutyl)-1H-pyrazole-3-carboxylate (8d)

Compound 8c (6.45 g, 26.0 mmol) was dissolved in a mixture of MeCN (77 mL) and water (13 mL) and cooled in an ice-bath. To this solution RuCl$_3$×H2O (0.19 g, 0.86 mmol) was added, followed by portion-wise addition of NaIO$_4$ (19.35 g, 90.9 mmol). An exotherm was observed during this addition. The obtained thick slurry was stirred at rt for 45 min. The reaction mixture was diluted with Na$_2$S$_2$O$_3$ aq. sol. (10%, 260 mL), water (50 mL) and DCM (100 mL). The phases were separated and the aq. phase was extracted with DCM (2×70 mL). The combined organic phases were washed with Na$_2$S$_2$O$_3$ aq. sol. (10%, 50 mL), water (100 mL), brine (100 mL) and dried over anh. Na$_2$SO$_4$. The crude product (6.5 g) was purified on silica, eluting with hexanes/MTBE to give pure product as an oil that solidified upon storage at –20° C. Yield: 5.8 g (78% over two steps). $^1$H-NMR (DMSO-d$_6$), δ (ppm): 6.78 (s, 1H), 4.57 (h, J=8.0 Hz, 1H), 4.26 (q, J=8.0 Hz, 2H), 3.85-3.75 (m, 1H), 3.58-3.45 (m, 2H), 3.35-3.25 (m, 2H), 1.39 (d, J=8.0 Hz, 6H), 1.28 (t, J=8.0 Hz, 3H).

Step 5: 4-((4-Bromo-3-chlorophenoxy)methyl)-5-cyclopropyl-3-(2,6-dichlorophenyl)isoxazole (8e)

3-Chloro-4-bromophenol (3.8 g, 18.3 mmol) was mixed with (5-cyclopropyl-3-(2,6-dichlorophenyl)isoxazol-4-yl)methanol (3.47 g, 12.2 mmol) and triphenylphosphine (6.41 g, 24.4 mmol) in toluene (150 mL). The mixture was cooled in an ice-bath and DIAD (4.8 mL, 24.4 mmol) as a solution in toluene (10 mL) was added drop-wise. The reaction was stirred at rt for 21 h and the solvents were removed on a rotavap leaving a yellow oily residue. This was dissolved in DCM (200 mL), silica (~20 g) was added and the mixture was evaporated to dryness. This material was loaded on the top of a silica column and purified eluting with hexanes/MTBE 9:1. The product containing fractions were pooled and the solvent removed under reduced pressure, leaving pure product 8e as a colourless oil that crystallized upon drying under vacuum overnight. Yield: 5.07 g (88%). $^1$H-NMR (CDCl$_3$), δ (ppm): 7.45-7.30 (m, 4H), 6.90 (s, 1H), 6.60-6.55 (m, 1H), 2.15-2.07 (m, 1H), 1.32-1.25 (m, 2H), 1.20-1.11 (m, 2H).

Step 6: Ethyl 5-((1s,3s)-3-(2-chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylate (8f)

LiCl (0.684 g, 16.15 mmol) was dissolved in THF (20 mL) at rt and iPrMgCl (2.0 M in THF, 8.1 mL, 16.15 mmol) was added. The mixture was stirred for 10 min at rt, cooled in an ice-bath and a solution of compound 8e (2.55 g, 5.38 mmol) in THF (20 mL) was added over 5 min. The cooling bath was removed and the mixture was stirred at rt for 4 h. The mixture was cooled to −10° C. and a solution of compound 8d (1.48 g, 5.92 mmol) in THF (16 mL) was added rapidly. The mixture was stirred at rt for 90 min. and then 0.5 M NaHSO$_4$ aq. (35 mL) and EA (50 mL) were added. The resulting mixture was stirred for 10 min., the layers were separated and the aq. layer was extracted with EA (30 mL). The combined organic phases were washed with NaHCO$_3$ aq. (50 mL), brine (50 mL) and dried over anh. Na$_2$SO$_4$. The crude product (3.79 g) was obtained after removal of the solvent as a white foam. 3.6 g of this crude was purified on silica column, eluting with hexanes/EA 3:2 to give pure product 8f as a solid foam. Yield: 1.62 g (49%). $^1$H-NMR (DMSO-d$_6$), δ (ppm): 7.65-7.47 (m, 4H), 6.93-6.91 (m, 1H), 6.79-6.72 (m, 1H), 6.65 (s, 1H), 5.48 (s, 1H), 4.92 (s, 2H), 4.42 (h, J=8.0 Hz, 1H), 4.26 (q, J=8.0 Hz, 2H), 3.32 (s, 2H), 3.22-3.14 (m, 2H), 3.05-2.90 (m, 1H), 2.45-2.35 (m, 2H), 1.35-1.10 (m, 14H).

Step 7: 5-((1s,3s)-3-(2-Chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylic acid (8)

Compound 8f (1.60 g, 2.48 mmol) was dissolved in THF (100 mL), then MeOH (50 mL), water (50 mL) and LiOH× H2O (1.04 g, 24.8 mmol) were added sequentially. The mixture was stirred for 4.5 h at rt and then concentrated under reduced pressure to remove MeOH and THF. The remaining aq. solution was acidified by addition of 1 M HCl aq. (24 mL) to reach pH of 4.05 (pH electrode control). Already at approx. pH 7 a precipitate started to form. The formed solid was filtered off, washed on the filter with water and dried under vacuum at rt to give product 8 as a white powder. Yield: 1.40 g (92%). $^1$H-NMR (CDCl$_3$), δ (ppm): 7.44-7.32 (m, 4H), 6.91 (d, J=4.0 Hz, 1H), 6.78 (s, 1H), 6.75 (dd, J=4.0 Hz, J=8.0 Hz, 1H), 4.83 (s, 2H), 4.35-4.20 (m, 1H), 3.25-3.14 (m, 2H), 3.04-2.90 (m, 1H), 2.62-2.54 (m, 2H), 2.21-2.11 (m, 1H), 1.46 (d, J=8.0 Hz, 6H), 1.34-1.28 (m, 2H), 1.20-1.14 (m, 2H). $^{13}$C-NMR (CDCl$_3$), δ (ppm): 172.7, 164.8, 159.2, 158.4, 147.2, 141.3, 135.8, 134.1, 132.8, 131.3, 128.1, 127.6, 127.3, 117.7, 113.3, 110.0, 106.3, 73.1, 59.8, 51.1, 41.7, 22.6, 22.0, 8.5, 7.8. MS (ESL) m/z: 616.4 [M+1]$^+$.

Example 8A 5-((1r,3r)-3-(2-Chloro-4-((5-cyclopropyl-3-(2,6-dichlorophenyl)isoxazol-4-yl)methoxy)phenyl)-3-hydroxycyclobutyl)-1-isopropyl-1H-pyrazole-3-carboxylate (8A)

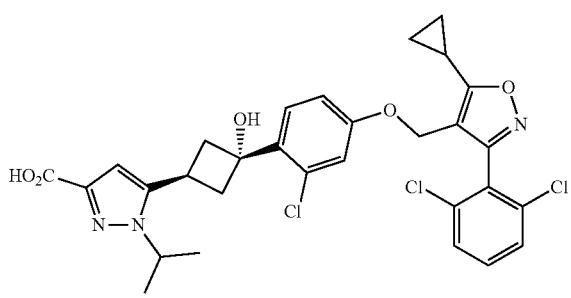 [SMILES: CC(C)n1nc(C(=O)O)cc1[C@H]1C[C@@](O)(c2ccc(OCc3c(-c4c(Cl)cccc4Cl)noc3C3CC3)cc2Cl)C1]

Example 8A can be prepared by subjecting the crude product 8f to the ester hydrolysis as described for 8 and isolation from the crude product 8 as a minor isomer by preparative RP-HPLC. $^1$H-NMR (CDCl$_3$), δ (ppm): 7.42-7.30 (m, 2H), 7.11 (d, J=8.0 Hz, 1H), 6.75-6.65 (m, 1H), 6.57 (s, 1H), 4.79 (s, 2H), 4.50-4.41 (m, 1H), 3.96-3.85 (m, 1H), 2.98-2.90 (m, 2H), 2.67-2.57 (m, 2H), 2.20-2.09 (m, 1H), 1.51 (d, J=8.0 Hz, 6H), 1.32-1.14 (m, 4H). $^{13}$C-NMR (CDCl$_3$), δ (ppm): 172.6, 166.2, 159.2, 158.4, 147.4, 141.2, 135.7, 134.6, 132.8, 131.3, 128.1, 127.7, 127.5, 116.8, 113.5, 110.0, 105.8, 75.1, 59.8, 51.2, 41.8, 25.4, 22.6, 8.5, 7.8. MS (ESL) m/z: 616.3 [M+1]$^+$.

Figure 1B:
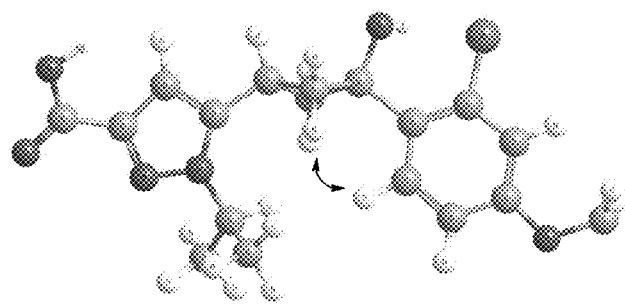
FIG. 1B: NOEs detected for example 8A with 1,3-cis transannular configuration of the aromatic moieties are shown with double arrows.

The transannular configuration of the major isomer (compound 8) and the minor isomer (compound 8A) was confirmed by NOE experiments. The detected indicative NOEs between protons are shown in FIG. 1A and FIG. 1B, respectively.

Example 9: Methyl 6-(3-(2-chloro-4-((5-cyclopropyl-3-(2,6-dichlorophenyl)isoxazol-4-yl)methoxy)phenyl)-3-hydroxycyclobutyl)-1-methyl-1H-indazole-3-carboxylate (9)

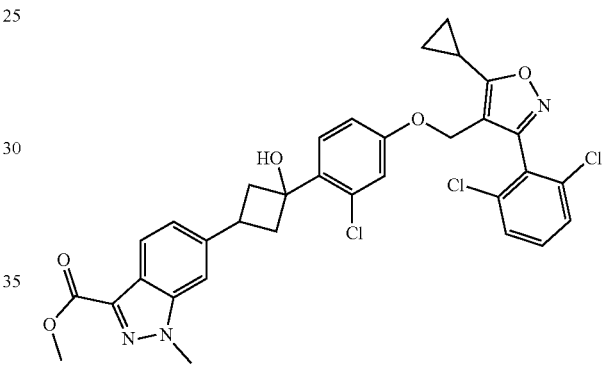

Step 1: Methyl 1-methyl-6-vinyl-1H-indazole-3-carboxylate (9a)

To the solution of methyl 6-bromo-1-methyl-1H-indazole-3-carboxylate (60 mg, 0.22 mmol) in DMF (10 mL), tributyl(vinyl)tin (99 μL, 0.34 mmol), Pd(Ph$_3$)$_4$ (11 mg, 9 μmol) was added. After the addition was completed, the mixture was stirred at 90° C. for 4 h under Ar. Then the solvent was removed under reduced pressure. Purification by CC afforded compound 9a (52 mg, 88%).

Step 2: Methyl 1-methyl-6-(3-oxocyclobutyl)-1H-indazole-3-carboxylate (9b)

Following the procedure as described in Example 7/Step 2, compound 9b was obtained from 9a in 57% yield. $^1$H NMR (400 MHz, CDCl$_3$) δ: 8.14 (d, J=8.4 Hz, 1H), 7.31 (s, 1H), 7.23 (d, J=8.8 Hz, 1H), 4.13 (s, 3H), 3.99 (s, 3H), 3.87-3.79 (m, 1H), 3.58-3.51 (m, 2H), 3.33-3.26 (m, 2H). m/z: 259 [M+1]$^+$.

Step 3: Methyl 6-(3-(2-chloro-4-((5-cyclopropyl-3-(2,6-dichlorophenyl)isoxazol-4-yl)methoxy)phenyl)-3-hydroxycyclobutyl)-1-methyl-1H-indazole-3-carboxylate (9)

Following the procedure as described in Example 7/Step 3, compound 9 was obtained from 9b in 40% yield.

Example 10: 6-(3-(2-Chloro-4-((5-cyclopropyl-3-(2,6-dichlorophenyl)isoxazol-4-yl)methoxy)phenyl)-3-hydroxycyclobutyl)-1-methyl-1H-indazole-3-carboxylic acid (10)

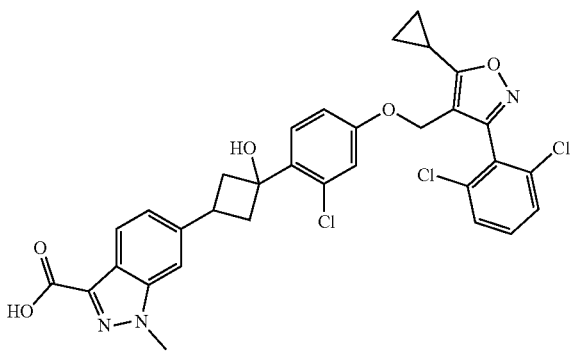 [SMILES: Cn1nc(C(=O)O)c2ccc(C3CC(O)(c4ccc(OCc5c(-c6c(Cl)cccc6Cl)noc5C5CC5)cc4Cl)C3)cc21]

Following the procedure as described in Example 8, compound 10 was obtained from compound 9 in 45% yield as a white solid. ¹H NMR (400 MHz, CDCl₃) δ: 8.14 (d, J=8.0 Hz, 1H), 7.48 (d, J=8.8 Hz, 1H), 7.43-7.32 (m, 4H), 7.29 (m, 1H), 6.92 (d, J=2.4 Hz, 1H), 6.76 (dd, J=7.2 Hz, 2.4 Hz, 1H), 4.84 (s, 2H), 4.18 (s, 3H), 3.45-3.40 (m, 1H), 3.28-3.23 (m, 2H), 3.19-3.10 (m, 1H), 2.68-2.63 (m, 2H), 2.21-2.14 (m, 1H), 1.33-1.29 (m, 2H), 1.20-1.15 (m, 2H). m/z: 638 [M+1]⁺.

Preparative Example 11

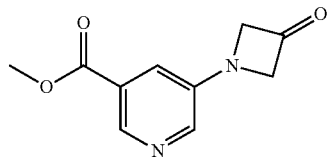

Step 1: Methyl 5-(3-hydroxyazetidin-1-yl)nicotinate (11a)

A mixture of methyl 5-bromonicotinate (2.00 g, 9.26 mmol), azetidin-3-ol (1.01 g, 9.26 mmol), Cs₂CO₃ (9.06 g, 27.8 mmol), BINAP (1.15 g, 1.85 mmol) and Pd(OAc)₂ (0.44 g, 1.85 mmol) in dry dioxane (115 mL) was heated overnight at 85° C. under N₂ atmosphere. The resulting mixture was filtrated, concentrated under reduced pressure and purified by prep-HPLC to give compound 11a (250 mg, 13%) of as a yellow solid.

Step 2: Methyl 5-(3-oxoazetidin-1-yl)nicotinate (11)

To a solution of compound 11a (250 mg, 1.20 mmol) in dry DCM (15 mL) was added Dess-Martin periodinane (1.014 g, 2.40 mmol) at 0° C. under N₂ atmosphere and the solution was stirred at rt for 2 h. The resulting solution was quenched with saturated sodium bicarbonate solution and diluted with EA. The organic portion was washed with brine, dried over Na₂SO₄, filtered, concentrated under reduced pressure and purified by CC (DCM/MeOH=150:1) to give compound 11 (140 mg, 57%) of as a yellow solid.

Preparative Example 12

Using a similar procedure as that described in Preparative Example 11 the following compound has been prepared:

Example 13/1 to 13/9

The following table lists further examples prepared according the above mentioned preparative examples and examples. All listed compounds were prepared as single isomers.

| # | Structure | Analytical data |
|---|---|---|
| 13/1 | 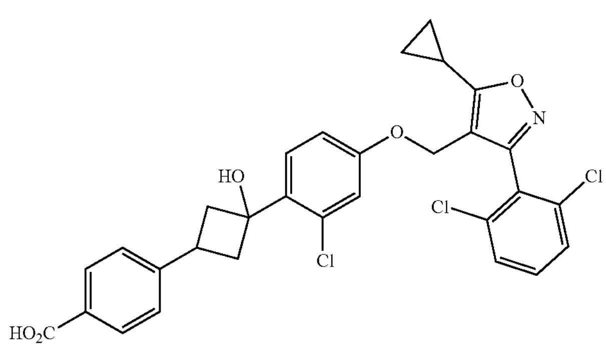 [SMILES: O=C(O)c1ccc(C2CC(O)(c3ccc(OCc4c(-c5c(Cl)cccc5Cl)noc4C4CC4)cc3Cl)C2)cc1] | ¹H NMR (400 MHz, DMSO-d₆) δ: 1.15-1.25 (m, 4H), 2.35-2.50 (m, 5H, partially under solvent signal), 2.80-2.91 (m, 1H), 3.11-3.20 (m, 2H), 4.93 (s, 2H), 6.72-6.81 (m, 1H), 6, 93 (s, 1H), 7.40-7.51 (m, 2H), 7.52-7.60 (m, 2H), 7.62-7.66 (m, 2H), 7.85-7.90 (m, 2H). MS Calcd.: 583; MS Found: 584 [M + H]⁺. |

-continued

| # | Structure | Analytical data |
|---|---|---|
| 13/2 | 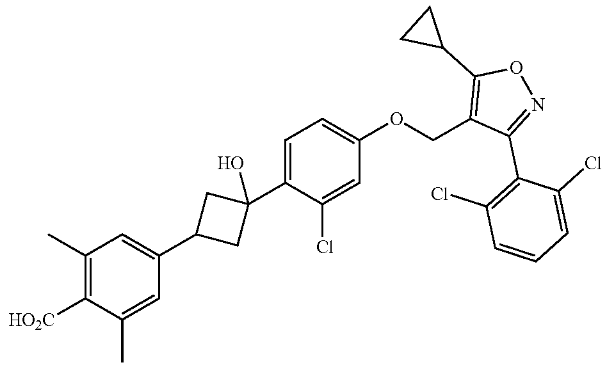 [SMILES: Cc1cc(C2CC(O)(c3ccc(OCc4c(-c5c(Cl)cccc5Cl)noc4C4CC4)cc3Cl)C2)cc(C)c1C(=O)O] | $^1$H NMR (400 MHz, CD$_3$OD) δ: 1.05-1.12 (m, 4H), 2.18-2.34 (m, 9H), 2.62-2.71 (m, 1H), 2.99-3.09 (m, 2H), 4.78 (s, 2H), 6.60-6.64 (m, 1H), 6.72-6.78 (m, 1H), 6.85 (s, 2H), 7.30-7.42 (m, 4H). MS Calcd.: 611; MS Found: 612 [M + H]$^+$. |
| 13/3 | 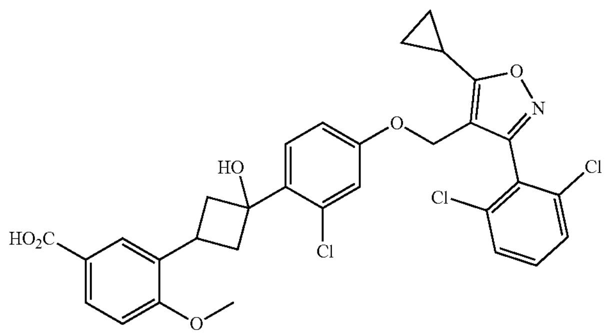 [SMILES: COc1ccc(C(=O)O)cc1C1CC(O)(c2ccc(OCc3c(-c4c(Cl)cccc4Cl)noc3C3CC3)cc2Cl)C1] | $^1$H NMR (400 MHz, CD$_3$OD) δ: 1.10-1.23 (m, 4H), 2.36-2.49 (m, 3H), 3.00-3.12 (m, 1H), 3.15-3.25 (m, 2H), 3.87 (s, 3H), 4.95 (s, 2H), 6.72-6.80 (m, 1H), 6.89 (s, 1H), 6.90-7.00 (m, 1H), 7.42-7.60 (m, 4H), 7.89-7.93 (m, 1H), 7.98 (s, 1H). MS Calcd.: 613; MS Found: 612 [M − H]$^-$. |
| 13/4 | 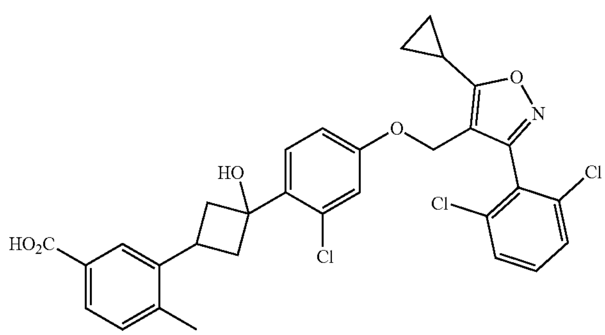 [SMILES: Cc1ccc(C(=O)O)cc1C1CC(O)(c2ccc(OCc3c(-c4c(Cl)cccc4Cl)noc3C3CC3)cc2Cl)C1] | $^1$H NMR (400 MHz, CD$_3$OD) δ: 1.20-1.30 (m, 4H), 2.27 (s, 3H), 2.30-2.55 (m, 3H), 2.98-3.10 (m, 1H), 3.25-3.40 (m, 2H, partially under solvent signal), 4.95 (s, 2H), 6.76-6.84 (m, 1H), 6.91 (s, 1H), 7.20-7.25 (m, 1H), 7.43-7.63 (m, 4H), 7.75-7.82 (m, 1H), 8.03 (s, 1H). MS Calcd.: 597; MS Found: 596 [M − H]$^-$. |
| 13/5 | 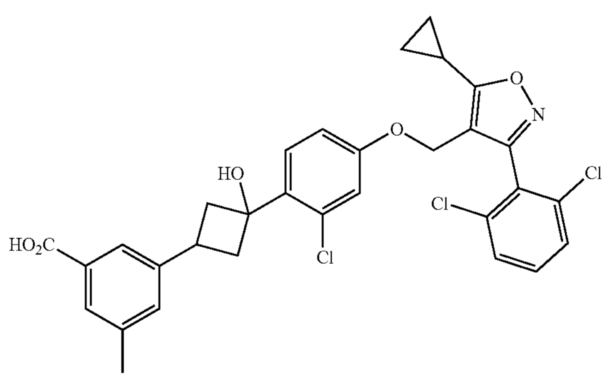 [SMILES: Cc1cc(C(=O)O)cc(C2CC(O)(c3ccc(OCc4c(-c5c(Cl)cccc5Cl)noc4C4CC4)cc3Cl)C2)c1] | $^1$H NMR (400 MHz, CD$_3$OD) δ: 1.20-1.25 (m, 4H), 2.33-2.43 (m, 4H), 2.46-2.56 (m, 2H), 2.88-2.97 (m, 1H) 3.22-3.30 (m, 2H), 4.94 (s, 2H), 6.78-6.82 (m, 1H), 6.90 (s, 1H), 7.37 (s, 1H), 7.43-7.60 (m, 4H), 7.69 (s, 1H), 7.78 (s, 1H). MS Calcd.: 597; MS Found: 596 [M − H]$^-$. |

-continued

| # | Structure | Analytical data |
|---|---|---|
| 13/6 | 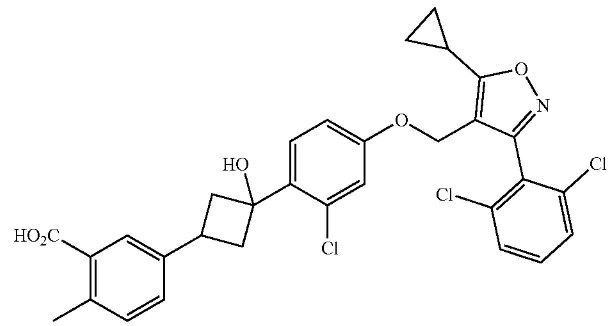 [SMILES: Cc1ccc(C2CC(O)(c3ccc(OCc4c(-c5c(Cl)cccc5Cl)noc4C4CC4)cc3Cl)C2)cc1C(=O)O] | ¹H NMR (400 MHz, CD₃OD) δ: 1.17-1.23 (m, 4H), 2.31-2.40 (m, 4H), 2.42-2.50 (m, 2H), 2.83-2.92 (m, 1H) 3.19-3.26 (m, 2H), 4.92 (s, 2H), 6.74-6.80 (m, 1H), 6.88 (s, 1H), 7.19-7.22 (m, 1H), 7.43-7.57 (m, 4H), 7.83 (s, 1H). MS Calcd.: 597; MS Found: 598 [M + H]⁺. |
| 13/7 | 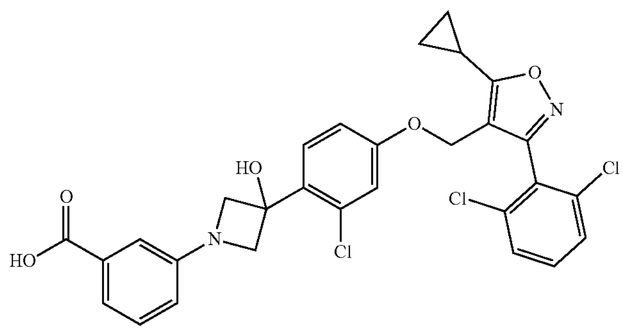 [SMILES: O=C(O)c1cccc(N2CC(O)(c3ccc(OCc4c(-c5c(Cl)cccc5Cl)noc4C4CC4)cc3Cl)C2)c1] | ¹H NMR (400 MHz, CD₃OD) δ: 1.09-1.11 (m, 4H), 2.19-2.26 (m, 1H), 4.08-4.10 (m, 2H), 4.19-4.21 (m, 2H), 4.80 (s, 2H), 6.64-6.67 (m, 2H), 6.75 (s, 1H), 7.16-7.21 (m, 2H), 7.28-7.39 (m, 6H); MS Calcd.: 584; MS Found: 585 (M + 1). |
| 13/8 | 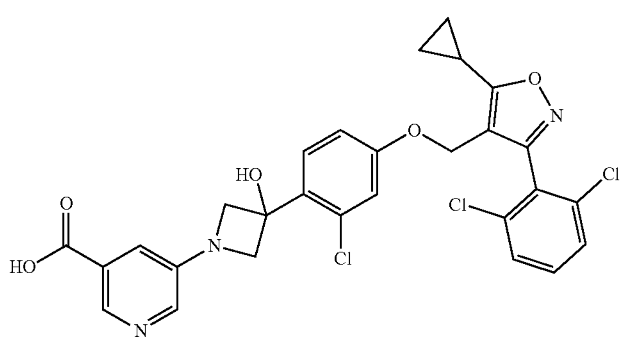 [SMILES: O=C(O)c1cncc(N2CC(O)(c3ccc(OCc4c(-c5c(Cl)cccc5Cl)noc4C4CC4)cc3Cl)C2)c1] | ¹H NMR (300 MHz, CDCl₃) δ: 1.11 (m, 2H), 1.24 (m, 2H), 2.11 (m, 1H), 4.33 (m, 2H), 4.46 (m, 2H), 4.78 (s, 2H), 6.67 (dd, J = 1.2 Hz, 8.4 Hz, 1H), 6.77 (d, J = 2.4 Hz, 1H), 6.67 (d, J = 8.4 Hz, 1H), 7.28-7.35 (m, 3H), 7.55 (d, J = 1.2 Hz, 1H), 7.94 (s, 1H), 8.56 (d, J = 3.6 Hz, 1H); MS Calcd.: 585; MS Found: 586 (M + 1). |
| 13/9 | 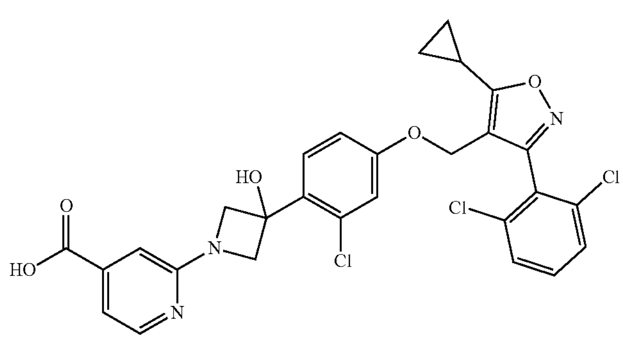 [SMILES: O=C(O)c1ccnc(N2CC(O)(c3ccc(OCc4c(-c5c(Cl)cccc5Cl)noc4C4CC4)cc3Cl)C2)c1] | ¹H NMR (300 MHz, DMSO-d₆) δ: 1.13-1.23 (m, 4H), 2.50 (m, 1H), 4.23 (d, J = 8.4 Hz, 2H), 4.51 (d, J = 9.3 Hz, 2H), 4.96 (s, 2H), 6.24 (s, 1H), 6.80 (d, J = 7.5 Hz, 1H), 6.88 (s, 1H), 6.97 (s, 1H), 7.07 (s, 1H), 7.44 (d, J = 8.4 Hz, 1H), 7.58-7.66 (m, 3H), 8.25 (s, 1H); MS Calcd.: 585; MS Found: 586 (M + 1). |

Example 14/1 and 14/2

Using a similar procedure as described in the Examples 1 to 13 and Schemes above, the following compounds were obtained by using the appropriate building blocks.

Assays
FRET Activity Assay

Determination of a ligand mediated cofactor peptide interaction to quantify ligand binding to the nuclear receptor FXR was performed as follows: Preparation of human FXR

| # | Structure | Analytical data |
|---|---|---|
| 14/1 | 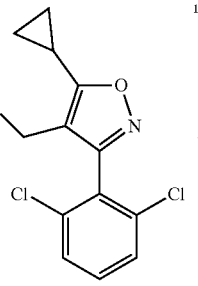 | $^1$H NMR (400 MHz, DMSO-$d_6$): δ 1.13~1.23 (m, 4H), 1.33 (d, J = 6.4 Hz, 6H), 2.37~2.47 (m, 3H), 2.90-2.95 (m, 1H), 3.14-3.19 (t, J = 8.8 Hz, 2H), 3.57 (d, J = 4.0 Hz, 2H), 4.38 (m, 1H), 4.92 (s, 2H), 5.51 (s, 1H), 6.51 (s, 1H), 6.76 (dd, J = 2.4 Hz, J = 8.4 Hz, 1H), 6.91 (d, J = 2.4 Hz, 1H), 7.51-7.58 (m, 2H), 7.62-7.65 (m, 2H), 7.69 (s, 1H); MS Calcd.: 672; MS Found: 673 [M + H]$^+$. |
| 14/2 | 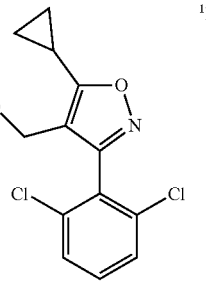 | $^1$H NMR (400 MHz, DMSO-$d_6$): δ 1.13~1.20 (m, 4H), 1.31 (d, J = 6.0 Hz, 6H), 2.36~2.47 (m, 3H), 2.59-2.63 (m, 2H), 2.89-2.93 (m, 1H), 3.17-3.19 (m, 2H), 3.47-3.52 (m, 2H), 4.33-4.39 (m, 1H), 4.92 (s, 2H), 5.51 (s, 1H), 6.50 (s, 1H), 6.76 (dd, J = 2.4 Hz, J = 8.4 Hz, 1H), 6.91 (d, J = 2.4 Hz, 1H), 7.51-7.58 (m, 2H), 7.62-7.65 (m, 2H), 8.18-8.20 (m, 1H); MS Calcd.: 744; MS Found: 721 [M − Na]$^-$. |
| 14/3 | 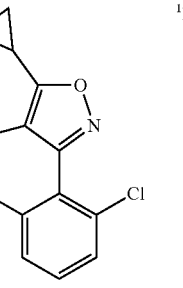 | $^1$H NMR (400 MHz, DMSO-$d_6$): δ 1.10~1.25 (m, 4H), 1.34 (d, J = 6.4 Hz, 6H), 3.03-2.95 (m, 1H), 2.50-2.30 (m, 3H), 3.20-3.10 (m, 2H), 4.50-4.35 (m, 1H), 4.92 (s, 2H), 5.5 (s, 1H), 6.92 (s, 1H), 6.78-6.70 (m, 2H), 7.70-7.49 (m, 4H), 11.44 (s, 1H); MS Calcd.: 694; MS Found: 695 [M + H]$^+$. |

The following compound can be prepared in the same manner by using similar procedures as described above:

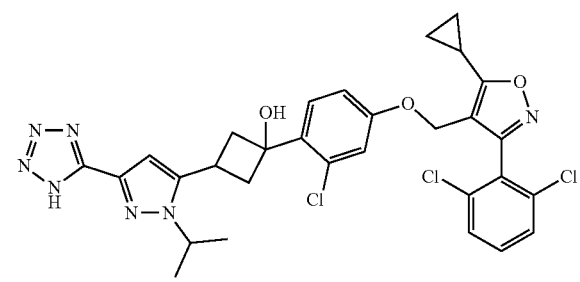 [SMILES: CC(C)n1nc(-c2nnn[nH]2)cc1C1CC(O)(c2ccc(OCc3c(-c4c(Cl)cccc4Cl)noc3C3CC3)cc2Cl)C1]

alpha ligand binding domain: The human FXRalpha LBD was expressed in *E. coli* strain BL21(DE3) as an N-terminally GST tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed *E. coli* strain was diluted 1:20 in LB-Ampicillin medium and grown at 30° C. to an optical density of OD$_{600}$=0.4-0.6. Gene expression was then induced by addition of 0.5 mM IPTG. Cells were incubated an additional 6 h at 30° C., 180 rpm. Cells were collected by centrifugation (7000×g, 7 min, rt). Per liter of original cell culture, cells were resuspended in 10 mL lysis buffer (50 mM Glucose, 50 mM Tris pH 7.9, 1 mM EDTA and 4 mg/mL lysozyme) and left on ice for 30 min. Cells were then subjected to sonication and cell debris removed via centrifugation (22000×g, 30 min, 4° C.). Per 10 mL of supernatant 0.5 mL prewashed Glutathione 4B sepharose slurry (Qiagen) was added and the suspension kept slowly rotating for 1 h at 4° C. Glutathione 4B sepharose beads were pelleted by centrifugation (2000× g, 15 sec, 4° C.) and washed twice in wash buffer (25 mM Tris, 50 mM KCl, 4 mM $MgCl_2$ and 1M NaCl). The pellet was resuspended in 3 mL elution buffer per liter of original culture (elution buffer: 20 mM Tris, 60 mM KCl, 5 mM $MgCl_2$ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM $MgCl_2$ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B—CPSSHSSLTERHKILHRLLQEGSPS-COOH where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 µL in a 384 well plate, in a Tris-based buffer (20 mM Tris-HCl pH 7.5; 60 mM KCl, 5 mM $MgCl_2$; 35 ng/µL BSA), containing 20-60 ng/well recombinantly expressed FXR-LBD fused to GST, 200-600 nM N-terminally biotinylated peptide, representing SRC1 aminoacids 676-700, 200 ng/well Streptavidin-xlAPC conjugate (Prozyme) and 6-10 ng/well Eu W1024-antiGST (Perkin Elmer). DMSO content of the samples was kept at 1%. After generation of the assay mix and diluting the potentially FXR modulating ligands, the assay was equilibrated for 1 h in the dark at rt in FIA-plates black 384 well (Greiner). The LANCE signal was detected by a Perkin Elmer VICTOR2V™ Multilabel Counter. The results were visualized by plotting the ratio between the emitted light at 665 and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal.

To assess the inhibitory potential of the compounds, $EC_{50}$-values were determined for example compounds as listed below in Table 1 (A=$EC_{50}$<25 nM; B=25≤$EC_{50}$<100 nM; C=$EC_{50}$≥100 nM).

TABLE 1

| Group | Example # |
|---|---|
| A | 4, 8, 10, 13/8, 13/9, 14/1, 14/2 |
| B | 1, 2, 5, 6, 8A, 13/1, 13/3, 13/4, 13/5, 13/7 |
| C | 13/2, 13/6 |

Mammalian One Hybrid (M1H) Assay

Determination of a ligand mediated Gal4 promoter driven transactivation to quantify ligand binding mediated activation of FXR was performed as follows: The cDNA part encoding the FXR ligand binding domain was cloned into vector pCMV-BD (Stratagene) as a fusion to the yeast GAL4 DNA binding domain under the control of the CMV promoter. The amino acid boundaries of the ligand binding domain were amino acids 187-472 of Database entry NM_005123 (RefSeq). The plasmid pFR-Luc (Stratagene) was used as the reporter plasmid, containing a synthetic promoter with five tandem repeats of the yeast GAL4 binding sites, driving the expression of the Photinus pyralis (American firefly) luciferase gene as the reporter gene. In order to improve experimental accuracy the plasmid pRL-CMV (Promega) was cotransfected. pRL-CMV contains the constitutive CMV promoter, controlling the expression of the Renilla reniformis luciferase. All Gal4 reporter gene assays were done in HEK293 cells (obtained from DSMZ, Braunschweig, Germany) grown in MEM with L-Glutamine and Earle's BSS supplemented with 10% fetal bovine serum, 0.1 mM nonessential amino acids, 1 mM sodium pyruvate, and 100 units Penicilin/Streptavidin per mL at 37° C. in 5% $CO_2$. Medium and supplements were obtained from Invitrogen. For the assay, 5×10⁵ cells were plated per well in 96 well plates in 100 µL per well MEM without Phenol Red and L-Glutamine and with Earle's BSS supplemented with 10% charcoal/dextran treated FBS (HyClone, South Logan, Utah), 0.1 mM nonessential amino acids, 2 mM glutamine, 1 mM sodium pyruvate, and 100 units Penicilin/Streptavidin per mL, incubated at 37° C. in 5% $CO_2$. The following day the cells were >90% confluence. Medium was removed and cells were transiently transfected using 20 µL per well of a OptiMEM—polyethylene-imine-based transfection-reagent (OptiMEM, Invitrogen; Polyethyleneimine, Aldrich Cat No. 40,827-7) including the three plasmids described above. MEM with the same composition as used for plating cells was added 2-4 h after addition of transfection mixture. Then compound stocks, prediluted in MEM were added (final vehicle concentration not exceeding 0.1%). Cells were incubated for additional 16 h before firefly and renilla luciferase activities were measured sequentially in the same cell extract using a Dual-Light-Luciferase-Assay system (Dyer et al., Anal. Biochem. 2000, 282, 158-161). All experiments were done in triplicates.

To assess the FXR agonistic potency of the example compounds, potency ranges were determined in the M1H assay as listed below in Table 2 (A=$EC_{50}$<25 nM; B=25≤$EC_{50}$<100 nM; C=$EC_{50}$≥100 nM).

TABLE 2

| Group | Example # |
|---|---|
| A | 13/4, 13/5, 13/6 |
| B | 2, 8, 8A, 10, 13/1, 13/3, 13/7 |
| C | 1, 4, 5, 6, 13/2, 13/8, 13/9, 14/1 |

Aqueous Solubility Assay

The aq. solubility in PBS, pH 7.4 was determined as follows. A 10 mM compound stock solution in DMSO was added to PBS (pH 7.4) to reach a theoretical final concentration of 200 μM. The resulting solution/suspension was shaken at 1250 rpm for 1 h and then stored in the dark at rt for 23 h. At this time any precipitate is separated from the solution by centrifugation at 3900 rpm for 30 min. The aq. solubility was determined by comparing the peak area of the principle peak in a calibration standard (200 μM) in an organic solvent (methanol/water 60:40, v/v) with the peak area of the corresponding peak in the buffer sample. As detection method was used HPLC-UV/VIS at 230 nm.

Parallel Artificial Membrane Permeation Assay (PAMPA)

For the PAMPA, 5 mM stock solutions of test items were prepared in DMSO. 5 mM stock solutions of reference items were prepared in EtOH (carbamazepine, guanabenz) or in EtOH:$H_2O$ 1:1 (v/v) (ceftriaxone), respectively. Compounds were diluted in PBS (pH 7.4) to obtain the starting solutions containing 5% of the respective organic solvent and 250 μM reference compounds or 10 μM test items, respectively. For the assay, a modified procedure of the PAMPA as described by Kansy et al. Kansy et al. (J. Med. Chem. 1998, 41, 1007) was used. The reference compounds for low (ceftriaxone), medium (guanabenz) and high permeation (carbamazepine) were included as internal controls.

Permeation experiments were carried out in a Multiscreen 96 well tray (donor) covered by a 96-well Multiscreen Immobilon (acceptor). The hydrophobic filter material of the Immobilon plate was pre-wetted with 70% ethanol and treated with a solution of lipids (lecithin dissolved in dodecane). The donor plate was filled with test compounds and reference compounds and both plates were inserted into each other and placed onto an orbital shaker for 15 min at 100 rpm. The transport study was started by applying 150 μL PBS-buffer containing the test and reference compounds to the donor plate. After 15-16 h of diffusion at rt, the contents of the acceptor and donor plate were collected and quantified using LC/MS-detection (test items) or by UV spectroscopy using a Spectramax Plus[384] (Molecular Devices) (reference items). The absorption maxima for the reference items ceftriaxone, guanabenz and carbamazepine were 240 nm, 270 nm and 286 nm, respectively. Recovery samples were prepared as described for the permeation assay samples and were incubated in representative vials during the permeation period under the same conditions.

For LC/MS analysis of the test items, 100 μL incubate were removed from acceptor and donor compartment and processed for acetonitrile (ACN) precipitation as described below. Additionally, test item samples from the lipid layer were extracted by flushing each well two times with 150 μL EA. The solutions were collected in 1.5 mL reaction tubes and the solvent was evaporated. The dried residues were resuspended in a PBS/DMSO/ACN mixture reflecting the composition of the acceptor and donor samples (i.e. 100 μL buffer supplemented with 5% DMSO, 200 μL ACN+ISTD). The final solvent content of each sample was 66% ACN.

Samples from donor and acceptor compartments and calibration standards were precipitated by addition of 200 μL ACN/ISTD or 400 μL ACN/ISTD, respectively. After vigorous shaking (10 seconds) and centrifugation (5 min at 4800×g, rt), the particle free supernatants were subjected to LC-MS/MS. Membrane compartments were extracted as described above. After reconstitution, samples were vigorously shaken (10 seconds) and spun down (5 min at 4800×g, rt). The particle free supernatants were subjected to LC-MS/MS.

For analysis of compounds under the present invention, the HPLC system consisted of an Accela U-HPLC pump and an Accela auto sampler (Thermo Fisher Scientific, USA). Mass spectrometry was performed on an Exactive mass spectrometer (orbitrap technology with accurate mass) equipped with an heated electrospray (H-ESI2) interface (Thermo Fisher Scientific, USA) connected to a PC running the standard software Xcalibur 2.1.

The LC was performed in the gradient mode (Table 3) using ACN/0.1% formic acid as organic phase (A) and 10 mM ammonium formate/0.1% formic acid as aq. phase (B); and the pump flow rate was set to 500 μL/min. Separation was performed on a Gemini C6-Phenyl, 3 μm, 50×2.0 mm (Phenomenex, Germany) analytical column with a pre-column (Gemini C6-Phenyl, 3 μm, 4×2.0 mm).

TABLE 3

| HPLC gradients | | | | | | |
|---|---|---|---|---|---|---|
| Mobile phase | 0 min | 0.1 min | 1.2 min | 2.6 min | 2.7 min | 3.5 min |
| A (%) | 5 | 5 | 97 | 97 | 5 | 5 |
| B (%) | 95 | 95 | 3 | 3 | 95 | 95 |

As MS tune file a generic tune file was used for all analytes applying the positive or negative ion mode. As lock mass for internal mass calibration the [M+H]$^+$ ion of diisooctyl phthalate (m/z 391.28429), which is ubiquitously present in the solvent system, was used.

Analyte was acquired by scanning ±1 Thomson around the expected mass of the monoisotopic [M+H]$^+$ or [M−H]$^-$ ion. The mass resolution of the Orbitrap was set to 50,000. The accurate mass of each analyte was used for peak integration. Further instruments settings were as follows: HCD-Gas off, AGC high dynamic range, max. trap injection time 100 ms, sheath gas 30, aux gas 8, sweep gas 2, spray voltage 4 kV, capillary temperature 250° C., ESI 2 heater temperature 250° C.

The objective of the present invention was to generate FXR-agonists with improved physico-chemical properties compared to compounds claimed in WO 2011/020615. This was achieved by the introduction of a polar hydroxyl group on a 1,3-cyclobutylidene or 1,3-azetidinylidene group replacing the former 1,2-cyclopropylidene ring.

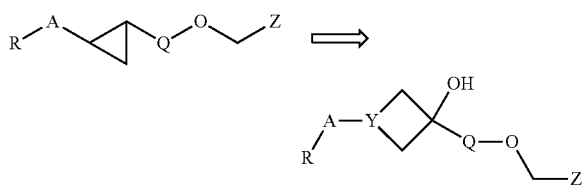

Surprisingly, the resulting compounds maintained their activity on the FXR receptor but demonstrated improved physico-chemical properties, such as higher aq. solubility and/or membrane permeability. A direct comparison of the corresponding compounds of the two series is given in Table 4.

TABLE 4
| Structure | Aqueous solubility (PBS, pH 7.4) | PAMPA, Membrane permeability in % Flux * | clogD (ChemAxon software) |
| --- | --- | --- | --- |
| 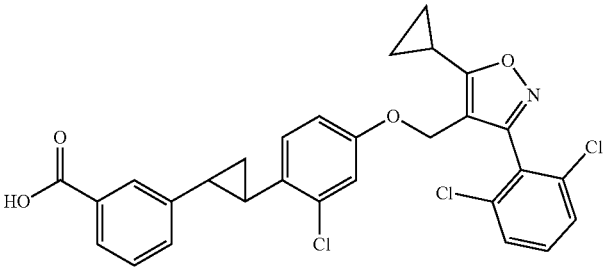 [SMILES: O=C(O)c1cccc(C2CC2c2ccc(OCc3c(-c4c(Cl)cccc4Cl)noc3C3CC3)cc2Cl)c1] | 20 μM | 13.6 | 5.1 |
| 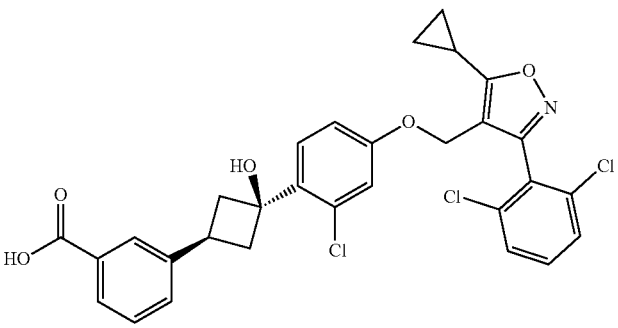 [SMILES: O=C(O)c1cccc([C@H]2C[C@](O)(c3ccc(OCc4c(-c5c(Cl)cccc5Cl)noc4C4CC4)cc3Cl)C2)c1] | 192 μM | 24.0 | 4.4 |
| 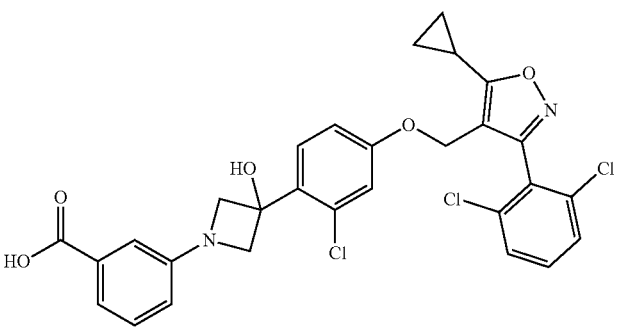 [SMILES: O=C(O)c1cccc(N2CC(O)(c3ccc(OCc4c(-c5c(Cl)cccc5Cl)noc4C4CC4)cc3Cl)C2)c1] | 195 μM | n.d.** | 4.4 |
| 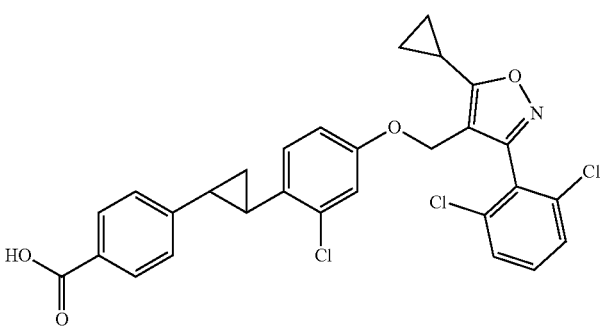 [SMILES: O=C(O)c1ccc(C2CC2c2ccc(OCc3c(-c4c(Cl)cccc4Cl)noc3C3CC3)cc2Cl)cc1] | 72 μM | 20.7 | 5.2 |

TABLE 4-continued

| Structure | Aqueous solubility (PBS, pH 7.4) | PAMPA, Membrane permeability in % Flux * | clogD (ChemAxon software) |
|---|---|---|---|
| | 192 µM | 21.1 | 4.5 |
| | 158 µM | 28.9 | 4.2 |
| | 171 µM | 46.1 | 3.5 |

* Flux (%) = (c acceptor well)/sum (c donor well + c acceptor well) × 100 × 2
**n.d. = not determined In each case either the aqueous solubility or the PAMPA membrane permeability or both are significantly improved by the introduction of the hydroxy-cyclobutyl or hydroxy-azetidyl moiety. As most nuclear receptor active molecules, FXR agonists are generally very lipophilic (M. L. Crawley, Expert Opin. Ther. Patents 2010, 20, 1047). Therefore, better aqeous solubility and membrane permeability are supposed to result in a higher oral bioavailability and in general in a better suitability for clinical development of those compounds as drugs (L. Huang, J. Dong, S. Karki in Evaluation of drug candidates for preclinical development (Eds. C. Han, C. B. Davis, B. Wang), Wiley & Sons, Hoboken 2010, 187-217).

The invention claimed is:

1. A tris(hydroxymethyl)aminomethane salt of the following compound:

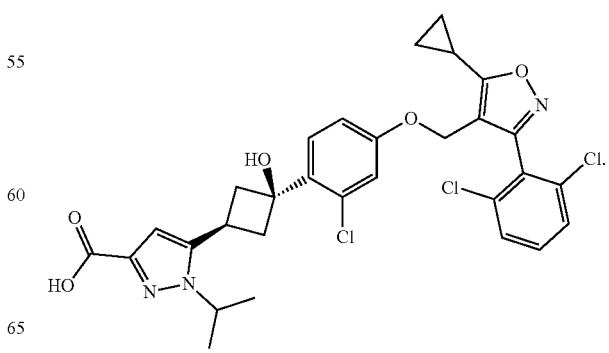

2. A tris(hydroxymethyl)aminomethane salt of the following compound:

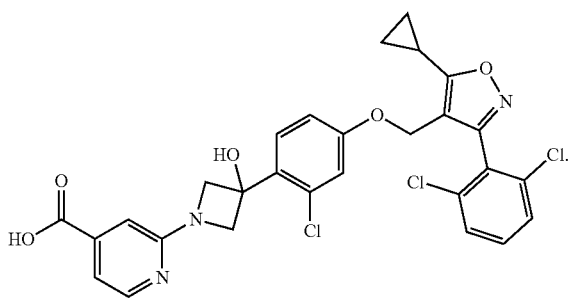 [SMILES: O=C(O)c1ccnc(N2CC(O)(c3ccc(OCc4c(-c5c(Cl)cccc5Cl)noc4C4CC4)cc3Cl)C2)c1]

3. A pharmaceutical composition comprising the salt of claim 1 and a pharmaceutically acceptable carrier.

4. A pharmaceutical composition comprising the salt of claim 2 and a pharmaceutically acceptable carrier.

5. A method for the treatment of Non-Alcoholic Steatohepatitis (NASH) comprising administering the salt of claim 1 to a patient in need thereof.

6. A method for the treatment of Primary Biliary Cirrhosis (PBC) comprising administering the salt of claim 1 to a patient in need thereof.

7. A method for the treatment of Primary Sclerosing Cholangitis (PSC) comprising administering the salt of claim 1 to a patient in need thereof.

8. A method for the treatment of Non-Alcoholic Steatohepatitis (NASH) comprising administering the salt of claim 2 to a patient in need thereof.

9. A method for the treatment of Primary Biliary Cirrhosis (PBC) comprising administering the salt of claim 2 to a patient in need thereof.

10. A method for the treatment of Primary Sclerosing Cholangitis (PSC) comprising administering the salt of claim 2 to a patient in need thereof.

11. A method for the treatment of Non-Alcoholic Steatohepatitis (NASH) comprising administering the pharmaceutical composition of claim 3 to a patient in need thereof.

12. A method for the treatment of Primary Biliary Cirrhosis (PBC) comprising administering the pharmaceutical composition of claim 3 to a patient in need thereof.

13. A method for the treatment of Primary Sclerosing Cholangitis (PSC) comprising administering the pharmaceutical composition of claim 3 to a patient in need thereof.

14. A method for the treatment of Non-Alcoholic Steatohepatitis (NASH) comprising administering the pharmaceutical composition of claim 4 to a patient in need thereof.

15. A method for the treatment of Primary Biliary Cirrhosis (PBC) comprising administering the pharmaceutical composition of claim 4 to a patient in need thereof.

16. A method for the treatment of Primary Sclerosing Cholangitis (PSC) comprising administering the pharmaceutical composition of claim 4 to a patient in need thereof.

\* \* \* \* \*